(12) United States Patent
Lautenschütz et al.

(10) Patent No.: US 12,398,410 B2
(45) Date of Patent: Aug. 26, 2025

(54) ENZYMATIC METHOD FOR THE PRODUCTION OF L-GLUFOSINATE P-ESTERS

(71) Applicant: Evonik Operations GmbH, Essen (DE)

(72) Inventors: Ludger Lautenschütz, Hanau (DE); Steffen Oßwald, Nidderau (DE); Markus Pötter, Muenster (DE); Jakob Müller, Haltern am See (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 18/846,061

(22) PCT Filed: Mar. 14, 2022

(86) PCT No.: PCT/EP2022/056539
§ 371 (c)(1),
(2) Date: Sep. 11, 2024

(87) PCT Pub. No.: WO2023/174511
PCT Pub. Date: Sep. 21, 2023

(65) Prior Publication Data
US 2025/0109417 A1    Apr. 3, 2025

(51) Int. Cl.
*C12P 13/04* (2006.01)
*C12N 9/80* (2006.01)
*C12N 9/86* (2006.01)
*C12N 9/90* (2006.01)
*C12N 15/52* (2006.01)
*C12N 15/70* (2006.01)

(52) U.S. Cl.
CPC ............... *C12P 13/04* (2013.01); *C12N 9/80* (2013.01); *C12N 9/86* (2013.01); *C12N 9/90* (2013.01); *C12N 15/52* (2013.01); *C12N 15/70* (2013.01); *C12Y 305/01087* (2013.01); *C12Y 305/02002* (2013.01); *C12Y 501/99005* (2013.01)

(58) Field of Classification Search
None
See application file for complete search history.

(56) References Cited

U.S. PATENT DOCUMENTS

| | | | |
|---|---|---|---|
| 5,442,088 A | 8/1995 | Hoffmann | |
| 6,359,162 B1 | 3/2002 | Willms | |
| 6,524,837 B1 | 2/2003 | Arnold et al. | |
| 7,217,544 B2 | 5/2007 | Hummel et al. | |
| 7,288,402 B2 | 10/2007 | Osswald et al. | |
| 7,491,521 B2 | 2/2009 | Osswald et al. | |
| 7,592,165 B2 | 9/2009 | Osswald et al. | |
| 7,943,359 B2 | 5/2011 | Osswald et al. | |
| 9,765,370 B2 | 9/2017 | Hennemann et al. | |
| 9,957,536 B2 | 5/2018 | Osswald et al. | |
| 10,822,627 B2 | 11/2020 | Osswald et al. | |
| 2003/0175910 A1 | 9/2003 | Altenbuchner et al. | |
| 2005/0214912 A1 | 9/2005 | Nozaki et al. | |
| 2006/0063238 A1 | 3/2006 | Hummel et al. | |
| 2006/0068467 A1 | 3/2006 | Osswald et al. | |
| 2006/0210989 A1 | 9/2006 | May et al. | |
| 2006/0228787 A1 | 10/2006 | May et al. | |
| 2007/0128689 A1 | 6/2007 | May et al. | |
| 2008/0057549 A1 | 3/2008 | Osswald et al. | |
| 2008/0102496 A1 | 5/2008 | Verseck et al. | |
| 2008/0248538 A1 | 10/2008 | Osswald et al. | |
| 2010/0021977 A1 | 1/2010 | May et al. | |
| 2010/0143981 A1 | 6/2010 | Rusnak-Müller et al. | |
| 2010/0261250 A1 | 10/2010 | Osswald et al. | |
| 2014/0308717 A1 | 10/2014 | Haas et al. | |
| 2015/0056667 A1 | 2/2015 | Osswald et al. | |
| 2015/0111254 A1 | 4/2015 | Hennemann et al. | |
| 2017/0253897 A1 | 9/2017 | Green et al. | |
| 2018/0237814 A1 | 8/2018 | Osswald et al. | |
| 2020/0181179 A1 | 6/2020 | Fields et al. | |
| 2021/0214754 A1 | 7/2021 | Green et al. | |
| 2022/0024955 A1 | 1/2022 | Jeon et al. | |
| 2022/0194896 A1 | 6/2022 | Lautenschuetz et al. | |
| 2022/0306658 A1 | 9/2022 | Jeon et al. | |
| 2024/0117327 A1 | 4/2024 | Pötter et al. | |
| 2024/0287558 A1 | 8/2024 | Lautenschütz et al. | |

FOREIGN PATENT DOCUMENTS

| | | |
|---|---|---|
| CN | 106083922 | 11/2016 |
| CN | 108516991 | 9/2018 |
| CN | 111662325 | 9/2020 |

(Continued)

OTHER PUBLICATIONS

Expasy, Enzyme entry EC 3.5.1.87, enzyme.expasy.org/EC/3.5.1.87 (retrieved Feb. 8, 2025). (Year: 2025).*
Expasy, Enzyme entry EC 5.1.99.5, enzyme.expasy.org/EC/5.1.99.5 (retrieved Feb. 8, 2025). (Year: 2025).*
Expasy, Enzyme entry EC 3.5.2.2, enzyme.expasy.org/EC/3.5.2.2. (retrieved Feb. 8, 2025). (Year: 2025).*
Avendaño et al., "Hydantoin and its derivatives", Kirk-Othmer Encyclopedia of Chemical Technology, 2000, pp. 1-21.
Bommarius et al., "A direct route from hydantoins to D-amino acids employing a resting cell biocatalyst with D-hydantoinase and D-carbamoylase acitivity", Series C: Mathematical and Physical Sciences, vol. 381, 1992, 2 pages.

(Continued)

*Primary Examiner* — Todd M Epstein
(74) *Attorney, Agent, or Firm* — Grüneberg and Myers PLLC

(57) ABSTRACT

A first enzymatic method for the production of an L-glufosinate P-ester includes reacting an L-glufosinate P-ester carbamoylate to give the corresponding L-glufosinate P-ester in the presence of a carbamoylase as a catalyzer. A second enzymatic method includes the enantioselective production of an L-glufosinate P-ester from a mixture $M_{IIIA}$ of L- and D-glufosinate P-ester hydantoins. The L-glufosinate P-ester obtained in the two methods may be saponified to give L-glufosinate.

13 Claims, 2 Drawing Sheets

Figure 1:
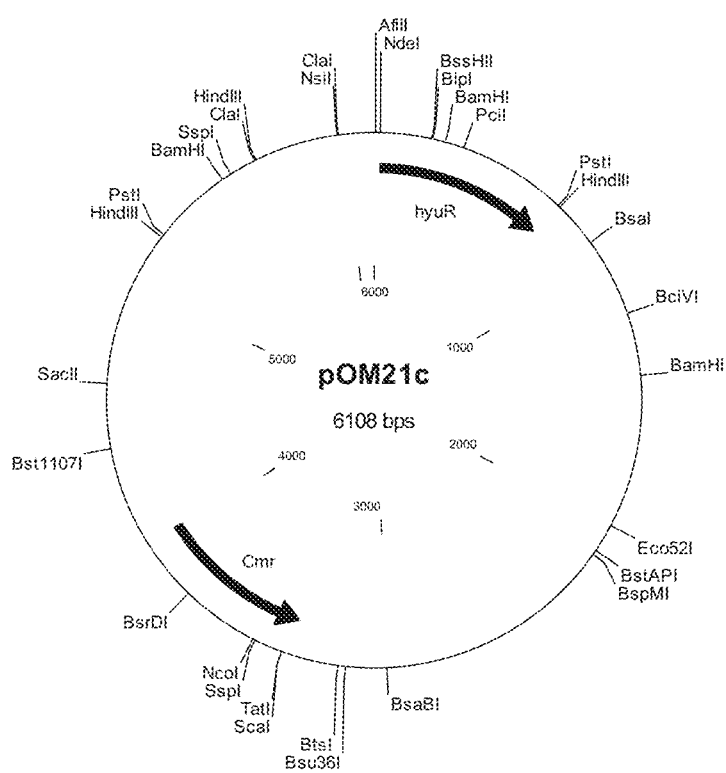

Specification includes a Sequence Listing.

(56) References Cited

FOREIGN PATENT DOCUMENTS

| | | | |
|---|---|---|---|
| DE | 31 42 036 | 5/1983 | |
| EP | 0 508 296 | 10/1992 | |
| EP | 1 829 975 | 9/2007 | |
| EP | 2 739 744 | 2/2013 | |
| EP | 4 151 643 | 3/2023 | |
| WO | 99/09039 | 2/1999 | |
| WO | 00/58449 | 10/2000 | |
| WO | 01/23582 | 4/2001 | |
| WO | 2005/090577 | 9/2005 | |
| WO | 2008/067981 A2 | 6/2008 | |
| WO | 2008/067981 A3 | 6/2008 | |
| WO | 2013/020839 | 2/2013 | |
| WO | 2013/072486 | 5/2013 | |
| WO | 2014/067746 | 5/2014 | |
| WO | 2017/151573 | 9/2017 | |
| WO | 2019/018406 | 1/2019 | |
| WO | 2020/051188 A1 | 3/2020 | |
| WO | 2020/051188 A8 | 3/2020 | |
| WO | 2020/145513 | 7/2020 | |
| WO | 2020/145514 | 7/2020 | |
| WO | 2020/145627 | 7/2020 | |
| WO | 2022/207543 | 10/2022 | |
| WO | WO-2023105079 A1 * | 6/2023 | ............ A01N 43/28 |
| WO | 2023/174511 | 9/2023 | |

OTHER PUBLICATIONS

Bovarnick et al., "Racemization of Tripeptides and Hydantoins", Journal of the American Chemical Society, vol. 60, Oct. 1938, pp. 2426-2430.

Clemente-Jiménez et al., "Optically Pure α-Amino Acids Production by the Hydantoinase Process", Recent Patents on Biotechnology, vol. 2, No. 1, 2008, pp. 35-46.

Elinor Ware, "The Chemistry Of The Hydantoins", Chem. Rev., vol. 46, Nov. 3, 1949, pp. 403-470.

Engel et al., "The Hydantoinase Process: Recent Developments for the Production of Non-Canonical Amino Acids", Industrial biocatalysis, 2015, pp. 817-862.

Gerhard Hoerlein, "Glufosinate (Phosphinothricin), A Natural Amino Acid with Unexpected Herbicidal Properties", Reviews of Environmental Contamination and Toxicology, vol. 138, Feb. 5, 1994, pp. 73-145.

Heras-Vázquez et al., "Hydantoin Racemase: the Key Enzyme for the Production of Optically Pure α-Amino Acids", Modern Biocatalysis: Stereoselective and Environmentally Friendly Reactions, 2009, pp. 173-193.

International Search Report received for PCT Application No. PCT/EP2022/056539, mailed on Dec. 21, 2022, 7 pages.

Karl-Josef Haack, "Synthese-Entwicklung unter speziellen Randbedingungen (Synthesis development under special boundary conditions)", Chem. Unserer Zeit, vol. 37, 2003, 14 pages with English translation.

Latacz et al., "Hydantoinazy, ich znaczenie, podział i zastosowanie w biotechnologii (Hydantoinases and their role, classification and use in biotechnology)", Biotechnologia, vol. 2, No. 73, 2006, 32 pages with English translation.

May et al., "Development Of Dynamic Kinetic Resolution Processes for Biocatalytic Production of Natural and Nonnatural L-Amino Acids", Organic Process Research & Development, vol. 6, No. 4, Jan. 1, 2002, pp. 452-457.

Ogawa et al., "Purification and characterization of N-carbamoyl-L-amino acid amidohydrolase with broad substrate specificity from *Alcaligenes xylosoxidans*". Appl. Microbiol. Biotechnol., vol. 43, Feb. 13, 1995, pp. 1039-1043.

Robert A. Lazarus, "Chemical Racemization of 5-Benzylhydantoin", J. Org. Chem., 1990, vol. 55, No. 15, pp. 4755-4757.

Rodríguez et al., "Overview on Multienzymatic Cascades for the Production of Non-canonical α-Amino Acids", frontiers in Bioengineering and Biotechnology, vol. 8. Aug. 11, 2020, pp. 1-36.

Ruhland et al., "A comparative investigation of the metabolism of the herbicide glufosinate in cell cultures of transgenic glufosinate-resistant and non-transgenic oilseed rape (*Brassica napus*) and corn (*Zea mays*)", Environ. Biosafety Res., vol. 1, No. 1, Oct. 1, 2002, pp. 29-37.

Slomka et al., "Chemical synthesis and enzymatic, stereoselective hydrolysis of a functionalized dihydropyrimidine for the synthesis of β-amino acids", AMB Expr, vol. 5, No. 85, Dec. 11, 2015, pp. 1-8.

Thomas Waniek, "Untersuchungen zur Substratspezifität und Enantioselektivität mikrobieller Hydantoinasen(Substrate specificity studies and enantioselectivity of microbial hydantoinases)", Institut für Bioverfahrenstechnik Lehrstuhl Physiologische Mikrobiologie Universität Stuttgart, 2000, 323 pages with English translation.

Wilms et al., "Cloning, nucleotide sequence and expression of a new L-N-carbamoylase gene from *Arthrobacter aurescens* DSM 3747 in *E. coli*", Journal of Biotechnology, vol. 68, 1999, pp. 101-113.

Written Opinion received for PCT Application No. PCT/EP2022/056539, mailed on Dec. 21, 2022, 9 pages.

Yokozeki et al., "Mechanism of Asymmetric Production of L-Aromatic Amino Acids from the Corresponding Hydantoins by *Flavobacterium* sp.", Agric. Biol. Chem., vol. 51, No. 3, 1987, pp. 737-746.

U.S. Appl. No. 12/441,145, filed Mar. 13, 2009, 2010/0021977, May et al.

U.S. Appl. No. 14/237,121, filed Feb. 20, 2014, 2014/0308717, Haas et al.

U.S. Appl. No. 61/721,445, filed Nov. 1, 2012, Osswald et al.

U.S. Appl. No. 17/425,907, filed Jul. 26, 2021, 2022/0194896, Lautenschuetz et al.

U.S. Appl. No. 18/569,989, filed Dec. 13, 2023, 2024/0287558, Lautenschüetz et al.

\* cited by examiner

ENZYMATIC METHOD FOR THE PRODUCTION OF L-GLUFOSINATE P-ESTERS

CROSS-REFERENCE TO RELATED APPLICATIONS

This application is a National Stage entry under § 371 of International Application No. PCT/EP2022/056539, filed on Mar. 14, 2022. The content of this application is hereby incorporated by reference in its entirety.

REFERENCE TO A SEQUENCE LISTING

The present application is accompanied by an XML file as a computer readable form containing the sequence listing entitled, "006128USPCT-SeqList.txt", created on Sep. 11, 2024, with a file size of 86,979 bytes, the content of which is hereby incorporated by reference in its entirety.

BACKGROUND OF THE INVENTION

Field of the Invention

The present invention relates in a first aspect to an enzymatic method for the production of an L-glufosinate P-ester. This method is characterized by a step (c) in which an L-glufosinate P-ester carbamoylate is reacted to give the corresponding L-glufosinate P-ester. This step (c) is catalyzed by a carbamoylase, preferably by an L-enantioselective carbamoylase.

The L-glufosinate P-ester carbamoylate employed in step (c) may be obtained by reaction from the corresponding L-glufosinate hydantoin P-ester. This optional, antecedent step (b) is catalyzed by a hydantoinase, preferably an L-enantioselective hydantoinase. Even more preferred, the L-glufosinate hydantoin P-ester employed in step (b) may be obtained by reaction from the corresponding D-glufosinate hydantoin P-ester. This optional, antecedent step (a) is preferably catalyzed by a hydantoin racemase.

In a second aspect, the present invention relates to an enzymatic method for enantioselective production of an L-glufosinate P-ester from a mixture $M_{IIIA}$ of L- and D-glufosinate P-ester hydantoins. In the method according to the second aspect of the invention, the mixture $M_{IIIA}$ is provided in a step (i-A) and employed in steps (ii) and (iii). Steps (ii) and (iii) correspond to steps (b) and (c) described above, respectively, wherein in step (c), an L-carbamoylase is employed.

In an optional, preferred step (i-B) of the method according to the second aspect of the invention, corresponding to preferred step (a) described above, a hydantoin racemase is preferably used to convert at least a part of the D-glufosinate P-ester hydantoin in the mixture $M_{IIIA}$ into its corresponding L-isomer, giving a mixture $M_{IIIB}$, which is then employed in steps (ii) and (iii).

The L-glufosinate P-ester obtained in the methods according to the first or second aspect of the invention may be saponified to give L-glufosinate.

Description of Related Art

Organic phosphorous compounds, i.e. chemical agents comprising a carbon-phosphor bond, are widely applied as herbicides in the area of plant protection. Agents such as the herbicides glyphosate (Roundup®, Touchdown®) and glufosinate (Basta®, Liberty®) as well as the growth regulator glyphosine (Polaris®) are used for this purpose (as described for example by G. Hörlein, Rev. Environ. Contam. Toxicol. 1994, 138, 73-145).

The esters of P-methyl phosphinic acid (for example, P-methyl phosphinic acid butyl ester; "MPBE"; CAS-No: 6172-80-1) have a key role as synthetic building blocks in the synthesis of the non-selective herbicide glufosinate. These esters are accessible via two fundamental synthetic pathways (summarized in FIGS. 3 a and 3 b, page 130, of the article of K. Haack, Chem. Unserer Zeit 2003, 37, 128-138):

a. Reacting diethyl chlorophosphite [ClP(OC$_2$H$_5$)$_2$] with CH$_3$MgCl provides methyl diethoxy phosphine [H$_3$CP (OC$_2$H$_5$)$_2$; "DEMP"; CAS-No. 15715-41-0], which is partially hydrolyzed to give the corresponding methylphosphinic acid ethyl ester (MPEE; CAS-Nr: 16391-07-4).

b. Alternatively, methane can be reacted with phosphor trichloride at 500° C. to give methyl dichloro phosphane H$_3$CPCl$_2$. The latter can then be solvolyzed in alcohols to give the corresponding methyl phosphinic acid esters.

The esters of P-methyl phosphinic acid add to carbon-carbon double bonds regioselectively. This property is used in the synthesis of glufosinate for the formation of the second phosphor-carbon bond. For example, H$_3$CPH(O)OR (R=Alkyl) reacts with 1-cyano allyl acetate in an addition reaction to provide an intermediate. Subsequent exchange of the acetate substituent with ammonia and hydrolysis of the cyano group and the ester group of the phosphinic acid moiety give glufosinate.

Acrylic acid ester is a cheaper alternative starting material. It can react with the ester of P-methyl phosphinic acid to 3-[alkoxy(methyl)phosphinyl]propionic acid alkyl ester. Claisen reaction of this diester with diethyl oxalate, hydrolysis and decarboxylation provide the corresponding α-keto acid, which can be reductively aminated to give glufosinate.

These and further synthetic routes towards glufosinate are also described in the art, e.g. in WO 1999/009039 A1, EP 0 508 296 A1.

A general disadvantage of all synthetic routes to glufosinate is that the obtained glufosinate is a racemic mixture. However, as there is no herbicidal activity of the D-enantiomer, L-glufosinate [hereinafter "LGA"; CAS-Nr. 35597-44-5; other names "(S)-glufosinate", "(−)-glufosinate"] is the enantiomer of economical interest.

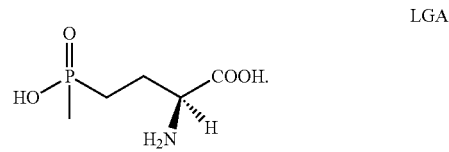

LGA

For example, CN 111662325 A discloses a synthetic pathway in which L-homoserine is reacted to the respective hydantoin, followed by addition of methane phosphor dichloride, which results in a methane phosphane which is disubstituted with L-homoserine hydantoin. After a final Arbuzov reaction and hydrolysis, LGA is obtained. Although the disclosure describes a high enantiomeric excess (="ee"), this ee could not be reproduced by the inventors of the present invention. A reason could be that during this synthesis pathway, strong acidic (HCl for saponification of the hydantoin phosphor bond) and alkaline conditions (NaOH, 100° C. for ring opening) are applied. Such conditions usually lead to racemization, as described by M. Bovarnick & H. T. Clarke, Journal of the American Chemical Society 1938, 60, 2426-2430, by R. A. Lazarus, J. Org. Chem. 1990, 55, 4755-4757, and by A. S. Bommarius, M. Kottenhahn, H. Klenk, K. Drauz: "A direct route from hydantoins to D-amino acids employing a resting cell biocatalyst with D-hydantoinase and D-carbamoylase acitivity" on page 164 and 167 in "Microbial Reagents in Organic Synthesis" Series C: Mathematical and Physical Sciences-Vol. 381, S. Servi (Ed.), 1992, Springer Science+Business Media, B. V., Dordrecht.

For enantioselective syntheses of LGA, chemical and enzymatic pathways are described in the art.

WO 2020/145513 A1 and WO 2020/145514 A1 describe a chemical route to LGA. In this route, an L-homoserine derivative such as O-acetyl L-homoserine or O-succinyl L-homoserine is used as starting material and L-glufosinate is obtained by a sequence of reactions including lactonization and halogenation.

WO 2020/145627 A1 describes a similar route, wherein during halogenation, a bromo derivative is obtained.

The route disclosed by CN 106083922 A resembles these synthetic pathways but starts off from L-methionine.

CN 108516991 A describes another synthetic pathway to LGA, starting from the azeotropic dehydration of L-homoserine to give L-3,6-bis(2-haloethyl)-2,5-diketopiperazine, followed by introduction of a methylphosphonate diester group, and hydrolysis.

WO 2017/151573 A1 discloses a two-step enzymatic synthesis of LGA from D-glufosinate. In the first step, D-glufosinate is oxidatively deaminated to give 2-oxo-4-[hydroxy(methyl)phosphinoyl]-butyric acid ("PPO"), followed by the specific amination of PPO to LGA as the second step. The first step is carried out by catalysis of a D-amino acid oxidase, the second step is catalyzed by a transaminase.

WO 2020/051188 A1 discloses a similar method of converting racemic glufosinate to the L-enantiomer. In addition, it discloses a step in which the α-ketoacid or ketone byproduct formed during amination of PPO with an amine donor is converted by ketoglutarate decarboxylase to further shift the equilibrium to LGA.

WO 2019/018406 A1 discloses a method of purifying LGA from a mixture comprising LGA and glutamate. Glutamate is converted to pyroglutamate enzymatically by glutaminyl-peptidyl cyclotransferase, and LGA is then purified from the resulting mixture with an ion-exchange resin.

WO 2013/072486 A1 disclose hydantoinase mutants which have a greater activity towards D-amino acids.

WO 00/58449 A1 disclose hydantoinase mutants which have a greater activity towards L-amino acids.

The object of the present invention is to provide a further enzymatic process for producing glufosinate or glufosinate P-esters. This process should provide products with a high excess of the L-enantiomer over the D-enantiomer. Moreover, this process should allow to use new substrates which heretofore were not used in the enzymatic synthesis of glufosinate or glufosinate esters. Moreover, there is a need in the art for an enantioselective method for the production of L-glufosinate or L-glufosinate esters from starting materials comprising D- and L-enantiomers, such as racemic mixtures, in a minimal number of synthetic steps.

SUMMARY OF THE INVENTION

Namely, it was surprisingly found that the desired L-glufosinate P-esters can be produced by an enzymatically catalyzed reaction from the corresponding carbamoylates of formula L-(II):

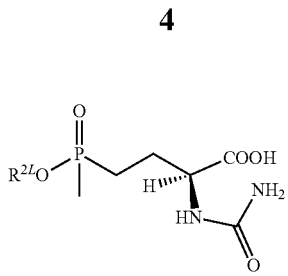

wherein $R^{2L}$ is a radical selected from the following formulae (VIII), (IX), (X), preferably selected from the following formulae (IX), (X), more preferably $R^{2L}$ has the following formula (IX):

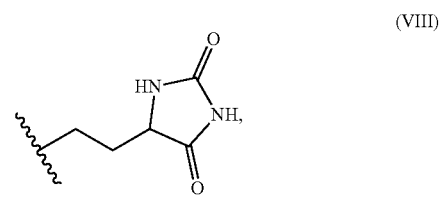

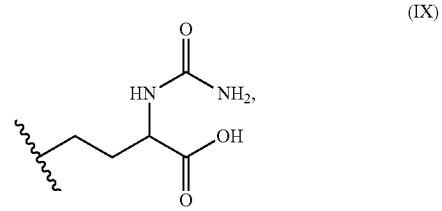

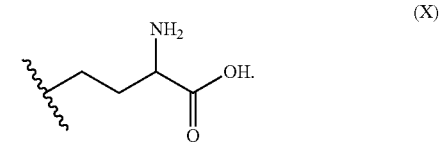

When $R^{2L}$ is a radical of the formula (VIII), the radical $R^{2L}$ may be selected from the formulae L-(VIII) and D-(VIII), and preferably has a formula according to L-(VIII):

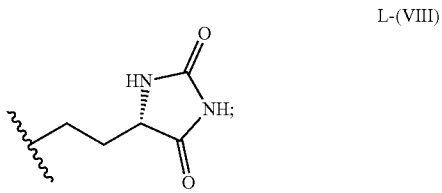

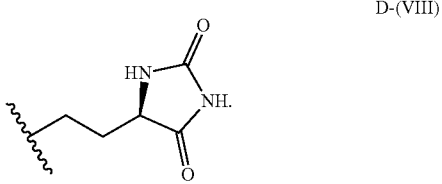

When $R^{2L}$ is a radical of the formula (IX), the radical $R^{2L}$ may be selected from the formulae L-(IX) and D-(IX), and preferably has a formula according to L-(IX):

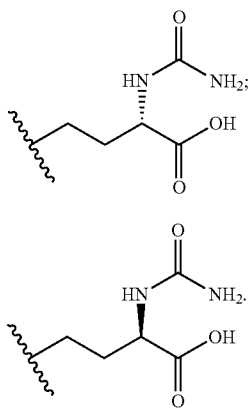

L-(IX)

D-(IX)

When $R^{2L}$ is a radical of the formula (X), the radical $R^{2L}$ may be selected from the formulae L-(X) and D-(X), and preferably has a formula according to L-(X):

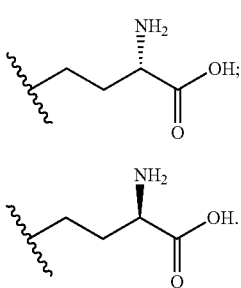

L-(X)

D-(X)

Such carbamoylates were not used in the enzymatically catalyzed production of L-glufosinate or its P-esters before. This finding was even more surprising, as it turned out that the presence of a radical selected from the following formulae (VIII), (IX), (X) is mandatory, as there is no corresponding reaction of compounds according to formula L-(II) in which $R^{2L}$=H.

α.1) The present invention hence solves the problems mentioned above by providing in a first aspect a method for the production of a glufosinate P-ester according to formula L-(I), comprising a step (c) in which a compound according to the above-mentioned formula L-(II) is reacted to give a compound according to formula L-(I):

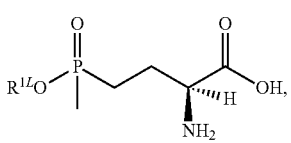

L-(I)

wherein $R^{1L}$ is a radical selected from the above-mentioned formulae (VIII), (IX), (X), preferably selected from the above-mentioned formulae (IX), (X), more preferably $R^{1L}$ has formula (X).

When $R^{1L}$ is a radical of the formula (VIII), the radical $R^{1L}$ may be selected from the above-mentioned formulae L-(VIII) and D-(VIII), preferably L-(VIII).

When $R^{1L}$ is a radical of the formula (IX), the radical $R^{1L}$ may be selected from the above-mentioned formulae L-(IX) and D-(IX), preferably L-(IX).

When $R^{1L}$ is a radical of the formula (X), the radical $R^{1L}$ may be selected from the above-mentioned formulae L-(X) and D-(X), preferably L-(X).

The reaction according step (c) is catalyzed by a carbamoylase $E_1$, preferably by an L-enantioselective carbamoylase $E_1$ ("L-enantioselective carbamoylase"="L-carbamoylase").

The L-carbamoylase $E_1$ is preferably categorized in the EC class 3.5.1.87.

The polypeptide sequence of the L-carbamoylase $E_1$ is preferably selected from SEQ ID NO: 1 and variants thereof, SEQ ID NO: 2 and variants thereof, SEQ ID NO: 3 and variants thereof, SEQ ID NO: 4 and variants thereof, SEQ ID NO: 5 and variants thereof, SEQ ID NO: 6 and variants thereof, SEQ ID NO: 7 and variants thereof, SEQ ID NO: 8 and variants thereof, SEQ ID NO: 9 and variants thereof.

α.2) In a preferred embodiment of the method according to the first aspect of the invention, the compound according to formula L-(II) that is employed in step (c) is obtained by a step (b) in which a compound according to formula L-(III) is reacted to give the compound according to formula L-(II):

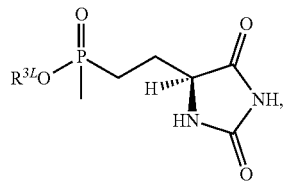

L-(III)

wherein the reaction according to step (b) is catalyzed by a hydantoinase $E_2$, preferably an L-enantioselective hydantoinase $E_2$ ("L-enantioselective hydantoinase"="L-hydantoinase").

$R^{3L}$ is a radical selected from the above-mentioned formulae (VIII), (IX), (X), preferably selected from the formulae (VIII), (IX), more preferably $R^{3L}$ has formula (VIII).

When $R^{3L}$ is a radical of the formula (VIII), the radical $R^{3L}$ may be selected from the above-mentioned formulae L-(VIII) and D-(VIII), preferably L-(VIII).

When $R^{3L}$ is a radical of the formula (IX), the radical $R^{3L}$ may be selected from the above-mentioned formulae L-(IX) and D-(IX), preferably L-(IX).

When $R^{3L}$ is a radical of the formula (X), the radical $R^{3L}$ may be selected from the above-mentioned formulae L-(X) and D-(X), preferably L-(X).

The hydantoinase $E_2$, in particular the L-hydantoinase $E_2$, is preferably categorized in the EC class 3.5.2.2.

The polypeptide sequence of the hydantoinase $E_2$, in particular the L-hydantoinase $E_2$, is preferably selected from SEQ ID NO: 10 and variants thereof, SEQ ID NO: 11 and variants thereof, SEQ ID NO: 12 and variants thereof, SEQ ID NO: 13 and variants thereof, SEQ ID NO: 14 and variants thereof, SEQ ID NO: 15 and variants thereof, SEQ ID NO: 16 and variants thereof.

α.3) In an even more preferred embodiment of the method according to the first aspect of the invention, the compound according to formula L-(III) that is employed in step (b) is obtained by a step (a) in which a compound according to formula D-(III) is reacted to give the compound according to formula L-(III):

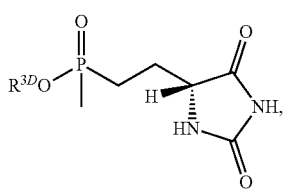

D-(III)

wherein the reaction according to step (a) is preferably catalyzed by a hydantoin racemase $E_3$.

$R^{3D}$ is a radical selected from the above-mentioned formulae (VIII), (IX), (X), preferably selected from the formulae (VIII), (IX), more preferably $R^{3D}$ has formula (VIII).

When $R^{3D}$ is a radical of the formula (VIII), the radical $R^{3D}$ may be selected from the above-mentioned formulae L-(VIII) and D-(VIII), preferably L-(VIII).

When $R^{3D}$ is a radical of the formula (IX), the radical $R^{3D}$ may be selected from the above-mentioned formulae L-(IX) and D-(IX), preferably L-(IX).

When $R^{3D}$ is a radical of the formula (X), the radical $R^{3D}$ may be selected from the above-mentioned formulae L-(X) and D-(X), preferably L-(X).

The hydantoin racemase $E_3$ is preferably categorized in the EC class 5.1.99.5.

The polypeptide sequence of the hydantoin racemase $E_3$ in step (a) is preferably selected from SEQ ID NO: 17 and variants thereof, SEQ ID NO: 18 and variants thereof, SEQ ID NO: 19 and variants thereof, SEQ ID NO: 20 and variants thereof, SEQ ID NO: 21 and variants thereof, SEQ ID NO: 22 and variants thereof, SEQ ID NO: 23 and variants thereof, SEQ ID NO: 24 and variants thereof, SEQ ID NO: 25 and variants thereof, SEQ ID NO: 26 and variants thereof.

It was further surprisingly found that the above-mentioned finding can be advantageously used for a method for enantioselective production of an L-glufosinate P-ester, in particular from mixtures of stereoisomers, preferably from mixtures of enantiomers, such as racemic mixtures.

β.1) Hence, the present invention relates in a second aspect to a method for the production of an L-glufosinate P-ester according to formula L-(I):

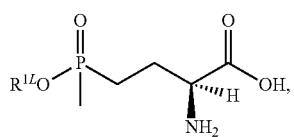

L-(I)

wherein $R^{1L}$ is a radical selected from the above-mentioned formulae (VIII), (IX), (X), preferably selected from the above-mentioned formulae (IX), (X), more preferably $R^{1L}$ has formula (X).

When $R^{1L}$ is a radical of the formula (VIII), the radical $R^{1L}$ may be selected from the above-mentioned formulae L-(VIII) and D-(VIII), preferably L-(VIII).

When $R^{1L}$ is a radical of the formula (IX), the radical $R^{1L}$ may be selected from the above-mentioned formulae L-(IX) and D-(IX), preferably L-(IX).

When $R^{1L}$ is a radical of the formula (X), the radical $R^{1L}$ may be selected from the above-mentioned formulae L-(X) and D-(X), preferably L-(X).

In this method, a mixture $M_{IIIA}$ comprising at least one compound L-(III) and at least one compound D-(III) is provided [step (i)-A]:

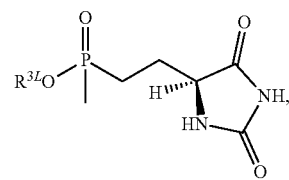

L-(III)

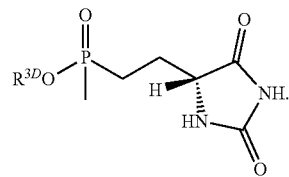

D-(III)

$R^{3L}$ is a radical selected from the above-mentioned formulae (VIII), (IX), (X), preferably selected from the formulae (VIII), (IX), more preferably $R^{3L}$ has formula (VIII).

When $R^{3L}$ is a radical of the formula (VIII), the radical $R^{3L}$ may be selected from the above-mentioned formulae L-(VIII) and D-(VIII), preferably L-(VIII).

When $R^{3L}$ is a radical of the formula (IX), the radical $R^{3L}$ may be selected from the above-mentioned formulae L-(IX) and D-(IX), preferably L-(IX).

When $R^{3L}$ is a radical of the formula (X), the radical $R^{3L}$ may be selected from the above-mentioned formulae L-(X) and D-(X), preferably L-(X).

$R^{3D}$ is a radical selected from the above-mentioned formulae (VIII), (IX), (X), preferably selected from the formulae (VIII), (IX), more preferably $R^{3D}$ has formula (VIII).

When $R^{3D}$ is a radical of the formula (VIII), the radical $R^{3D}$ may be selected from the above-mentioned formulae L-(VIII) and D-(VIII), preferably L-(VIII).

When $R^{3D}$ is a radical of the formula (IX), the radical $R^{3D}$ may be selected from the above-mentioned formulae L-(IX) and D-(IX), preferably L-(IX).

When $R^{3D}$ is a radical of the formula (X), the radical $R^{3D}$ may be selected from the above-mentioned formulae L-(X) and D-(X), preferably L-(X).

β.2) In a step (ii), the mixture $M_{IIIA}$ is subjected to a reaction with a hydantoinase $E_2$, which is more preferably as defined under item α.2), giving a composition $M_{II}$ comprising at least one compound according to formula L-(II) and optionally at least one compound according to formula D-(II), wherein L-(II) and D-(II) have the following formulae:

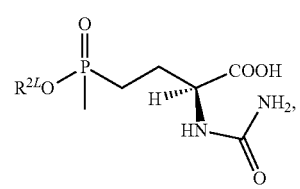

L-(II)

-continued

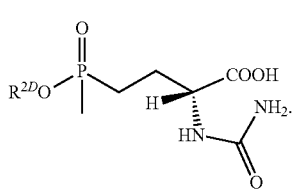

D-(II)

$R^{2L}$ is a radical selected from the above-mentioned formulae (VIII), (IX), (X), preferably selected from the formulae (IX), (X), more preferably $R^{2L}$ has formula (IX).

$R^{2D}$ is a radical selected from the above-mentioned formulae (VIII), (IX), (X), preferably selected from the formulae (IX), (X), more preferably $R^{2D}$ has formula (IX).

When $R^{2L}$ is a radical of the formula (VIII), the radical $R^{2L}$ may be selected from the above-mentioned formulae L-(VIII) and D-(VIII), preferably L-(VIII).

When $R^{2D}$ is a radical of the formula (VIII), the radical $R^{2D}$ may be selected from the above-mentioned formulae L-(VIII) and D-(VIII), preferably L-(VIII).

When $R^{2L}$ is a radical of the formula (IX), the radical $R^{2L}$ may be selected from the above-mentioned formulae L-(IX) and D-(IX), preferably L-(IX).

When $R^{2D}$ is a radical of the formula (IX), the radical $R^{2D}$ may be selected from the above-mentioned formulae L-(IX) and D-(IX), preferably L-(IX).

When $R^{2L}$ is a radical of the formula (X), the radical $R^{2L}$ may be selected from the above-mentioned formulae L-(X) and D-(X), preferably L-(X).

When $R^{2D}$ is a radical of the formula (X), the radical $R^{2D}$ may be selected from the above-mentioned formulae L-(X) and D-(X), preferably L-(X).

β.3) Then, in a further step (iii), $M_{II}$ is subjected to a reaction, which is catalyzed by an L-carbamoylase $E_1$, which is preferably as defined under item α.1), giving a $M_I$ comprising at least one compound according to formula L-(I) and optionally at least one compound according to formula D-(I), wherein D-(I) has the following formula:

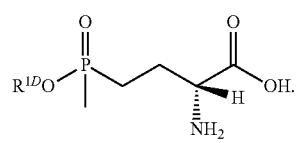

D-(I)

wherein $R^{1D}$ is a radical selected from the above-mentioned formulae (VIII), (IX), (X), preferably selected from the above-mentioned formulae (IX), (X), more preferably $R^{1D}$ has formula (X).

When $R^{1D}$ is a radical of the formula (VIII), the radical $R^{1D}$ may be selected from the above-mentioned formulae L-(VIII) and D-(VIII), preferably L-(VIII).

When $R^{1D}$ is a radical of the formula (IX), the radical $R^{1D}$ may be selected from the above-mentioned formulae L-(IX) and D-(IX), preferably L-(IX).

When $R^{1D}$ is a radical of the formula (X), the radical $R^{1D}$ may be selected from the above-mentioned formulae L-(X) and D-(X), preferably L-(X).

The method according to the second aspect of the invention is enantioselective, because $M_I$ comprises either only L-(I) or, in case $M_I$ comprises both stereoisomers L-(I) and D-(I), the molar ratio of L-(I) to D-(I) in $M_I$ is greater than the molar ratio of L-(III) to D-(III) in $M_{IIIA}$.

β.4) Furthermore, it was surprisingly found that the method for enantioselective production according to the second aspect of the invention can be further improved. Namely, in an optional step (i-B) which is carried out after step (i-A) [and which may be carried out before or concomitantly with steps (ii) and (iii), preferably concomitantly with steps (ii) and (iii)], at least a part of the compounds D-(III) comprised by the mixture $M_{IIIA}$ are reacted, preferably enzymatically catalyzed by a hydantoin racemase $E_3$, into L-(III), which is the isomer of D-(III), giving a composition $M_{IIIB}$ comprising L-(III) and optionally its isomer D-(III).

In case the reaction according to step (i-B) is enzymatically catalyzed, it is preferably catalyzed by a hydantoin racemase $E_3$.

The hydantoin racemase $E_3$ is preferably as defined under item α.3).

3. BRIEF DESCRIPTION OF THE DRAWINGS

Figure 2:
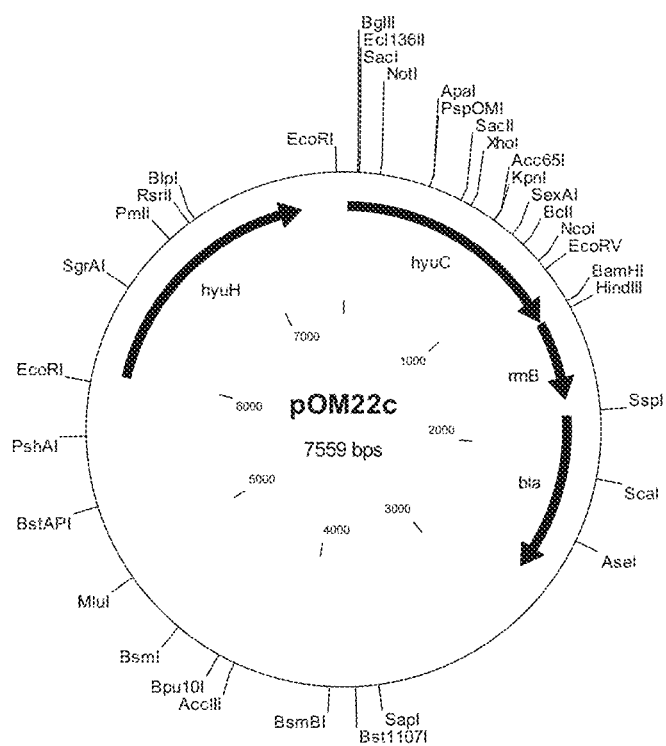

FIG. 1 shows the pOM21c plasmid map.
FIG. 2 shows the pOM22c plasmid map.

4. DETAILED DESCRIPTION OF THE INVENTION

4.1 Definitions

Any of the enzymes used according to any aspect of the present invention, may be an isolated enzyme. In particular, the enzymes used according to any aspect of the present invention may be used in an active state and in the presence of all cofactors, substrates, auxiliary and/or activating polypeptides or factors essential for its activity. Such factors may be metal ions such as $Mn^{2+}$ or $Co^{2+}$.

In particular, an enzyme according to the present application may be a carbamoylase $E_1$, a hydantoinase $E_2$, or a hydantoin racemase $E_3$.

"Enzymatically catalyzed" means that the respective reaction is catalyzed by an enzyme, which may be a carbamoylase $E_1$, a hydantoinase $E_2$, or a hydantoin racemase $E_3$.

The enzyme used according to any aspect of the present invention may be recombinant. The term "recombinant" as used herein, refers to a molecule or is encoded by such a molecule, particularly a polypeptide or nucleic acid that, as such, does not occur naturally but is the result of genetic engineering or refers to a cell that comprises a recombinant molecule. For example, a nucleic acid molecule is recombinant if it comprises a promoter functionally linked to a sequence encoding a catalytically active polypeptide and the promoter has been engineered such that the catalytically active polypeptide is overexpressed relative to the level of the polypeptide in the corresponding wild type cell that comprises the original unaltered nucleic acid molecule.

A "polypeptide" (one or more peptides) is a chain of chemical building blocks called amino acids that are linked together by chemical bonds called peptide bonds. A protein or polypeptide, including an enzyme, may be "native" or "wild-type", meaning that it occurs in nature or has the amino acid sequence of a native protein, respectively. These terms are sometimes used interchangeably. A polypeptide may or may not be glycosylated.

The term "overexpressed", as used herein, means that the respective polypeptide encoded or expressed is expressed at a level higher or at higher activity than would normally be found in the cell under identical conditions in the absence of genetic modifications carried out to increase the expression, for example in the respective wild type cell.

4.2 Methods to Obtain Enzymes

The enzymes that can be used in the method according to the present invention can be synthesized by methods that are known to the skilled person.

One approach, which is a preferred approach according to the invention, is to express the enzyme(s) in microorganism(s) such as *Escherichia coli* (="*E. coli*"), *Saccharomyces cerevisiae, Pichia pastoris*, and others, and to add the whole cells to the reactions as whole cell biocatalysts. Another approach is to express the enzyme(s), lyse the microorganisms, and add the cell lysate. Yet another approach is to purify, or partially purify, the enzyme(s) from a lysate and add pure or partially pure enzyme(s) to the reaction. If multiple enzymes are required for a reaction, the enzymes can be expressed in one or several microorganisms, including expressing all enzymes within a single microorganism.

For example, the skilled person can obtain the enzymes according to the invention by expression, in particular, overexpression, [hereinafter, "expression, in particular overexpression" is abbreviated as (over)expression", and "express, in particular overexpress" is abbreviated as (over) express"] of these enzymes in a cell and subsequent isolation thereof, e.g. as described in DE 100 31 999 A1. Episomal plasmids, for example, are employed for increasing the expression of the respective genes. In such plasmids, the nucleic acid molecule to be (over) expressed or encoding the polypeptide or enzyme to be (over) expressed may be placed under the control of a strong inducible promoter such as the lac promoter, located upstream of the gene. A promoter is a DNA sequence consisting of about 40 to 50 base pairs which constitutes the binding site for an RNA polymerase holoenzyme and the transcriptional start point (M. Pátek, J. Holátko, T. Busche, J. Kalinowski, J. Nešvera, Microbial Biotechnology 2013, 6, 103-117), whereby the strength of expression of the controlled polynucleotide or gene can be influenced. A "functional linkage" is obtained by the sequential arrangement of a promoter with a gene, which leads to a transcription of the gene.

Suitable strong promoters or methods of producing such promoters for increasing expression are known from the literature (e.g. S. Lisser & H. Margalit, Nucleic Acid Research 1993, 21, 1507-1516; M. Pátek and J. Nesvera in H. Yukawa and M Inui (eds.), *Corynebacterium glutamicum*, Microbiology Monographs 23, Springer Verlag Berlin Heidelberg 2013, 51-88; B. J. Eikmanns, E. Kleinertz, W. Liebl, H. Sahm, Gene 1991, 102, 93-98). For instance, native promoters may be optimized by altering the promoter sequence in the direction of known consensus sequences with respect to increasing the expression of the genes functionally linked to these promoters (M. Pátek, B. J. Eikmanns, J. Pátek, H. Sahm, Microbiology 1996, 142, 1297-1309; M. Pátek, J. Holátko, T. Busche, J. Kalinowski, J. Nešvera, Microbial Biotechnology 2013, 6, 103-117).

Constitutive promoters are also suitable for the (over) expression, in which the gene encoding the enzyme activity is expressed continuously under the control of the promoter such as, for example, the glucose dependent deo promoter. Chemically induced promoters are also suitable, such as tac, lac, rha or trp. The most widespread system for the induction of promoters is the lac operon of *E. coli*. In this case, either lactose or isopropyl β-D-thiogalactopyranoside (IPTG) is used as inducer. Also, systems using arabinose (e.g. the pBAD system) or rhamnose (e.g. *E. coli* KRX) are common as inducers. A system for physical induction is, for example, the temperature-induced cold shock promoter system based on the *E. coli* cspA promoter from Takara or Lambda PL and also osmotically inducible promoters, for example, osmB (e.g. WO 95/25785 A1).

Suitable plasmids or vectors are in principle all embodiments available for this purpose to the person skilled in the art. The state of the art describes standard plasmids that may be used for this purpose, for example the pET system of vectors exemplified by pET-3a or pET-26b (+) (commercially available from Novagen). Further plasmids and vectors can be taken, for example, pOM21 described in WO 2004/111227 A2, pOM22 described in WO 00/058449 A1 or pOM18 described in WO 2013/072486 A1 or from the brochures of the companies Novagen, Promega, New England Biolabs, Clontech or Gibco BRL. Further preferred plasmids and vectors can be found in: Glover, D. M. (1985) DNA cloning: a practical approach, Vol. I-III, IRL Press Ltd., Oxford; Rodriguez, R. L. and Denhardt, D. T (eds) (1988) Vectors: a survey of molecular cloning vectors and their uses, 179-204, Butterworth, Stoneham; Goeddel, D. V. (1990) Systems for heterologous gene expression, Methods Enzymol. 185, 3-7; Sambrook, J.; Fritsch, E. F. and Maniatis, T. (1989), Molecular cloning: a laboratory manual, 2nd ed., Cold Spring Harbor Laboratory Press, New York. Of these plasmids, pOM21 and pOM22 are preferred.

The plasmid vector, which contains the gene to be amplified, is then converted to the desired strain, e.g. by conjugation or transformation. The method of conjugation is described, for example, by A. Schäfer, J. Kalinowski, A. Pühler, Applied and Environmental Microbiology 1994, 60, 756-759. Methods for transformation are described, for example, in G. Thierbach, A. Schwarzer, A. Pühler, Applied Microbiology and Biotechnology 1988, 29, 356-362, L. K. Dunican & E. Shivnan, Bio/Technology 1989, 7, 1067-1070 and A. Tauch, O. Kirchner, L. Wehmeier, J. Kalinowski, A. Pühler, FEMS Microbiology Letters 1994, 123, 343-347. After homologous recombination by means of a "crossover" event, the resulting strain contains at least two copies of the gene concerned.

The desired enzyme can be isolated by disrupting cells which contain the desired activity in a manner known to the person skilled in the art, for example with the aid of a ball mill, a French press or of an ultrasonic disintegrator and subsequently separating off cells, cell debris and disruption aids, such as, for example, glass beads, by centrifugation for 10 minutes at 13,000 rpm and 4° C. Using the resulting cell-free crude extract, enzyme assays with subsequent LC-ESI-MS detection of the products can then be carried out. Alternatively, the enzyme can be enriched in the manner known to the person skilled in the art by chromatographic methods (such as nickel-nitrilotriacetic acid affinity chromatography, streptavidin affinity chromatography, gel filtration chromatography or ion-exchange chromatography) or else purified to homogeneity. Quantification of the enzyme can be performed by methods known to the person skilled in the art, for example by determination of the concentration of the respective polypeptide of the enzyme (e.g. carbamoylase, hydantoinase and racemase) in the obtained solution by SDS page and analysis of the respective bands via the software GelQuant® (BiochemLabSolutions).

Moreover, whether or not a nucleic acid or polypeptide is (over) expressed, may be determined by way of quantitative PCR reaction in the case of a nucleic acid molecule, SDS polyacrylamide electrophoreses, Western blotting or comparative activity assays in the case of a polypeptide. Genetic modifications may be directed to transcriptional, translational, and/or post-translational modifications that result in a change of enzyme activity and/or selectivity under selected and/or identified culture conditions.

4.3 Variants

In the context of the present invention, the term "variant" with respect to polypeptide sequences refers to a polypeptide sequence with a degree of identity to the reference sequence ("sequence identity") of at least 60%, preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.9%. In still further particular embodiments, the degree of identity is at least 98.0%, more preferably at least 98.2%, more preferably at least 98.4%, more preferably at least 98.6%, more preferably at least 98.8%, more preferably at least 99.0%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, or at least more preferably at least 99.9%.

It goes without saying that a "variant" of a certain polypeptide sequence is not identical to the polypeptide sequence.

Such variants may be prepared by introducing deletions, insertions, substitutions, or combinations thereof, in particular in amino acid sequences, as well as fusions comprising such macromolecules or variants thereof.

Modifications of amino acid residues of a given polypeptide sequence which lead to no significant modifications of the properties and function of the given polypeptide are known to those skilled in the art. Thus for example many amino acids can often be exchanged for one another without problems; examples of such suitable amino acid substitutions are: Ala by Ser; Arg by Lys; Asn by Gln or His; Asp by Glu; Cys by Ser; Gln by Asn; Glu by Asp; Gly by Pro; His by Asn or Gln; Ile by Leu or Val; Leu by Met or Val; Lys by Arg or Gin or Glu; Met by Leu or Ile; Phe by Met or Leu or Tyr; Ser by Thr; Thr by Ser; Trp by Tyr; Tyr by Trp or Phe; Val by Ile or Leu. It is also known that modifications, particularly at the N- or C-terminus of a polypeptide in the form of for example amino acid insertions or deletions, often exert no significant influence on the function of the polypeptide.

In line with this, preferable variants according to the invention of any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, respectively, have a polypeptide sequence that comprises the complete polypeptide sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, respectively, or at least the amino acids of the respective sequence SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26 that are essential for the function, for example the catalytic activity of a protein, or the fold or structure of the protein. The other amino acids may be deleted, substituted or replaced by insertions or essential amino acids are replaced in a conservative manner to the effect that the activity of the enzyme, in particular the L-carbamoylase (SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9), hydantoinase (SEQ ID NO: 10, SEQ ID NO: 11, SEQ ID NO: 12, SEQ ID NO: 13, SEQ ID NO: 14, SEQ ID NO: 15, SEQ ID NO: 16), hydantoin racemase (SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26), is preserved.

3.4 Sequence Identity

The person skilled in the art is aware that various computer programs are available for the calculation of similarity or identity between two nucleotide or polypeptide sequences.

Preferred methods for determining the sequence identity initially generate the greatest alignment between the sequences to be compared. Computer programs for determining the sequence identity include, but are not limited to, the GCG program package including GAP [J. Deveroy et al., Nucleic Acid Research 1984, 12, page 387, Genetics Computer Group University of Wisconsin, Medicine (WI)], and BLASTP, BLASTN and FASTA (S. Altschul et al., Journal of Molecular Biology 1990, 215, 403-410). The BLAST program can be obtained from the National Center for Biotechnology Information (NCBI) and from other sources (BLAST Handbook, S. Altschul et al., NCBI NLM NIH Bethesda ND 22894; S. Altschul et al., above).

For instance, the percentage identity between two polypeptide sequences can be determined by the algorithm developed by S. B. Needleman & C. D. Wunsch, J. Mol. Biol. 1970, 48, 443-453, which has been integrated into the GAP program in the GCG software package, using either a BLOSUM62 matrix or a PAM250 matrix, a gap weight of 16, 14, 12, 10, 8, 6 or 4 and a length weight of 1, 2, 3, 4, 5 or 6. The person skilled in the art will recognize that the use of different parameters will lead to slightly different results, but that the percentage identity between two polypeptide overall will not be significantly different. The BLOSUM62 matrix is typically used applying the default settings (gap weight: 12, length weight: 1).

In the context of the present invention, a sequence identity of 60% according to the above algorithm means 60% homology. The same applies to higher sequence identities.

Most preferably, the degree of identity between sequences is determined in the context of the present invention by the programme "Needle" using the substitution matrix BLOSUM62, the gap opening penalty of 10, and the gap extension penalty of 0.5. The Needle program implements the global alignment algorithm described in S. B. Needleman & C. D. Wunsch, J. Mol. Biol. 1970, 48, 443-453. The substitution matrix used according to the present invention is BLOSUM62, gap opening penalty is 10, and gap extension penalty is 0.5. The preferred version used in the context of this invention is the one presented by F. Madeira, Y. M. Park, J. Lee, N. Buso, T. Gur, N. Madhusoodanan, P. Basutkar, A. R. N. Tivey, S. C. Potter, R. D. Finn, Nucleic Acids Research 2019, 47, W636-W641, Web Server issue (preferred version accessible online on Mar. 4, 2022 via https://www.ebi.ac.uk/Tools/psa/emboss_needle/).

In a particular embodiment, the percentage of identity of an amino acid sequence of a polypeptide with, or to, a reference polypeptide sequence is determined by
i) aligning the two amino acid sequences using the Needle program, with the BLOSUM62 substitution matrix, a gap opening penalty of 10, and a gap extension penalty of 0.5;
ii) counting the number of exact matches in the alignment;
iii) dividing the number of exact matches by the length of the longest of the two amino acid sequences, and
iv) converting the result of the division of iii) into percentage.

4.5 First Aspect: Method for Production of a Glufosinate P-Ester

4.5.1 Step (c)

4.5.1.1 Enzymatic Catalysis of Step (c)

The present invention relates in a first aspect to a method for the production of an L-glufosinate P-ester according to formula L-(I):

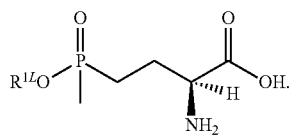

L-(I)

The method according to the first aspect of the invention comprises a step (c).

In step (c), a compound according to formula L-(II) is reacted to give a compound according to formula L-(I). Formula L-(II) has the following formula:

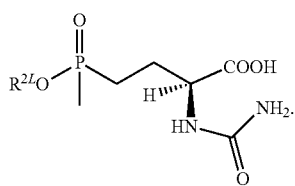

L-(II)

The reaction according step (c) is enzymatically catalyzed, namely it is catalyzed by a carbamoylase $E_1$.

$R^{1L}$ is a radical selected from the formulae (VIII), (IX), (X), preferably selected from the formulae (IX), (X), more preferably $R^{1L}$ has formula (X).

$R^{2L}$ is a radical selected from the formulae (VIII), (IX), (X), preferably selected from the formulae (IX), (X), more preferably $R^{2L}$ has formula (X).

Formulae (VIII), (IX), (X) are as follows:

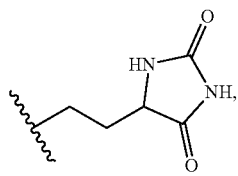

(VIII)

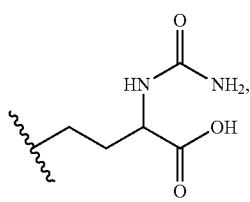

(IX)

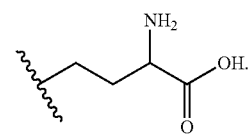

(X)

When $R^{1L}$ is a radical of the formula (VIII), the radical $R^{1L}$ may be selected from the formulae L-(VIII) and D-(VIII), preferably L-(VIII).

When $R^{1L}$ is a radical of the formula (IX), the radical $R^{1L}$ may be selected from the formulae L-(IX) and D-(IX), preferably L-(IX).

When $R^{1L}$ is a radical of the formula (X), the radical $R^{1L}$ may be selected from the formulae L-(X) and D-(X), preferably L-(X).

When $R^{2L}$ is a radical of the formula (VIII), the radical $R^{2L}$ may be selected from the formulae L-(VIII) and D-(VIII), preferably L-(VIII).

When $R^{2L}$ is a radical of the formula (IX), the radical $R^{2L}$ may be selected from the formulae L-(IX) and D-(IX), preferably L-(IX).

When $R^{2L}$ is a radical of the formula (X), the radical $R^{2L}$ may be selected from the formulae L-(X) and D-(X), preferably L-(X).

Formulae L-(VIII), D-(VIII), L-(IX), D-(IX), L-(X), and D-(X) are as follows:

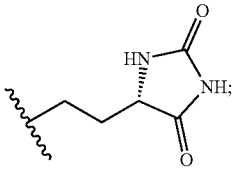

L-(VIII)

-continued

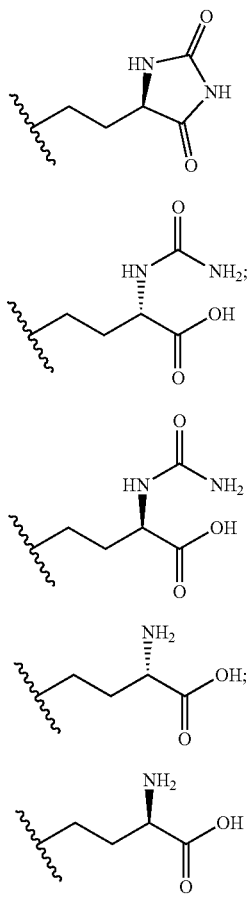

D-(VIII)

L-(IX)

D-(IX)

L-(X)

D-(X)

4.5.1.2 Enantioselective and Enantiospecific Catalysis of Step (c)

Step (c) of the method according to the first aspect of the present invention is preferably L-enantioselective, even more preferably L-enantiospecific.

In such a preferred embodiment, L-(II) is in particular employed in step (c) as a mixture $M_{II}$ comprising at least one compound L-(II) and at least one compound D-(II), wherein D-(II) has the following formula:

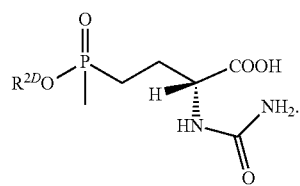

D-(II)

$R^{2D}$ is a radical selected from the formulae (VIII), (IX), (X), preferably selected from the formulae (IX), (X), more preferably $R^{2D}$ has formula (X).

When $R^{2D}$ is a radical of the formula (VIII), the radical $R^{2D}$ may be selected from the formulae L-(VIII) and D-(VIII), preferably L-(VIII).

When $R^{2D}$ is a radical of the formula (IX), the radical $R^{2D}$ may be selected from the formulae L-(IX) and D-(IX), preferably L-(IX).

When $R^{2D}$ is a radical of the formula (X), the radical $R^{2D}$ may be selected from the formulae L-(X) and D-(X), preferably L-(X).

Mixture $M_{II}$ preferably comprises at least one compound L-(II) and at least one compound D-(II), wherein $R^{2L}=R^{2D}$.

For such mixtures Mu, it may be observed that the at least one compound D-(II) undergoes a reaction according to step (c)*, i.e. parallel to step (c). Namely, in the reaction according to step (c)*, the at least one compound D-(II) in mixture $M_{II}$ is reacted to give a compound according to formula D-(I):

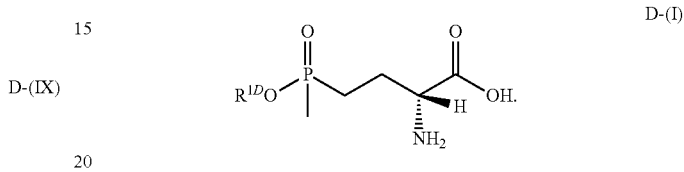

D-(I)

$R^{1D}$ is a radical selected from the above-mentioned formulae (VIII), (IX), (X), preferably selected from the above-mentioned formulae (IX), (X), more preferably $R^{1D}$ has formula (X).

When $R^{1D}$ is a radical of the formula (VIII), the radical $R^{1D}$ may be selected from the above-mentioned formulae L-(VIII) and D-(VIII), preferably L-(VIII).

When $R^{1D}$ is a radical of the formula (IX), the radical $R^{1D}$ may be selected from the above-mentioned formulae L-(IX) and D-(IX), preferably L-(IX).

When $R^{1D}$ is a radical of the formula (X), the radical $R^{1D}$ may be selected from the above-mentioned formulae L-(X) and D-(X), preferably L-(X).

In case that step (c) is "L-enantioselective", this means that in case a mixture $M_{II}$ is employed in step (c), then there is
- either no reaction according to step (c)* of any compound according to formula D-(II) to a compound according to D-(I) in the mixture $M_{II}$ or,
- in case there is a reaction according to step (c)*, then there is at least one pair of compounds D-(II)(II)*/L-(II)(II)* in the mixture $M_{III}$, for which the reaction according to step (c)* of D-(II)(II)* to give D-(I)(II)*, is lesser than the rate of the reaction according to step (c) of L-(II)(II)* to give L-(I)(II)*.

D-(II)(II)* is a compound according to formula D-(II), and L-(II)(II)* is a compound according to formula L-(II), wherein the radical $R^{2L}$ in L-(II)(II)* and the radical $R^{2D}$ in D-(II)(II)* are identical.

D-(I)(II)* is a compound according to formula D-(I), and L-(I)(II)* is a compound according to formula L-(I), wherein the radical $R^{2L}$ in L-(I)(II)* and the radical $R^{2D}$ in D-(I) (II)* are identical.

Preferably, the radical $R^{2L}$ in L-(II)(II)* and the radical $R^{1L}$ in L-(I)(II)* are identical. Preferably, the radical $R^{2D}$ in D-(II)(II)* and the radical $R^{1D}$ in D-(I)(II)* are identical.

Step (c) is "L-enantiospecific", if the rate of reaction according to step (c)* is essentially zero, i.e. there is no reaction according to step (c)* of any compound according to formula D-(II) to a compound according to D-(I) in the mixture $M_{II}$.

In a preferred embodiment, the molar ratio of all compounds according to formula L-(II) in the mixture $M_{II}$ to all compounds according to formula D-(II) in the mixture $M_{II}$ is essentially 1:1.

In other preferred embodiments, the molar ratio of all compounds according to formula L-(II) in the mixture $M_{II}$ to all compounds according to formula D-(II) in the mixture $M_{II}$ is in the range of from 3:2 to 1:99, more preferably in the range of from 1.01:1 to 1:99, more preferably in the range of from 1:1 to 1:99, more preferably in the range of from 1:1.01 to 1:99, more preferably in the range of from 1:1.01 to 1:9, more preferably in the range of from 1:1.01 to 1:8, more preferably in the range of from 1:1.01 to 1:3.

Alternatively, D-(II) is comprised in an excess to L-(II) in mixture Mu, meaning that, while at least one compound according to formula L-(II) is present in the mixture Mu, the molar ratio of all compounds according to formula L-(II) in the mixture $M_{II}$ to all compounds according to formula D-(II) in the mixture $M_{II}$ is <1:1, preferably <0.9:1, more preferably <0.75:1, more preferably <0.5:1, more preferably <0.2:1, more preferably <0.1:1, more preferably <0.01:1.

Step (c) is in particular L-enantioselective, if it is catalyzed by an L-carbamoylase $E_1$, which may be determined by the skilled person as set forth under 4.5.4.3.

In case step (c) is L-enantioselective with respect to a given pair of compounds D-(II)(II)*/L-(II)(II)*, the reaction according to step (c) of L-(II)(II)* to give L-(I)(II)* proceeds preferably at a reaction rate that is at least 2 times greater, preferably at least 10 times greater, more preferably at least 100 times greater, even more preferably at least 103 times greater, even more preferably at least 104 times greater, even more preferably at least 105 times greater than the reaction rate at which step (c)* of D-(II)(II)* to give D-(I)(II)* proceeds.

To quantify for a given pair of compounds D-(II)(II)*/L-(II)(II)* the factor at which the reaction rate of step (c) proceeds compared to the reaction rate of step (c)*, the following test may be carried out:

(1) An equimolar mixture [molar ratio of the two compounds L-(II)(II)* and D-(II)(II)* is 1:1] is subjected to the respective reactions conditions and the development of the two products L-(I)(II)* and D-(I)(II)* is monitored over time (e.g. by LC-MS as set forth under item 5.4).

(2) When $n_{LI10}$=10 mol-% of the initially employed L-(II)(II)* has reacted to the product L-(I)(II)*, the amount of D-(I)(II)* that was formed by reaction from D-(II)(II)* [in mol-% relative to the initially employed D-(II)+] is measured (=$n_{DI10}$).

(3) The ratio of $n_{LI10}/n_{DI10}$=10/$n_{DI10}$ gives the factor at which the reaction rate of step (c) proceeds compared to the reaction rate of step (c)* for the given pair of compounds D-(II)(II)*/L-(II)(II)*.

If $n_{LI10}/n_{DI10}$>1, the reaction rate of step (c) is greater than the reaction rate of step (c)* for the given pair of compounds D-(II)(II)*/L-(II)(II)*.

If $n_{LI10}/n_{DI10}$<1, the reaction rate of step (c) is lesser than the reaction rate of step (c)* for the given pair of compounds D-(II)(II)*/L-(II)(II)*.

If $n_{LI10}/n_{DI10}$=1, the reaction rates of steps (c) and (c)* are the same for the given pair of compounds D-(II)(II)*/L-(II)(II)*.

4.5.2 Carbamoylases

The reaction according to step (c) of the method according to the first aspect of the invention is catalyzed by a carbamoylase $E_1$.

Namely, it was surprisingly found that carbamoylases accept compounds of formula L-(II) as substrates and convert them to products L-(I), and hence can be used to catalyze the reaction according to step (c). This finding is of high scientific and economic value, as it opens new synthetic routes based on new starting materials for the production of L-glufosinate P-esters and L-glufosinate. Even more surprisingly, it was found that L-glufosinate carbamoylate, i.e. the compound according to L-(II), in which R=H, does not undergo reaction by carbamoylases to give L-glufosinate.

In nature, carbamoylases generally catalyze the following reaction <1>, wherein $R^X$ may be an organic residue, e.g. a side chain of one of the naturally occurring amino acids.

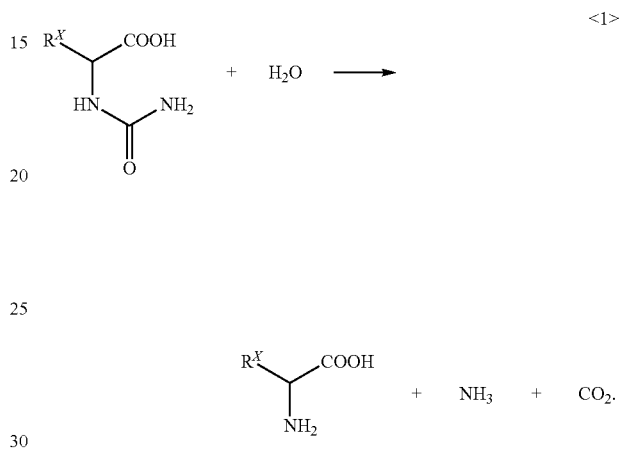

<1>

It was now surprisingly found that carbamoylases also accept substrates in which $R^X=R^Y=$

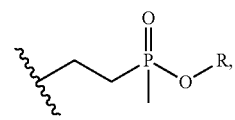

wherein $R=R^{2L}$.

Surprisingly, they do not accept substrates in which $R^X=R^Y=$

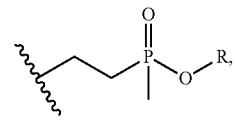

wherein R=H.

In the context of the present invention, a "carbamoylase $E_1$" is a carbamoylase that catalyzes the following reaction <1A> of a carbamoyl substrate SL to the respective amino acid product $P_L$, wherein $R^X=R^Y=$

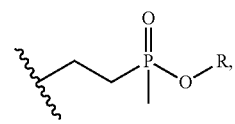

wherein R=$R^{2L}$:

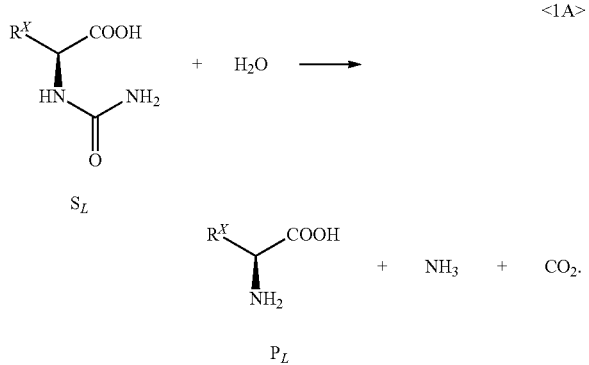

<1A>

In particular, the carbamoylase $E_1$ is a "L-carbamolyase", i.e. it has a greater catalytic activity for reaction <1A> than for reaction <1B>, wherein $R^X$ in the substrate Sp in the reaction <1B> and $R^X$ in the substrate SL in the reaction <1A> are identical, and $R^X$=$R^Y$=

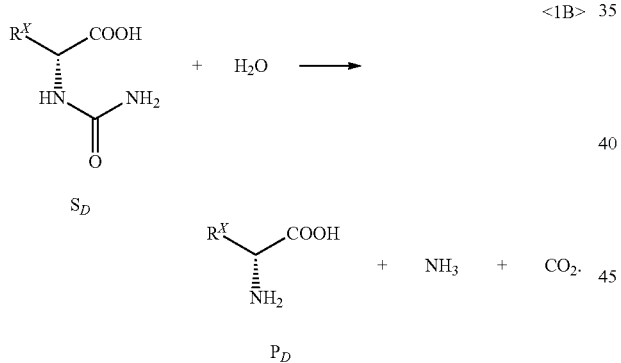

wherein R=$R^{2L}$

<1B>

As an L-carbamoylase has a higher catalytic activity for reaction <1A> than for reaction <1B>, it is "L-enantioselective". An L-carbamoylase that has no catalytic activity for reaction <1B> and thus only has catalytic activity for reaction <1A> is "L-enantiospecific".

A "D-carbamoylase" is defined as a carbamoylase which is "D-enantioselective", i.e. it has a higher catalytic activity for reaction <1B> than for reaction <1A>. A D-carbamoylase that does not catalyze reaction <1A> and thus only has catalytic activity for reaction <1B> is "D-enantiospecific".

A carbamoylase which has the same catalytic activity for reaction <1B> as for reaction <1A>, is referred to as "non-enantioselective carbamoylase".

For determination whether a carbamoylase may be denoted as "L-carbamoylase", "D-carbamoylase" or "non-enantioselective carbamoylase" in the context of the present invention, the procedure according to Assay B (item 4.5.4) may preferably be used.

The carbamoylase $E_1$, in particular the L-carbamoylase $E_1$, that may be used in step (c) of the method according to the first aspect of the invention may originate from *Achromobacter* sp., in particular *Achromobacter xylosoxidans*; *Agrobacterium* sp., in particular *Agrobacterium tumefaciens*; *Arthrobacter* sp., in particular *Arthrobacter crystallopoietes, Arthrobacter aurescens, Arthrobacter* sp. BT801; *Bacillus* sp., in particular *Bacillus fordii*; *Blastobacter* sp.; *Bradyrhizobium* sp., in particular *Bradyrhizobium japonicum*; *Brevibacillus* sp., in particular *Brevibacillus reuszeri*; *Comamonas* sp.; *Ensifer* sp., in particular *Ensifer adhaerens*; *Flavobacterium* sp. *Geobacillus* sp., in particular *Geobacillus kaustophilus, Geobacillus stearothermophilus*; *Microbacterium* sp., in particular *Microbacterium liquefaciens* strain AJ3912; *Paenarthrobacter* sp., in particular *Paenarthrobacter aurescens*; *Pasteurella* sp.; *Pseudomonas* sp.; *Ralstonia* sp., in particular *Ralstonia pickettii*; *Sinorhizobium* sp., in particular *Sinorhizobium meliloti*.

An L-carbamoylase $E_1$ suitable for the method according to the present invention may be the enzyme HyuC, which originates from *Arthrobacter*. Other enzymes are AmaB, AtcC, Inc, SinmeB_2280.

WO 01/23582 A1 discloses an example of an enzyme having carbamoylase activity according to the invention.

The carbamoylase $E_1$ that may be used in step (c) of the method according to the present invention may be an L-carbamoylase categorized in the EC class EC 3.5.1.87.

L-carbamoylase enzymes are for example described by J. Ogawa, H. Miyake, S. Shimizu, *Appl. Microbiol. Biotechnol.* 1995 43, 1039-1043 and in WO 01/23582 A1.

A L-carbamoylase $E_1$ that may preferably be used in step (c) according to the first aspect of the invention may originate from *Arthrobacter* sp., in particular *Arthrobacter crystallopoietes, Arthrobacter aurescens, Arthrobacter* sp. BT801, *Arthrobacter aurescens* DSM 3747; *Bacillus* sp., in particular *Bacillus fordii*; *Geobacillus* sp., in particular *Geobacillus stearothermophilus, Geobacillus kaustophilus*; *Microbacterium* sp., in particular *Microbacterium liquefaciens* strain AJ3912; *Paenarthrobacter* sp., in particular *Paenarthrobacter aurescens*; *Pseudomonas* sp., in particular *Pseudomonas* sp. QR-101; *Sinorhizobium* sp., in particular *Sinorhizobium meliloti*. Even more preferably, the L-carbamoylase $E_1$ that may preferably be used in step (c) according to the first aspect of the invention may originate from *Arthrobacter* sp., in particular *Arthrobacter crystallopoietes, Arthrobacter aurescens, Arthrobacter* sp. BT801, *Arthrobacter aurescens* DSM 3747, most preferably from *Arthrobacter aurescens* DSM 3747.

The respective sequences can be derived from databases such as the Braunschweig Enzyme Database (BRENDA, Germany, available under www.brenda-enzymes.org/index.php), the National Center for Biotechnological Information (NCBI, available under www.ncbi.nlm.nih.gov/) or the Kyoto Encyclopedia of Genes and Genomes (KEGG, Japan, available under www.genome.jp/kegg/).

The following table 1 gives preferred examples for polypeptide sequences of L-carbamoylases $E_1$ that may be preferably used in step (c) of the method according to the first aspect of the invention. The genes encoding the respective L-carbamoylase $E_1$ and the respective accession code are indicated as far as known.

TABLE 1

L-Carbamoylases (EC 3.5.1.87)

| Strain | Gene name | GenBank/UniProt accession | SEQ ID NO: of the polypeptide |
|---|---|---|---|
| *Arthrobacter aurescens* DSM 3747 | hyuC | | SEQ ID NO: 1 |
| *Geobacillus stearothermophilus* | amaB | Q53389 | SEQ ID NO: 2 |
| *Pseudomonas* sp. QR-101 | atcC | H9B8T5 | SEQ ID NO: 3 |
| *Geobacillus kaustophilus* | lnc | Q8GQG5 | SEQ ID NO: 4 |
| *Paenarthrobacter aurescens* | hyuC | Q9F464 | SEQ ID NO: 5 |
| *Sinorhizobium meliloti* | SinmeB_2280 | A0A0E0UEY4 | SEQ ID NO: 6 |
| *Bacillus fordii* strain MH602 | not assigned | ABL14248 | SEQ ID NO: 7 |
| *Arthrobacter* sp. BT801 | hyuC | AAL55413 | SEQ ID NO: 8 |
| *Microbacterium liquefaciens* strain AJ3912 | not assigned | | SEQ ID NO: 9 |

In a preferred embodiment of the method according to the first aspect of the present invention, the reaction according to step (c) is catalyzed by an L-carbamoylases $E_1$, wherein the polypeptide sequence of $E_1$ is selected from the group consisting of SEQ ID NO: 1 and variants thereof, SEQ ID NO: 2 and variants thereof, SEQ ID NO: 3 and variants thereof, SEQ ID NO: 4 and variants thereof, SEQ ID NO: 5 and variants thereof, SEQ ID NO: 6 and variants thereof, SEQ ID NO: 7 and variants thereof, SEQ ID NO: 8 and variants thereof, SEQ ID NO: 9 and variants thereof, preferably SEQ ID NO: 1 and variants thereof.

4.5.3 Assays $A_L$ and $A_D$ for Determining Carbamoylase Activity

The skilled person is aware of carbamoylases, in particular L-carbamoylases, that may be used in step (c) of the method according to the first aspect of the invention.

In particular, Assay $A_L$, described in the following, may be used to determine carbamolyase and L-carbamoylase activity of a given enzyme $E_X$ and may advantageously be used according to the invention to determine carbamoylase and L-carbamoylase activity in variants of SEQ ID NO: 1, variants of SEQ ID NO: 2, variants of SEQ ID NO: 3, variants of SEQ ID NO: 4, variants of SEQ ID NO: 5, variants of SEQ ID NO: 6, variants of SEQ ID NO: 7, variants of SEQ ID NO: 8, variants of SEQ ID NO: 9.

For comparative reasons, Assay $A_D$ may be used to determine D-carbamoylase activity of a given enzyme $E_X$.

For the purpose of Assay $A_L$ and Assay $A_D$, the molar mass of the enzyme $E_X$ to be tested is calculated as the molar mass of the polypeptide sequence of $E_X$.

Moreover, a substrate according to formula L-(II), wherein $R^{2L}$=n-butyl, is used in Assay $A_L$ so that there is only one chiral carbon atom in the substrate. The compound according to formula L-(II), wherein $R^{2L}$=n-butyl, is denoted as "L-(II)+".

A product according to formula L-(I), wherein $R^{1L}$=n-butyl, is detected in Assay $A_L$.

The compound according to formula L-(I), wherein $R^{1L}$=n-butyl, is denoted as "L-(I)(II)*".

Moreover, a substrate according to formula D-(II), wherein $R^{2D}$=n-butyl, is used in Assay $A_D$ so that there is only one chiral carbon atom in the substrate. The compound according to formula D-(II), wherein $R^{2D}$=n-butyl, is denoted as" D-(II)(II)*".

A product according to formula D-(I), wherein $R^{1D}$=n-butyl, is detected in Assay $A_D$.

The compound according to formula D-(I), wherein $R^{1D}$=n-butyl, is denoted as "D-(I)(II)*".

4.5.3.1 Assay $A_L$:

To 0.9 ml of an aqueous reaction solution (phosphate buffer, pH 7.2, 10 mM $MnCl_2$), containing 50 mM of a compound according to formula L-(II)(II)* are added 400 nmol of $E_X$ in 0.1 ml aqueous phosphate buffer (pH 7.2, 10 mM $MnCl_2$). The resulting solution is incubated at 25° C., and the pH is held at pH 7.2 by addition of 0.5 M NaOH. After 300 minutes, the reaction is stopped by addition of 2 M HCl to achieve a pH of 2.5, and the molar amount of the respective compound according to formula L-(I)(II)* is determined. L-(I)(II)* may be detected by the LC-MS method as described in the example section (item 5.4) for detection of LGA.

4.5.3.2 Assay $A_D$:

To 0.9 ml of an aqueous reaction solution (phosphate buffer, pH 7.2, 10 mM $MnCl_2$), containing 50 mM of a compound according to formula D-(II)(II)* are added 400 nmol of $E_X$ in 0.1 ml aqueous phosphate buffer (pH 7.2, 10 mM $MnCl_2$). The resulting solution is incubated at 25° C., and the pH is held at pH 7.2 by addition of 0.5 M NaOH. After 300 minutes, the reaction is stopped by addition of 2 M HCl to achieve a pH of 2.5, and the molar amount of the respective compound according to formula D-(I)(II)* is determined. D-(I)(II)* may be detected by the LC-MS method described in the example section (item 5.4) for detection of LGA.

4.5.4 Assay B for Identifying Carbamoylases, L-Carbamoylases, D-Carbamoylases, L- and D-Enantiospecificity The carbamoylase $E_1$ according to the invention is preferably an L-carbamoylase, more preferably L-enantiospecific.

Whether a given enzyme $E_X$ may be considered a carbamoylase $E_1$, in particular an L-carbamoylase, may be determined in the context of the present invention by the following Assay B.

4.5.4.1 Assay B:

B-1. Firstly, Assay $A_L$ as set forth under item 4.5.3.1 is conducted, and the obtained molar amount of the compound of the formula L-(I)(II)* is determined according to Assay $A_L$.

B-2. Secondly, Assay $A_D$ as set forth under item 4.5.3.2 is conducted, and the obtained molar amount of the compound of the formula D-(I)(II)* is determined according to Assay $A_D$.

B-3. Then, step B-1 is repeated, except that instead of the addition of 400 nmol $E_x$ in 0.1 ml aqueous phosphate buffer (pH 7.2, 10 mM $MnCl_2$), 0.1 ml aqueous phosphate buffer (pH 7.2, 10 mM $MnCl_2$) without $E_x$ is added.

B-4. Then, step B-2 is repeated, except that instead of the addition of 400 nmol $E_x$ in 0.1 ml aqueous phosphate buffer (pH 7.2, 10 mM $MnCl_2$), 0.1 ml aqueous phosphate buffer (pH 7.2, 10 mM $MnCl_2$) without $E_x$ is added.

4.5.4.2 Carbamoylase Activity

If the molar amount of the compound of the formula L-(I)(II)* that is determined in step B-1, is greater than the molar amount of the compound of the formula L-(I)(II)* that is determined in step B-3, then $E_x$ is deemed to have carbamoylase activity, and hence may be considered a carbamoylase $E_1$ in the context of the invention.

4.5.4.3 L-Carbamoylase Activity 4.5.4.3.1 L-Carbamoylases (i) If the molar amount of the compound of formula L-(I)(II)* that is determined in step B-1, is greater than the molar amount of the compound of formula L-(I)(II)* that is determined in step B-3, and (ii) if the molar amount of the compound of formula D-(I)(II)* that is determined in step B-2, is greater than or the same as the molar amount of the compound of formula D-(I)(II)* that is determined in step B-4, and (iii) if, in addition, the molar amount of the compound of formula of L-(I)(II)* that is determined in step B-1 is greater than the molar amount of the compound of formula of D-(I)(II)* that is determined in step B-2, then $E_x$ is deemed to have L-carbamoylase activity, and hence may be considered an L-carbamoylase in the context of the invention. In this case, $E_x$ is deemed to be "L-enantioselective" in the context of the invention.

For the sake of clarity, it is pointed out that condition (iii) is automatically fulfilled in those cases in which the molar amount of the compound of formula D-(I)(II)* that is determined in step B-2, is the same as the molar amount of the compound of formula D-(I)(II)* that is determined in step B-4.

(i) If the molar amount of the compound of formula L-(I)(II)* that is determined in step B-1, is greater than the molar amount of the compound of formula L-(I)(II)* that is determined in step B-3, and (ii) if the molar amount of the compound of formula D-(I)(II)* that is determined in step B-2 is the same as the molar amount of the compound of formula D-(I)(II)* that is determined in step B-4, then $E_x$ is deemed to have L-carbamoylase activity, and hence may be considered an L-carbamoylase in the context of the invention. In this case, $E_x$ is not only "L-enantioselective", but also "L-enantiospecific" in the context of the invention.

For L-carbamyolases $E_x$ that are not L-enantiospecific, the L-enantioselectivity may then be quantified by dividing the molar amount of the compound of formula L-(I)(II)* that is determined in step B-1, by the molar amount of the compound of formula D-(I)(II)* that is determined in step B-2, and then multiplying the obtained value by 100, giving the L-enantioselectivity of $E_X$ in %.

4.5.4.3.2 D-Carbamoylases (i) If the molar amount of the compound of formula L-(I)(II)* that is determined in step B-1, is greater than or the same as the molar amount of the compound of formula L-(I)(II)* that is determined in step B-3, and (ii) if the molar amount of the compound of formula D-(I)(II)* that is determined in step B-2, is greater than the molar amount of the compound of formula D-(I)(II)* that is determined in step B-4, and (iii) if, in addition, the molar amount of the compound of formula D-(I)(II)* that is determined in step B-2 is greater than the molar amount of the compound of formula L-(I)(II)* that is determined in step B-1, then $E_x$ is deemed to have D-carbamoylase activity, and hence may be considered a D-carbamoylase. In this case, $E_x$ is "D-enantioselective" in the context of the invention.

For the sake of clarity it is pointed out that condition (iii) is automatically fulfilled in those cases in which the molar amount of the compound of formula L-(I)(II)* that is determined in step B-1 is the same as the molar amount of the compound of formula L-(I)(II)* that is determined in step B-3.

(i) If the molar amount of the compound of formula L-(I)(II)* that is determined in step B-1, is the same as the molar amount of the compound of formula L-(I)(II)* that is determined in step B-3, and (ii) if the molar amount of the compound of formula D-(I)(II)* that is determined in step B-2, is greater than the molar amount of the compound of formula D-(I)(II)* that is determined in step B-4, then $E_x$ is deemed to have D-carbamoylase activity, and hence may be considered to be a D-carbamoylase. In this case, $E_x$ is not only "D-enantioselective", but also "D-enantiospecific" in the context of the invention.

For D-carbamoylases $E_x$, that are not D-enantiospecific, the D-enantioselectivity may then be quantified by dividing the molar amount of the compound of formula D-(I)(II)* that is determined in step B-2 by the molar amount of the compound of formula L-(I)(II)* that is determined in step B-1 and then multiplying the obtained value by 100, giving the D-enantioselectivity of $E_x$ in %.

4.5.4.3.3 Non-Enantioselective Carbamoylases (i) If the molar amount of the compound of formula L-(I)(II)* that is determined in step B-1, is greater than the molar amount of the compound of formula L-(I)(II)* that is determined in step B-3, and (ii) if the molar amount of the compound of formula D-(I)(II)* that is determined in step B-2 is greater than the molar amount of the compound of formula D-(I)(II)* that is determined in step B-4, and (iii) if, in addition, the molar amount of the compound of formula D-(I)(II)* that is determined in step B-2 is the same as the molar amount of the compound of formula L-(I)(II)* that is determined in step B-1, then $E_x$ is deemed to be a non-enantioselective carbamoylase in the context of the invention. In this case, $E_x$ is "non-enantioselective".

4.5.5 Assay C for Identifying Preferred Carbamoylase Variants of SEQ ID NOs: 1-9

4.5.5.1 L- and D-Enantioselective Carbamoylase Variants

An enzyme, the polypeptide sequence of which is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 has carbamoylase, and L-carbamoylase activity.

In a preferred embodiment of the method according to the first aspect of the invention, the polypeptide sequence of the L-carbamoylase $E_1$ is selected from the group consisting of SEQ ID NO: 1 and variants thereof, SEQ ID NO: 2 and variants thereof, SEQ ID NO: 3 and variants thereof, SEQ ID NO: 4, and variants thereof, SEQ ID NO: 5 and variants thereof, SEQ ID NO: 6 and variants thereof, SEQ ID NO: 7, and variants thereof, SEQ ID NO: 8 and variants thereof, SEQ ID NO: 9 and variants thereof, more preferably SEQ ID NO: 1 and variants thereof.

The term "variant" is defined under item 4.3.

In the context of the invention, an enzyme $E_1$, the polypeptide sequence of which is a variant of one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 has carbamoylase activity, preferably L-carbamoylase activity, more preferably is L-enantiospecific.

Whether a given enzyme $E_X$, the polypeptide sequence of which is a variant of one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, has carbamoylase activity, L carbamoylase activity and/or is L-enantiospecific may be determined as set forth under items 4.5.4.2 and 4.5.4.3.1, respectively.

The carbamoylase activity of a given L-carbamoylase $E_{1V}$, the polypeptide sequence of which is a variant of one of one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, relative to the carbamoylase activity of an L-carbamoylase $E_{1S}$, wherein the polypeptide sequence of $E_{1S}$ is selected from of one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, may be quantified in the context of the present invention by the following Assay C:

4.5.5.2 Assay C

C-1 Assay $A_L$ as set forth under item 4.5.3.1 is conducted, wherein $E_{1S}$ is the enzyme to be tested. The obtained molar amount of the compound according to formula L-(I)(II)* is determined according to Assay $A_L$.

C-2 Step C-1 is repeated, except that, instead of $E_{1S}$, $E_{1V}$ is used as the enzyme to be tested.

C-3. Then, the molar amount of the compound according to formula L-(I)(II)* that is determined in step C-2, is divided by the molar amount of the compound according to formula L-(I)(II)* that is determined in step C-1, and the obtained ratio is multiplied by 100, giving the carbamoylase activity of L-carbamoylase $E_{1V}$, relative to the carbamoylase activity of the L-carbamoylase $E_{1S}$, in %.

4.5.6 Preferred Carbamoylase Variants of SEQ ID NOs: 1-9

In the context of the invention, L-carbamoylases $E_1$, the polypeptide sequence of which is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, are generally denoted as "$E_{1S}$".

L-carbamoylases $E_1$, the polypeptide sequence of which is selected from variants of a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, are generally denoted as "$E_{1V}$".

In a preferred embodiment of the method according to the first aspect of the present invention, the reaction in step (c) is catalyzed by an L-carbamoylase $E_1$, and the polypeptide sequence of the L-carbamoylase $E_1$ is selected from the group consisting of SEQ ID NO: 1 and variants thereof, SEQ ID NO: 2 and variants thereof, SEQ ID NO: 3 and variants thereof, SEQ ID NO: 4 and variants thereof, SEQ ID NO: 5 and variants thereof, SEQ ID NO: 6 and variants thereof, SEQ ID NO: 7 and variants thereof, SEQ ID NO: 8 and variants thereof, SEQ ID NO: 9 and variants thereof. More preferably, the reaction in step (c) is catalyzed by an L-carbamoylase $E_1$, and the polypeptide sequence of the L-carbamoylase $E_1$ is selected from the group consisting of SEQ ID NO: 1 and variants of SEQ ID NO: 1.

4.5.6.1 Preferred Variants of SEQ ID NO: 1

According to the invention, the polypeptide sequence of the L-carbamoylase $E_1$ may also be a variant of SEQ ID NO: 1.

The L-carbamoylase $E_1$, the polypeptide sequence of which is SEQ ID NO: 1, is denoted as "$E_{101S}$". L-carbamoylases $E_1$, the polypeptide sequence of which is selected from variants of SEQ ID NO: 1, are generally denoted as "$E_{101V}$".

A variant of the polypeptide sequence of SEQ ID NO: 1 is a polypeptide with sequence identity of at least 60%, preferably ≥65%, more preferably ≥70%, more preferably ≥75%, more preferably ≥80%, more preferably ≥85%, more preferably ≥90%, more preferably ≥91%, more preferably ≥92%, more preferably ≥93%, more preferably ≥94%, more preferably ≥95%, more preferably ≥96%, more preferably ≥97%, more preferably ≥98%, more preferably ≥99%, more preferably ≥99.9% sequence identity to polypeptide sequence SEQ ID NO: 1.

The polypeptide sequence of a variant of the polypeptide sequence SEQ ID NO: 1 is not identical to SEQ ID NO: 1.

According to the invention, an L-carbamoylase $E_{101V}$ has carbamoylase activity and L-carbamoylase activity, determined as described under items 4.5.4.2 and 4.5.4.3.1.

According to the invention, an L-carbamoylase $E_{101V}$ preferably has carbamoylase activity of at least 1%, preferably of at least 10%, more preferably of at least 20%, more preferably of at least 30%, more preferably of at least 40%, more preferably of at least 50%, more preferably of at least 60%, more preferably of at least 70%, more preferably of at least 80%, more preferably of at least 90%, more preferably of at least 99%, more preferably of at least 100% the carbamoylase activity of the L-carbamoylase $E_{101S}$, wherein the carbamoylase activity of $E_{101V}$, relative to the carbamoylase activity of $E_{101S}$, is determined by Assay C described under item 4.5.5.2.

It is even more preferable according to the invention, that an L-carbamoylase $E_{101V}$ has carbamoylase activity in the range of 1 to 1000%, preferably in the range of 5 to 500%, more preferably in the range of 10 to 400%, more preferably in the range of 40 to 200%, more preferably in the range of 50 to 150%, more preferably in the range of 60 to 140%, more preferably in the range of 70 to 130%, more preferably in the range of 80 to 120%, more preferably in the range of 90 to 110%, more preferably 100% the carbamoylase activity of the L-carbamoylase $E_{101S}$, wherein the carbamoylase activity of $E_{101V}$, relative to the carbamoylase activity of $E_{101S}$, is determined by Assay C described under item 4.5.5.2.

4.5.6.2 Preferred Variants of SEQ ID NO: 2

According to the invention, the polypeptide sequence of the L-carbamoylase $E_1$ may also be a variant of SEQ ID NO: 2.

The L-carbamoylase $E_1$, the polypeptide sequence of which is SEQ ID NO: 2, is denoted as "$E_{102S}$". L-carbamoylases $E_1$, the polypeptide sequence of which is selected from variants of SEQ ID NO: 2, are generally denoted as "$E_{102V}$".

A variant of the polypeptide sequence of SEQ ID NO: 2 is a polypeptide with sequence identity of at least 60%, preferably ≥65%, more preferably ≥70%, more preferably ≥75%, more preferably ≥80%, more preferably ≥85%, more preferably ≥90%, more preferably ≥91%, more preferably ≥92%, more preferably ≥93%, more preferably ≥94%, more preferably ≥95%, more preferably ≥96%, more preferably ≥97%, more preferably ≥98%, more preferably ≥99%, more preferably ≥99.9% sequence identity to polypeptide sequence SEQ ID NO: 2.

The polypeptide sequence of a variant of the polypeptide sequence SEQ ID NO: 2 is not identical to SEQ ID NO: 2.

According to the invention, an L-carbamoylase $E_{102V}$ has carbamoylase activity and L-carbamoylase activity, determined as described under items 4.5.4.2 and 4.5.4.3.1.

According to the invention, an L-carbamoylase $E_{102V}$ preferably has carbamoylase activity of at least 1%, preferably of at least 10%, more preferably of at least 20%, more preferably of at least 30%, more preferably of at least 40%, more preferably of at least 50%, more preferably of at least 60%, more preferably of at least 70%, more preferably of at least 80%, more preferably of at least 90%, more preferably of at least 99%, more preferably of at least 100% the carbamoylase activity of the L-carbamoylase $E_{102S}$, wherein the carbamoylase activity of $E_{102V}$, relative to the carbamoylase activity of $E_{102S}$, is determined by Assay C described under item 4.5.5.2.

It is even more preferable according to the invention, that an L-carbamoylase $E_{102V}$ has carbamoylase activity in the range of 1 to 1000%, preferably in the range of 5 to 500%, more preferably in the range of 10 to 400%, more preferably in the range of 40 to 200%, more preferably in the range of 50 to 150%, more preferably in the range of 60 to 140%, more preferably in the range of 70 to 130%, more preferably in the range of 80 to 120%, more preferably in the range of 90 to 110%, more preferably 100% the carbamoylase activity of the L-carbamoylase $E_{102S}$, wherein the carbamoylase activity of $E_{102V}$, relative to the carbamoylase activity of $E_{102S}$, is determined by Assay C described under item 4.5.5.2.

4.5.6.3 Preferred Variants of SEQ ID NO: 3

According to the invention, the polypeptide sequence of the L-carbamoylase $E_1$ may also be a variant of SEQ ID NO: 3.

The L-carbamoylase $E_1$, the polypeptide sequence of which is SEQ ID NO: 3, is denoted as "$E_{103S}$". L-carbamoylases $E_1$, the polypeptide sequence of which is selected from variants of SEQ ID NO: 3, are generally denoted as "$E_{103V}$".

A variant of the polypeptide sequence of SEQ ID NO: 3 is a polypeptide with sequence identity of at least 60%, preferably ≥65%, more preferably ≥70%, more preferably ≥75%, more preferably ≥80%, more preferably ≥85%, more preferably ≥90%, more preferably ≥91%, more preferably ≥92%, more preferably ≥93%, more preferably ≥94%, more preferably ≥95%, more preferably ≥96%, more preferably ≥97%, more preferably ≥98%, more preferably ≥99%, more preferably ≥99.9% sequence identity to polypeptide sequence SEQ ID NO: 3.

The polypeptide sequence of a variant of the polypeptide sequence SEQ ID NO: 3 is not identical to SEQ ID NO: 3.

According to the invention, an L-carbamoylase $E_{103V}$ has carbamoylase activity and L-carbamoylase activity, determined as described under items 4.5.4.2 and 4.5.4.3.1.

According to the invention, an L-carbamoylase $E_{103V}$ preferably has carbamoylase activity of at least 1%, preferably of at least 10%, more preferably of at least 20%, more preferably of at least 30%, more preferably of at least 40%, more preferably of at least 50%, more preferably of at least 60%, more preferably of at least 70%, more preferably of at least 80%, more preferably of at least 90%, more preferably of at least 99%, more preferably of at least 100% the carbamoylase activity of the L-carbamoylase $E_{103S}$, wherein the carbamoylase activity of $E_{103V}$, relative to the carbamoylase activity of $E_{103S}$, is determined by Assay C described under item 4.5.5.2.

It is even more preferable according to the invention, that an L-carbamoylase $E_{103V}$ has carbamoylase activity in the range of 1 to 1000%, preferably in the range of 5 to 500%, more preferably in the range of 10 to 400%, more preferably in the range of 40 to 200%, more preferably in the range of 50 to 150%, more preferably in the range of 60 to 140%, more preferably in the range of 70 to 130%, more preferably in the range of 80 to 120%, more preferably in the range of 90 to 110%, more preferably 100% the carbamoylase activity of the L-carbamoylase $E_{103S}$, wherein the carbamoylase activity of $E_{103V}$, relative to the carbamoylase activity of $E_{103S}$, is determined by Assay C described under item 4.5.5.2.

4.5.6.4 Preferred Variants of SEQ ID NO: 4

According to the invention, the polypeptide sequence of the L-carbamoylase $E_1$ may also be a variant of SEQ ID NO: 4.

The L-carbamoylase $E_1$, the polypeptide sequence of which is SEQ ID NO: 4, is denoted as "$E_{104S}$". L-carbamoylases $E_1$, the polypeptide sequence of which is selected from variants of SEQ ID NO: 4, are generally denoted as "$E_{104V}$".

A variant of the polypeptide sequence of SEQ ID NO: 4 is a polypeptide with sequence identity of at least 60%, preferably ≥65%, more preferably ≥70%, more preferably ≥75%, more preferably ≥80%, more preferably ≥85%, more preferably ≥90%, more preferably ≥91%, more preferably ≥92%, more preferably >93%, more preferably ≥94%, more preferably ≥95%, more preferably ≥96%, more preferably ≥97%, more preferably ≥98%, more preferably ≥99%, more preferably ≥99.9% sequence identity to polypeptide sequence SEQ ID NO: 4.

The polypeptide sequence of a variant of the polypeptide sequence SEQ ID NO: 4 is not identical to SEQ ID NO: 4.

According to the invention, an L-carbamoylase $E_{104V}$ has carbamoylase activity and L-carbamoylase activity, determined as described under items 4.5.4.2 and 4.5.4.3.1.

According to the invention, an L-carbamoylase $E_{104V}$ preferably has carbamoylase activity of at least 1%, preferably of at least 10%, more preferably of at least 20%, more preferably of at least 30%, more preferably of at least 40%, more preferably of at least 50%, more preferably of at least 60%, more preferably of at least 70%, more preferably of at least 80%, more preferably of at least 90%, more preferably of at least 99%, more preferably of at least 100% the carbamoylase activity of the L-carbamoylase $E_{104S}$, wherein the carbamoylase activity of $E_{104V}$, relative to the carbamoylase activity of $E_{104S}$, is determined by Assay C described under item 4.5.5.2.

It is even more preferable according to the invention, that an L-carbamoylase $E_{104V}$ has carbamoylase activity in the range of 1 to 1000%, preferably in the range of 5 to 500%, more preferably in the range of 10 to 400%, more preferably in the range of 40 to 200%, more preferably in the range of 50 to 150%, more preferably in the range of 60 to 140%, more preferably in the range of 70 to 130%, more preferably in the range of 80 to 120%, more preferably in the range of 90 to 110%, more preferably 100% the carbamoylase activity of the L-carbamoylase $E_{104S}$, wherein the carbamoylase activity of $E_{104V}$, relative to the carbamoylase activity of $E_{104S}$, is determined by Assay C described under item 4.5.5.2.

4.5.6.5 Preferred Variants of SEQ ID NO: 5

According to the invention, the polypeptide sequence of the L-carbamoylase $E_1$ may also be a variant of SEQ ID NO: 5.

The L-carbamoylase $E_1$, the polypeptide sequence of which is SEQ ID NO: 5, is denoted as "$E_{105S}$". L-carbamoylases $E_1$, the polypeptide sequence of which is selected from variants of SEQ ID NO: 5, are generally denoted as "$E_{105V}$".

A variant of the polypeptide sequence of SEQ ID NO: 5 is a polypeptide with sequence identity of at least 60%, preferably ≥65%, more preferably ≥70%, more preferably ≥75%, more preferably ≥80%, more preferably ≥85%, more preferably ≥90%, more preferably ≥91%, more preferably ≥92%, more preferably ≥93%, more preferably ≥94%, more preferably ≥95%, more preferably ≥96%, more preferably ≥97%, more preferably ≥98%, more preferably ≥99%, more preferably ≥99.9% sequence identity to polypeptide sequence SEQ ID NO: 5.

The polypeptide sequence of a variant of the polypeptide sequence SEQ ID NO: 5 is not identical to SEQ ID NO: 5.

According to the invention, an L-carbamoylase $E_{105V}$ has carbamoylase activity and L-carbamoylase activity, determined as described under items 4.5.4.2 and 4.5.4.3.1.

According to the invention, an L-carbamoylase $E_{105V}$ preferably has carbamoylase activity of at least 1%, preferably of at least 10%, more preferably of at least 20%, more preferably of at least 30%, more preferably of at least 40%, more preferably of at least 50%, more preferably of at least 60%, more preferably of at least 70%, more preferably of at least 80%, more preferably of at least 90%, more preferably of at least 99%, more preferably of at least 100% the carbamoylase activity of the L-carbamoylase $E_{105S}$, wherein the carbamoylase activity of $E_{105V}$, relative to the carbamoylase activity of $E_{105S}$, is determined by Assay C described under item 4.5.5.2.

It is even more preferable according to the invention, that an L-carbamoylase $E_{105V}$ has carbamoylase activity in the range of 1 to 1000%, preferably in the range of 5 to 500%, more preferably in the range of 10 to 400%, more preferably in the range of 40 to 200%, more preferably in the range of 50 to 150%, more preferably in the range of 60 to 140%, more preferably in the range of 70 to 130%, more preferably in the range of 80 to 120%, more preferably in the range of 90 to 110%, more preferably 100% the carbamoylase activity of the L-carbamoylase $E_{105S}$, wherein the carbamoylase activity of $E_{105V}$, relative to the carbamoylase activity of $E_{105S}$, is determined by Assay C described under item 4.5.5.2.

4.5.6.6 Preferred Variants of SEQ ID NO: 6

According to the invention, the polypeptide sequence of the L-carbamoylase $E_1$ may also be a variant of SEQ ID NO: 6.

The L-carbamoylase $E_1$, the polypeptide sequence of which is SEQ ID NO: 6, is denoted as "$E_{106S}$". L-carbamoylases $E_1$, the polypeptide sequence of which is selected from variants of SEQ ID NO: 6, are generally denoted as "$E_{106V}$".

A variant of the polypeptide sequence of SEQ ID NO: 6 is a polypeptide with sequence identity of at least 60%, preferably ≥65%, more preferably ≥70%, more preferably ≥75%, more preferably ≥80%, more preferably ≥85%, more preferably ≥90%, more preferably ≥91%, more preferably ≥92%, more preferably ≥93%, more preferably ≥94%, more preferably ≥95%, more preferably ≥96%, more preferably ≥97%, more preferably ≥98%, more preferably ≥99%, more preferably ≥99.9% sequence identity to polypeptide sequence SEQ ID NO: 6.

The polypeptide sequence of a variant of the polypeptide sequence SEQ ID NO: 6 is not identical to SEQ ID NO: 6.

According to the invention, an L-carbamoylase $E_{106V}$ has carbamoylase activity and L-carbamoylase activity, determined as described under items 4.5.4.2 and 4.5.4.3.1.

According to the invention, an L-carbamoylase $E_{106V}$ preferably has carbamoylase activity of at least 1%, preferably of at least 10%, more preferably of at least 20%, more preferably of at least 30%, more preferably of at least 40%, more preferably of at least 50%, more preferably of at least 60%, more preferably of at least 70%, more preferably of at least 80%, more preferably of at least 90%, more preferably of at least 99%, more preferably of at least 100% the carbamoylase activity of the L-carbamoylase $E_{106S}$, wherein the carbamoylase activity of $E_{106V}$, relative to the carbamoylase activity of $E_{106S}$, is determined by Assay C described under item 4.5.5.2.

It is even more preferable according to the invention, that an L-carbamoylase $E_{106V}$ has carbamoylase activity in the range of 1 to 1000%, preferably in the range of 5 to 500%, more preferably in the range of 10 to 400%, more preferably in the range of 40 to 200%, more preferably in the range of 50 to 150%, more preferably in the range of 60 to 140%, more preferably in the range of 70 to 130%, more preferably in the range of 80 to 120%, more preferably in the range of 90 to 110%, more preferably 100% the carbamoylase activity of the L-carbamoylase $E_{106S}$, wherein the carbamoylase activity of $E_{106V}$, relative to the carbamoylase activity of $E_{106S}$, is determined by Assay C described under item 4.5.5.2.

4.5.6.7 Preferred Variants of SEQ ID NO: 7

According to the invention, the polypeptide sequence of the L-carbamoylase $E_1$ may also be a variant of SEQ ID NO: 7.

The L-carbamoylase $E_1$, the polypeptide sequence of which is SEQ ID NO: 7, is denoted as "$E_{107S}$". L-carbamoylases $E_1$, the polypeptide sequence of which is selected from variants of SEQ ID NO: 7, are generally denoted as "$E_{107V}$".

A variant of the polypeptide sequence of SEQ ID NO: 7 is a polypeptide with sequence identity of at least 60%, preferably ≥65%, more preferably ≥70%, more preferably ≥75%, more preferably ≥80%, more preferably ≥85%, more preferably ≥90%, more preferably ≥91%, more preferably ≥92%, more preferably ≥93%, more preferably ≥94%, more preferably ≥95%, more preferably ≥96%, more preferably ≥97%, more preferably ≥98%, more preferably ≥99%, more preferably ≥99.9% sequence identity to polypeptide sequence SEQ ID NO: 7.

The polypeptide sequence of a variant of the polypeptide sequence SEQ ID NO: 7 is not identical to SEQ ID NO: 7.

According to the invention, an L-carbamoylase $E_{107V}$ has carbamoylase activity and L-carbamoylase activity, determined as described under items 4.5.4.2 and 4.5.4.3.1.

According to the invention, an L-carbamoylase $E_{107V}$ preferably has carbamoylase activity of at least 1%, preferably of at least 10%, more preferably of at least 20%, more preferably of at least 30%, more preferably of at least 40%, more preferably of at least 50%, more preferably of at least 60%, more preferably of at least 70%, more preferably of at least 80%, more preferably of at least 90%, more preferably of at least 99%, more preferably of at least 100% the carbamoylase activity of the L-carbamoylase $E_{107S}$, wherein the carbamoylase activity of $E_{107V}$, relative to the carbamoylase activity of $E_{107S}$, is determined by Assay C described under item 4.5.5.2.

It is even more preferable according to the invention, that an L-carbamoylase $E_{107V}$ has carbamoylase activity in the range of 1 to 1000%, preferably in the range of 5 to 500%, more preferably in the range of 10 to 400%, more preferably in the range of 40 to 200%, more preferably in the range of 50 to 150%, more preferably in the range of 60 to 140%, more preferably in the range of 70 to 130%, more preferably in the range of 80 to 120%, more preferably in the range of 90 to 110%, more preferably 100% the carbamoylase activity of the L-carbamoylase $E_{107S}$, wherein the carbamoylase activity of $E_{107V}$, relative to the carbamoylase activity of $E_{107S}$, is determined by Assay C described under item 4.5.5.2.

4.5.6.8 Preferred Variants of SEQ ID NO: 8

According to the invention, the polypeptide sequence of the L-carbamoylase $E_1$ may also be a variant of SEQ ID NO: 8.

The L-carbamoylase $E_1$, the polypeptide sequence of which is SEQ ID NO: 8, is denoted as "$E_{108S}$". L-carbamoylases $E_1$, the polypeptide sequence of which is selected from variants of SEQ ID NO: 8, are generally denoted as "$E_{108V}$".

A variant of the polypeptide sequence of SEQ ID NO: 8 is a polypeptide with sequence identity of at least 60%, preferably ≥65%, more preferably ≥70%, more preferably ≥75%, more preferably ≥80%, more preferably ≥85%, more preferably ≥90%, more preferably ≥91%, more preferably ≥92%, more preferably ≥93%, more preferably ≥94%, more preferably ≥95%, more preferably ≥96%, more preferably ≥97%, more preferably ≥98%, more preferably ≥99%, more preferably ≥99.9% sequence identity to polypeptide sequence SEQ ID NO: 8.

The polypeptide sequence of a variant of the polypeptide sequence SEQ ID NO: 8 is not identical to SEQ ID NO: 8.

According to the invention, an L-carbamoylase $E_{108V}$ has carbamoylase activity and L-carbamoylase activity, determined as described under items 4.5.4.2 and 4.5.4.3.1.

According to the invention, an L-carbamoylase $E_{108V}$ preferably has carbamoylase activity of at least 1%, preferably of at least 10%, more preferably of at least 20%, more preferably of at least 30%, more preferably of at least 40%, more preferably of at least 50%, more preferably of at least 60%, more preferably of at least 70%, more preferably of at least 80%, more preferably of at least 90%, more preferably of at least 99%, more preferably of at least 100% the carbamoylase activity of the L-carbamoylase $E_{108S}$, wherein the carbamoylase activity of $E_{108V}$, relative to the carbamoylase activity of $E_{108S}$, is determined by Assay C described under item 4.5.5.2.

It is even more preferable according to the invention, that an L-carbamoylase $E_{108V}$ has carbamoylase activity in the range of 1 to 1000%, preferably in the range of 5 to 500%, more preferably in the range of 10 to 400%, more preferably in the range of 40 to 200%, more preferably in the range of 50 to 150%, more preferably in the range of 60 to 140%, more preferably in the range of 70 to 130%, more preferably in the range of 80 to 120%, more preferably in the range of 90 to 110%, more preferably 100% the carbamoylase activity of the L-carbamoylase $E_{108S}$, wherein the carbamoylase activity of $E_{108}$, relative to the carbamoylase activity of $E_{108S}$, is determined by Assay C described under item 4.5.5.2.

4.5.6.9 Preferred Variants of SEQ ID NO: 9

According to the invention, the polypeptide sequence of the L-carbamoylase $E_1$ may also be a variant of SEQ ID NO: 9.

The L-carbamoylase $E_1$, the polypeptide sequence of which is SEQ ID NO: 9, is denoted as "$E_{109S}$". L-carbamoylases $E_1$, the polypeptide sequence of which is selected from variants of SEQ ID NO: 9, are generally denoted as "$E_{109V}$".

A variant of the polypeptide sequence of SEQ ID NO: 9 is a polypeptide with sequence identity of at least 60%, preferably ≥65%, more preferably ≥70%, more preferably ≥75%, more preferably ≥80%, more preferably ≥85%, more preferably ≥90%, more preferably ≥91%, more preferably ≥92%, more preferably ≥93%, more preferably ≥94%, more preferably ≥95%, more preferably ≥96%, more preferably ≥97%, more preferably ≥98%, more preferably ≥99%, more preferably ≥99.9% sequence identity to polypeptide sequence SEQ ID NO: 9.

The polypeptide sequence of a variant of the polypeptide sequence SEQ ID NO: 9 is not identical to SEQ ID NO: 9.

According to the invention, an L-carbamoylase $E_{109V}$ has carbamoylase activity and L-carbamoylase activity, determined as described under items 4.5.4.2 and 4.5.4.3.1.

According to the invention, an L-carbamoylase $E_{109V}$ preferably has carbamoylase activity of at least 1%, preferably of at least 10%, more preferably of at least 20%, more preferably of at least 30%, more preferably of at least 40%, more preferably of at least 50%, more preferably of at least 60%, more preferably of at least 70%, more preferably of at least 80%, more preferably of at least 90%, more preferably of at least 99%, more preferably of at least 100% the carbamoylase activity of the L-carbamoylase $E_{109S}$, wherein the carbamoylase activity of $E_{109V}$, relative to the carbamoylase activity of $E_{109S}$, is determined by Assay C described under item 4.5.5.2.

It is even more preferable according to the invention, that an L-carbamoylase $E_{109V}$ has carbamoylase activity in the range of 1 to 1000%, preferably in the range of 5 to 500%, more preferably in the range of 10 to 400%, more preferably in the range of 40 to 200%, more preferably in the range of 50 to 150%, more preferably in the range of 60 to 140%, more preferably in the range of 70 to 130%, more preferably in the range of 80 to 120%, more preferably in the range of 90 to 110%, more preferably 100% the carbamoylase activity of the L-carbamoylase $E_{109S}$, wherein the carbamoylase activity of $E_{109V}$, relative to the carbamoylase activity of $E_{109S}$, is determined by Assay C described under item 4.5.5.2.

4.5.7 Preferred Method Conditions in Step (c)

The reaction in step (c) of the method according to the first aspect of the present invention may be carried out under conditions known to the skilled person.

The reaction medium is preferably aqueous, more preferably an aqueous buffer.

Exemplary buffers commonly used in biotransformation reactions and advantageously used herein include Tris, phosphate, or any of Good's buffers, such as 2-(N-morpholino)ethanesulfonic acid ("MES"), N-(2-acetamido)iminodiacetic acid ("ADA"), piperazine-N,N'-bis(2-ethanesulfonic acid) ("PIPES"), N-(2-acetamido)-2-aminoethanesulfonic acid ("ACES"), P-hydroxy-4-morpholinepropanesulfonic acid ("MOPSO"), cholamine chloride, 3-(N-morpholino)propanesulfonic acid ("MOPS"), N,N-Bis(2-hydroxyethyl)-2-aminoethanesulfonic acid ("BES"), 2-[[1,3-dihydroxy-2-(hydroxymethyl) propan-2-yl]amino]ethanesulfonic acid ("TES"), 4-(2-hydroxyethyl)-1-piperazineethanesulfonic acid ("HEPES"), 3-(Bis(2-hydroxyethyl)amino)-2-hydroxypropane-1-sulfonic acid ("DIPSO"), acetamidoglycine, 3-(N-Tris(hydroxymethyl)methylamino(-2-hydroxypropane) sulfonic acid ("TAPSO"), piperazine-N,N'-bis(2-hydroxypropanesulfonic acid) ("POPSO"), 4-(2-Hydroxyethyl) piperazine-1-(2-hydroxypropanesulfonic acid) ("HEPPSO"), 3-[4-(2-Hydroxyethyl)-1-piperazinyl]propanesulfonic acid ("HEPPS"), tricine, glycinamide, bicine, or 3-[[1,3-dihydroxy-2-(hydroxymethyl) propan-2-yl] amino]propane-1-sulfonic acid ("TAPS").

In some embodiments, ammonium can act as a buffer. One or more organic solvents can also be added to the reaction.

The buffer preferably contains metal salts, more preferably metal salts such as halogenides of metals, preferably halogenides of monovalent or bivalent or trivalent metals, preferably chlorides of monovalent or bivalent metals, preferably $CoCl_2$ or $MnCl_2$, preferably $CoCl_2$.

The concentration of these metal salts in the reaction medium is preferably in the range from 1 µM to 1 M, more preferably 1 mM to 100 mM, even more preferably 1 to 10 mM.

Preferably, step (c) of the method according to the first aspect of the invention is carried out in a phosphate buffer.

The pH of the reaction medium in step (c) of the method according to the first aspect of the invention is preferably in the range of from 2 to 10, more preferably in the range of from 5 to 8, more preferably 7.2 to 7.5, most preferably 7.5.

Preferably, step (c) of the method according to the first aspect of the invention is carried out at a temperature in the range of from 20° C. to 70° C., more preferably in the range of from 30° C. to 55° C., most preferably 50° C.

Preferably, the total concentration of all carbamoylases $E_1$ in the reaction solution in step (c) is in the range of from 1 µM to 10 mM, preferably 10 µM to 1 mM, more preferably 0.1 mM to 0.5 mM, most preferably 0.4 mM.

In alternative preferred embodiments, the total concentration of all carbamoylases $E_1$ in the reaction solution in step (c) is in the range of from 1 µg/l to 10 g/l, preferably 0.1 mg/l to 5 g/l, more preferably 1 mg/l to 1 g/l, more preferably 5 mg/l to 500 mg/l.

Preferably, the initial concentration of all the compounds according to formula L-(II) in the reaction medium in step (c) is in the range of from 1 µM to 1 M, preferably of from 10 µM to 0.5 M, more preferably of from 0.1 mM to 0.1 M, more preferably of from 1 mM to 10 mM, most preferably 1.25 mM.

If compounds according to formula D-(II) are present in the reaction medium in step (c), the initial concentration of all the compounds according to formula D-(II) in the reaction medium is preferably from 1% to 100% the concentration of all the compounds according to formula L-(II), more preferably 10% to 100% the concentration, even more preferably 50 to 100%, even more preferably 100% the concentration of all the compounds according to formula L-(II).

"Initial concentration of all the compounds according to formula L-(II)/D-(II)" refers to the concentration of the respective compound L-(II) or D-(II) respectively, in the reaction medium when the respective compounds are employed in step (c).

4.5.8 Step (b)

4.5.8.1 Enzymatic Catalysis of Step (b)

In a preferred embodiment of the method according to the first aspect of the invention, the compound according to formula L-(II) is obtained by a step (b) in which a compound according to formula L-(III) is reacted to give a compound according to formula L-(II):

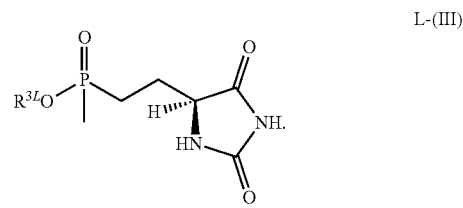

L-(III)

Step (b) gives the starting material for step (c).

$R^{3L}$ is a radical selected from the above-mentioned formulae (VIII), (IX), (X), preferably selected from the formulae (VIII), (IX), more preferably $R^{3L}$ has formula (VIII).

When $R^{3L}$ is a radical of the formula (VIII), the radical $R^{3L}$ may be selected from the above-mentioned formulae L-(VIII) and D-(VIII), preferably L-(VIII).

When $R^{3L}$ is a radical of the formula (IX), the radical $R^{3L}$ may be selected from the above-mentioned formulae L-(IX) and D-(IX), preferably L-(IX).

When $R^{3L}$ is a radical of the formula (X), the radical $R^{3L}$ may be selected from the above-mentioned formulae L-(X) and D-(X), preferably L-(X).

The reaction according step (b) is enzymatically catalyzed, namely it is catalyzed by a hydantoinase $E_2$.

4.5.8.2 Enantioselective and Enantiospecific Catalysis of Step (b)

Step (b) of the method according to the first aspect of the present invention is preferably L-enantioselective, even more preferably L-enantiospecific.

In such a preferred embodiment, L-(III) is in particular employed in step (b) as a mixture $M_{III}$ comprising at least one compound L-(III) and at least one compound D-(III), wherein D-(III) has the following formula:

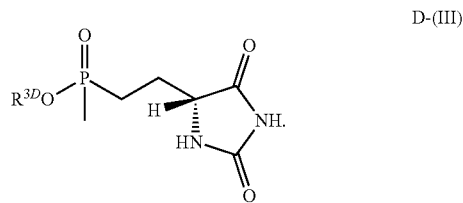

D-(III)

$R^{3D}$ is a radical selected from the above-mentioned formulae (VIII), (IX), (X), preferably selected from the formulae (VIII), (IX), more preferably $R^{3D}$ has formula (VIII).

When $R^{3D}$ is a radical of the formula (VIII), the radical $R^{3D}$ may be selected from the above-mentioned formulae L-(VIII) and D-(VIII), preferably L-(VIII).

When $R^{3D}$ is a radical of the formula (IX), the radical $R^{3D}$ may be selected from the above-mentioned formulae L-(IX) and D-(IX), preferably L-(IX).

When $R^{3D}$ is a radical of the formula (X), the radical $R^{3D}$ may be selected from the above-mentioned formulae L-(X) and D-(X), preferably L-(X).

Mixture $M_{II}$ preferably comprises at least one compound L-(III) and at least one compound D-(III), wherein $R^{3L}=R^{3D}$.

For such mixtures Mu, it may be observed that the at least one compound D-(II) undergoes a reaction according to step (b)*, i.e. parallel to step (b).

Namely, in the reaction according to step (b)*, the at least one compound D-(III) in mixture $M_{II}$ is reacted to give a compound according to formula D-(II), wherein compounds according to formula D-(II) are explained above (in particular under item 4.5.1.2).

In case that step (b) is "L-enantioselective", this means that in case a mixture Mil is employed in step (b), then there is either no reaction according to step (b)* of any compound according to formula D-(III) to a compound according to D-(II) in the mixture $M_{II}$ or, in case there is a reaction according to step (b)*, then there is at least one pair of compounds D-(III)(II)*/L-(III)(II)* in the mixture Mu, for which the reaction according to step (b)* of D-(III)(II)* to give D-(II)(II)*, is lesser than the rate of the reaction according to step (b) of L-(III)(II)* to give L-(II)(II)*.

D-(III)(II)* is a compound according to formula D-(III), and L-(III)(II)* is a compound according to formula L-(III), wherein the radical $R^{3L}$ in L-(III)(II)* and the radical $R^{3D}$ in D-(III)+ are identical.

D-(II)(II)* is a compound according to formula D-(II), and L-(II)(II)* is a compound according to formula L-(II), wherein the radical $R^{2L}$ in L-(II)(II)* and the radical $R^{2D}$ in D-(II)+ are identical.

Preferably, the radical $R^{2L}$ in L-(II)+ and the radical $R^{3L}$ in L-(III)+ are identical. Preferably, the radical $R^{2D}$ in D-(II)(II)* and the radical $R^{3D}$ in D-(III)+ are identical.

Step (b) is "L-enantiospecific", if the rate of reaction according to step (b)* is essentially zero, i.e. there is no reaction according to step (b)* of any compound according to formula D-(III) to a compound according to D-(II) in the mixture $M_{III}$.

In a preferred embodiment, the molar ratio of all compounds according to formula L-(III) in the mixture $M_{III}$ to all compounds according to formula D-(III) in the mixture $M_{III}$ is essentially 1:1.

In other preferred embodiments, the molar ratio of all compounds according to formula L-(III) in the mixture $M_{III}$ to all compounds according to formula D-(III) in the mixture $M_{III}$ is in the range of from 3:2 to 1:99, more preferably in the range of from 1.01:1 to 1:99, more preferably in the range of from 1:1 to 1:99, more preferably in the range of from 1:1.01 to 1:99, more preferably in the range of from 1:1.01 to 1:9, more preferably in the range of from 1:1.01 to 1:8, more preferably in the range of from 1:1.01 to 1:3.

Alternatively, D-(III) is comprised in an excess to L-(III) in mixture Mm, meaning that, while at least one compound according to formula L-(III) is in the mixture $M_{III}$, the molar ratio of all compounds according to formula L-(III) is in the mixture $M_{III}$ to all compounds according to formula D-(III) in the mixture $M_{III}$ is <1:1, preferably <0.9:1, more preferably <0.75:1, more preferably <0.5:1, more preferably <0.2:1, more preferably <0.1:1, more preferably <0.01:1.

Step (b) is in particular L-enantioselective, if it is preferably catalyzed by an L-hydantoinase $E_2$, which may be determined by the skilled person as set forth under 4.5.10.3.

In case step (b) is L-enantioselective with respect to a given pair of compounds D-(III)(II)*/L-(III)+, the reaction according to step (b) of L-(III)(II)* to give L-(II)(II)* proceeds preferably at a reaction rate that is at least 2 times greater, preferably at least 10 times greater, more preferably at least 100 times greater, even more preferably at least 103 times greater, even more preferably at least 104 times greater, even more preferably at least 105 times greater than the reaction rate at which step (b)* of D-(III)(II)* to give D-(II)(II)* proceeds.

To quantify for a given pair of compounds D-(III)(II)*/L-(III)(II)* the factor at which the reaction rate of step (b) proceeds compared to the reaction rate of step (b)*, the following test may be carried out:

(1) An equimolar mixture [molar ratio of the two compounds L-(III)(II)* and D-(III)(II)* is 1:1] is subjected to the respective reactions conditions and the development of the two products L-(I)(II)* and D-(I)(II)* is monitored over time (e.g. by LC-MS as set forth under item 5.4).

(2) When $n_{LII10}$=10 mol-% of the initially employed L-(III)(II)* has reacted to the product L-(II)(II)*, the molar amount of D-(II)(II)* that was formed by reaction from D-(III)+ [in mol-% relative to the initially employed D-(II)(II)*] is measured (=$n_{DII10}$).

(3) The ratio of $n_{DII10}/n_{DII10}=10/n_{DII10}$ gives the factor by which the reaction rate of step (b) proceeds compared to the reaction rate of step (b)* for the given pair of compounds D-(III)(II)*/L-(III)(II)*.

If $n_{LII10}/n_{DII10}>1$, the reaction rate of step (b) is greater than the reaction rate of step (b)* for the given pair of compounds D-(III)(II)*/L-(III)+.

If $n_{LII10}/n_{DII10}<1$, the reaction rate of step (b) is lesser than the reaction rate of step (b)* for the given pair of compounds D-(III)(II)*/L-(III)(II)*.

If $n_{LII10}/n_{DII10}=1$, the reaction rates of steps (b and b)* are the same for the given pair of compounds D-(III)(II)*/L-(III)(II)*.

The reaction according to step (b) of the preferred embodiment of the first aspect of the invention is catalyzed by a hydantoinase ("dihydropyrimidinase") $E_2$.

Namely, it was surprisingly found that hydantoinases accept compounds of formula L-(III) as substrates and convert them to products according to formulae L-(II), and hence catalyze the reaction according to step (b). This finding is of high scientific and economic value, as it further broadens the scope of synthetic routes based on new starting materials for the production of L-glufosinate P-esters and L-glufosinate. Even more surprisingly, it is suggested that L-glufosinate hydantoin, i.e. the compound according to formula L-(III), in which R=H, does not undergo reaction by hydantoinases to give the respective LGA carbamoylate.

In nature, hydantoinases ("dihydropyrimidinases") generally catalyze the reaction of 5,6-dihydrouracil to produce ureidopropionate (see the following reaction <2A>):

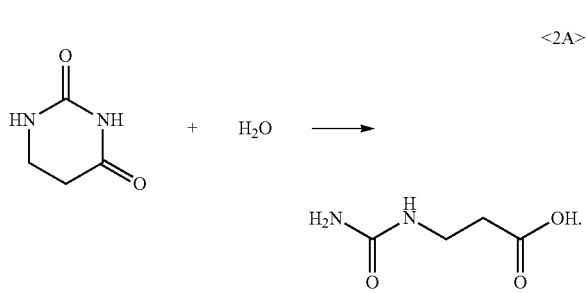

<2A>

They also catalyze the ring opening of monosubstituted hydantoins to give the respective carbamoyl amino acid according to the following reaction <2B>, wherein R* may be an organic residue, e.g. a side chain of one of the naturally occurring amino acids.

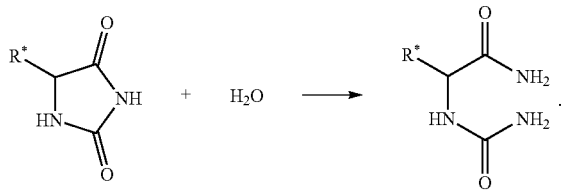
<2B>

Chapter 1.3 (pages 7 to 11) of the dissertation "Untersuchungen zur Substratspezifität und Enantioselektivität mikrobieller Hydantoinasen/Investigations of substrate specificity and enantioselectivity of microbial hydantoinases" by T. Waniek, University of Stuttgart, 2000 (available under: https://elib.uni-stuttgart.de/bitstream/11682/1511/1/Diss.pdf) gives an overview over hydantoinases.

It was now surprisingly found that hydantoinases also accept substrates in which $R^*=R^Y=$

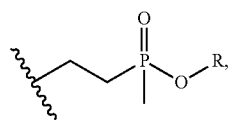

wherein $R=R^{3L}$.

Surprisingly, they supposedly do not accept substrates in which $R^*=R^Y=$

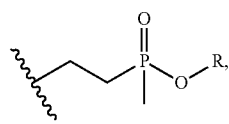

wherein R=H.

In the context of the present invention, a "hydantoinase $E_2$" is a hydantoinase that catalyzes the following reaction <2C> of a carbamoyl substrate S', to the respective amino acid product P'L, wherein $R^*=R^Y=$

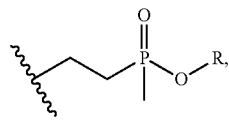

wherein $R=R^{3L}$:

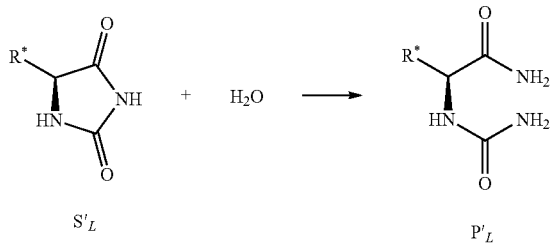
<2C>

In particular, the hydantoinase $E_2$ is a "L-hydantoinase", i.e. it has a greater catalytic activity for reaction <2C> than for reaction <2D>, wherein R* in the substrate S'D in the reaction <2D> and R* in the substrate S'L in the reaction <2C> are identical and $R^*=R^Y=$

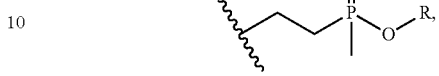

wherein $R=R^{3L}$.

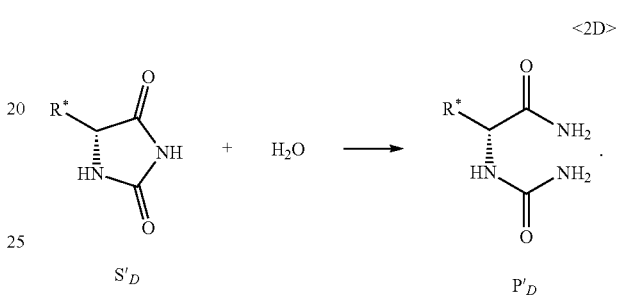
<2D>

As an L-hydantoinase has a higher catalytic activity for reaction <2C> than for reaction <2D>, it is "L-enantioselective". An L-hydantoinase that has no catalytic activity for reaction <2D> and thus only has catalytic activity for reaction <2C> is "L-enantiospecific".

A "D-hydantoinase" is defined as a hydantoinase which is "D-enantioselective", i.e. it has a higher catalytic activity for reaction <2D> than for reaction <2C>. A D-carbamoylase that does not catalyze reaction <2C> and thus only has catalytic activity for reaction <2D> is "D-enantiospecific".

A hydantoinase which has the same catalytic activity for reaction <2C> as for reaction <2D>, is referred to as "non enantioselective hydantoinase".

For determination whether a hydantoinase may be denoted as "L-hydantoinase", "D-hydantoinase" or "non-enantioselective hydantoinase" in the context of the present invention, the procedure according to Assay E (item 4.5.10) may preferably be used.

The hydantoinase $E_2$, in particular the L-hydantoinase $E_2$, that may be used in step (b) of the preferred embodiment of the method according to the first aspect of the invention may originate from *Arthrobacter* sp., in particular *Arthrobacter crystallopoietes, Arthrobacter aurescens, Arthrobacter* sp. BT801; *Alcaligenes* sp., in particular *Alcaligenes faecalis* subsp. *faecalis; Bacillus* sp., in particular *Bacillus fordii; Microbacterium* sp., in particular *Microbacterium liquefaciens* strain AJ3912; *Pseudomonas* sp., in particular *Pseudomonas fluorescens, Pseudomonas aeruginosa.*

A hydantoinase $E_2$, in particular an L-hydantoinase $E_2$ suitable for the method according to the present invention may be the enzyme HyuH, which originates from *Arthrobacter*. Another enzyme may be Dht.

Even more preferably, the hydantoinase $E_2$, in particular the L-hydantoinase $E_2$, that may preferably be used in step (b) according to the first aspect of the invention may originate from *Arthrobacter* sp., in particular *Arthrobacter crystallopoietes, Arthrobacter aurescens, Arthrobacter* sp.

BT801, *Arthrobacter aurescens* DSM 9771, most preferably from *Arthrobacter aurescens* DSM 9771.

A hydantoinase suitable for the method according to the present invention is described e.g. in WO 01/23582 A1 and by J. M. Clemente-Jiménez, S. Martínez-Rodríguez, F. Rodríguez-Vico, F. J. L. Heras-Vázquez, Recent Pat. Biotechnology 2008, 2, 35-46; G. Latacz, E. Pekala, K. Kiec-Kononowicz, Biotechnologia 2006, 2, 189-205.

Further suitable hydantoinases are described by K. Yokozeki, H. Yoshiteru, K. Kubota, Agric. Biol. Chem. 1987, 51, 737-746.

The hydantoinase $E_2$ that may be used in preferred step (b) of the method according to the present invention may be a hydantoinase categorized in the EC class EC 3.5.2.2.

The following table 2 gives preferred examples for polypeptide sequences of hydantoinases $E_2$ that may be preferably used in step (b) of the preferred embodiment of the method according to the first aspect of the invention. The genes encoding the respective hydantoinase $E_2$ and the respective accession code are indicated as far as known.

TABLE 2

Hydantoinases (EC 3.5.2.2)

| Strain | Gene name | GenBank/UniProt accession | SEQ ID NO: of the polypeptide |
|---|---|---|---|
| *Arthrobacter aurescens* DSM 9771 | hyuH | | SEQ ID NO: 10 |
| *Pseudomonas fluorescens* | not assigned | S5MPT0 | SEQ ID NO: 11 |
| *Pseudomonas aeruginosa* | dht | Q9I676 | SEQ ID NO: 12 |
| *Bacillus fordii* MH602 | not assigned | ABL14245 | SEQ ID NO: 13 |
| *Arthrobacter* sp. BT801 | hyuH | AAL55412 | SEQ ID NO: 14 |
| *Alcaligenes faecalis* subsp. *faecalis* | not assigned | | SEQ ID NO: 15 |
| *Microbacterium liquefaciens* strain AJ3912 | not assigned | | SEQ ID NO: 16 |

In a preferred embodiment of the method according to the first aspect of the present invention, the reaction according to step (b) is catalyzed by an hydantoinase $E_2$, wherein the polypeptide sequence of $E_2$ is selected from the group consisting of SEQ ID NO: 10 and variants thereof, SEQ ID NO: 11 and variants thereof, SEQ ID NO: 12 and variants thereof, SEQ ID NO: 13 and variants thereof, SEQ ID NO: 14 and variants thereof, SEQ ID NO: 15 and variants thereof, SEQ ID NO: 16 and variants thereof, preferably SEQ ID NO: 10 and variants thereof.

4.5.9 Assays $D_L$ and $D_D$ for Determining Hydantoinase Activity

The skilled person is aware of hydantoinases, in particular L-hydantoinases, that may be used in step (b) of the preferred method according to the first aspect of the invention.

In particular, Assay $D_L$, described in the following, may be used to determine hydantoinase and L-hydantoinase activity of a given enzyme $E_Y$ and may advantageously be used according to the invention to determine hydantoinase and L-hydantoinase activity in variants of SEQ ID NO: 10, variants of SEQ ID NO: 11, variants of SEQ ID NO: 12, variants of SEQ ID NO: 13, variants of SEQ ID NO: 14, variants of SEQ ID NO: 15, variants of SEQ ID NO: 16.

For comparative reasons, Assay $D_D$ may be used to determine D-hydantoinase activity of a given enzyme $E_Y$.

For the purpose of Assay $D_L$ and Assay $D_D$, the molar mass of the enzyme $E_Y$ to be tested is calculated as the molar mass of the polypeptide sequence of $E_Y$.

Moreover, a substrate according to formula L-(III), wherein $R^{3L}$=n-butyl, is used in Assay $D_L$ so that there is only one chiral carbon atom in the substrate. The compound according to formula L-(III), wherein $R^{3L}$=n-butyl, is denoted as "L-(III)+".

A product according to formula L-(II), wherein $R^{2L}$=n-butyl, is detected in Assay $A_L$.

The compound according to formula L-(II), wherein $R^{2L}$=n-butyl, is denoted as "L-(II)+".

Moreover, a substrate according to formula D-(III), wherein $R^{3D}$=n-butyl, is used in Assay $A_D$ so that there is only one chiral carbon atom in the substrate. The compound according to formula D-(III), wherein $R^{3D}$=n-butyl, is denoted as "D-(III)+".

A product according to formula D-(II), wherein $R^{2D}$=n-butyl, is detected in Assay $A_D$.

The compound according to formula D-(II), wherein $R^{2D}$=n-butyl, is denoted as "D-(II)+".

4.5.9.1 Assay $D_L$:

To 0.9 ml of an aqueous reaction solution (phosphate buffer, pH 7.2, 10 mM $MnCl_2$), containing 50 mM of a compound according to formula L-(III)(II)* are added 400 nmol of $E_Y$ in 0.1 ml aqueous phosphate buffer (pH 7.2, 10 mM $MnCl_2$). The resulting solution is incubated at 25° C., and the pH is held at pH 7.2 by addition of 1 M NaOH. After 300 minutes, the reaction is stopped by addition of 2 M HCl to achieve a pH of 2.5, and the molar amount of the compound according to formula L-(II)(II)* is determined. L-(II)(II)* may be detected by the LC-MS method as described in the example section (item 5.4) for detection of LGA.

4.5.9.2 Assay $D_D$:

To 0.9 ml of an aqueous reaction solution (phosphate buffer, pH 7.2, 10 mM $MnCl_2$), containing 50 mM of a compound according to formula D-(III)(II)* are added 400 nmol of $E_Y$ in 0.1 ml aqueous phosphate buffer (pH 7.2, 10 mM $MnCl_2$). The resulting solution is incubated at 25° C., and the pH is held at pH 7.2 by addition of 1 M NaOH. After 300 minutes, the reaction is stopped by addition of 2 M HCl to achieve a pH of 2.5, and the molar amount of the compound according to formula D-(II)(II)* is determined. D-(II)(II)* may be detected by the LC-MS method as described in the example section (item 5.4) for detection of LGA.

4.5.10 Assay E for Identifying Hydantoinases, L-Hydantoinases, D-Hydantoinases, L- and D-Enantiospecificity The hydantoinase $E_2$ according to the invention is preferably an L-hydantoinase, more preferably L-enantiospecific.

Whether a given enzyme $E_Y$ may be considered a hydantoinase $E_2$, in particular an L-hydantoinase, may be determined in the context of the present invention by the following Assay E:

4.5.10.1 Assay E:

E-1. Firstly, Assay $D_L$ as set forth under item 4.5.9.1 is conducted, and the obtained molar amount of the compound of the formula L-(II)(II)* is determined according to Assay $D_L$.

E-2 Secondly, Assay $D_D$ as set forth under item 4.5.9.2 is conducted, and the obtained molar amount of the compound of the formula D-(II)(II)* is determined according to Assay $D_D$.

E-3. Then, step E-1 is repeated, except that instead of the addition of 400 nmol $E_Y$ in 0.1 ml aqueous phosphate buffer (pH 7.2, 10 mM MnCl$_2$), 0.1 ml aqueous phosphate buffer (pH 7.2, 10 mM MnCl$_2$) without $E_Y$ is added.

E-4 Then, step E-2 is repeated, except that instead of the addition of 400 nmol $E_Y$ in 0.1 ml aqueous phosphate buffer (pH 7.2, 10 mM MnCl$_2$), 0.1 ml aqueous phosphate buffer (pH 7.2, 10 mM MnCl$_2$) without $E_Y$ is added.

4.5.10.2 Hydantoinase Activity:

If the molar amount of the compound of the formula L-(II) (II)* that is determined in step E-1, is greater than the molar amount of the compound of formula L-(II)(II)* that is determined in step E-3, then $E_Y$ is deemed to have hydantoinase activity, and hence may be considered a hydantoinase $E_2$ in the context of the invention.

4.5.10.3 L-Hydantoinase Activity 4.5.10.3.1 L-Hydantoinases (i) If the molar amount of the compound of the formula L-(II)(II)* that is determined in step E-1, is greater than the molar amount of the compound of the formula L-(II)(II)* that is determined in step E-3, and (ii) if the molar amount of the compound of the formula D-(II)(II)* that is determined in step E-2, is greater than or the same as the molar amount of the compound of the formula D-(II)(II)* that is determined in step E-4, and (iii) if, in addition, the molar amount of the compound of the formula L-(II)(II)* that is determined in step E-1 is greater than the molar amount of the compound of the formula D-(II)(II)* that is determined in step E-2, then $E_Y$ is deemed to have L-hydantoinase activity, and hence may be considered an L-hydantoinase in the context of the invention. In this case, $E_Y$ is deemed to be "L-enantioselective" in the context of the invention.

For the sake of clarity, it is pointed out that condition (iii) is automatically fulfilled in those cases in which the molar amount of the compound of formula D-(II)(II)* that is determined in step E-2 is the same as the molar amount of the compound of formula D-(II)(II)* that is determined in step E-4.

(i) If the molar amount of the compound of formula L-(II) (II)* that is determined in step E-1, is greater than the molar amount of the compound of formula L-(II) (II)* that is determined in step E-3, and (ii) if the molar amount of the compound of the formula D-(II)(II)* that is determined in step E-2, is the same as the molar amount of the compound of the formula D-(II)(II)* that is determined in step E-4, then $E_Y$ is deemed to have L-hydantoinase activity, and hence may be considered a L-hydantoinase in the context of the invention. In this case, $E_Y$ is deemed to be not only "L-enantioselective", but also "L-enantiospecific" in the context of the invention.

For L-hydantoinases $E_Y$ that are not L-enantiospecific, the L-enantioselectivity may then be quantified by dividing the molar amount of the compound of formula L-(II)(II)* that is determined in E-1, by the molar amount of the compound of formula D-(II)(II)* that is determined in E-2, and then multiplying the obtained value by 100, giving the L-enantioselectivity of $E_Y$ in %.

4.5.10.3.2 D-Carbamoylases (i) If the molar amount of the compound of formula L-(II) (II)* that is determined in step E-1, is greater than or the same as the molar amount of the compound of formula L-(II)(II)* that is determined in step E-3, and (ii) if the molar amount of the compound of formula D-(II)(II)* that is determined in step E-2 is greater than the molar amount of the compound of formula D-(II) (II)* that is determined in step E-4, and (iii) if, in addition, the molar amount of the compound of formula D-(II)(II)* that is determined in step E-2, is greater than the molar amount of the compound of formula L-(II)(II)* that is determined in step E-1, then $E_Y$ is deemed to have D-hydantoinase activity, and hence may be considered a D-hydantoinase. In this case, $E_Y$ is "D-enantioselective" in the context of the invention.

For the sake of clarity it is pointed out that condition (iii) is automatically fulfilled in those cases in which the molar amount of the compound of formula L-(II)(II)* that is determined in step E-1 is the same as the molar amount of the compound of formula L-(II)(II)* that is determined in step E-3.

(i) If the molar amount of the compound of formula L-(II) (II)* that is determined in step E-1, is the same as the molar amount of the compound of formula L-(II) (II)* that is determined in step E-3, and (ii) if the molar amount of the compound of formula D-(II)(II)* that is determined in step E-2, is greater than the molar amount of the compound of formula D-(II) (II)* that is determined in step E-4, then $E_Y$ is deemed to have D-hydantoinase activity, and hence may be considered a D-hydantoinase in the context of the invention. In this case, $E_Y$ is deemed to be not only "D-enantioselective", but also "D-enantiospecific" in the context of the invention.

For D-hydantoinases $E_Y$ that are not D-enantiospecific, the D-enantioselectivity may then be quantified by dividing the molar amount of the compound of formula D-(II) (II)* that is determined in step E-2 by the molar amount of the compound of formula L-(II)(II)* that is determined in step E-1 and then multiplying the obtained value by 100, giving the D-enantioselectivity of $E_Y$ in %.

4.5.10.3.3 Non-Enantioselective Carbamoylases (i) If the molar amount of the compound of formula L-(II) (II)* that is determined in step E-1, is greater than the molar amount of the compound of formula L-(II) (II)* that is determined in step E-3, and (ii) if the molar amount of the compound of the formula D-(II)(II)* that is determined in step E-2, is greater than the molar amount of the compound of formula D-(II) (II)* that is determined in step E-4, and (iii) if, in addition, the molar amount of the compound of formula D-(II)(II)* that is determined in step E-2 is the same as the molar amount of the compound of formula L-(II)(II)* that is determined in step E-1, then $E_Y$ is deemed to be a non-enantioselective hydantoinase in the context of the invention. In this case, $E_Y$ is "non-enantioselective".

4.5.11 Assay F for Identifying Preferred Hydantoinases Variants of SEQ ID NOs: 10-16

4.5.11.1 L- and D-Enantioselective Hydantoinase Variants

An enzyme, the polypeptide sequence of which is selected from the group consisting of SEQ ID NO: 10, SEQ ID NO: 11, SEQ ID NO: 12, SEQ ID NO: 13, SEQ ID NO: 14, SEQ ID NO: 15, SEQ ID NO: 16 has hydantoinase, in particular L-hydantoinase activity.

In a preferred embodiment of the method according to the first aspect of the invention, the polypeptide sequence of the hydantoinase, in particular the L-hydantoinase $E_2$ is selected from the group consisting SEQ ID NO: 10 and variants thereof, SEQ ID NO: 11 and variants thereof, SEQ ID NO: 12 and variants thereof, SEQ ID NO: 13 and variants thereof, SEQ ID NO: 14, and variants thereof, SEQ ID NO: 15 and variants thereof, SEQ ID NO: 16 and variants thereof, more preferably SEQ ID NO: 10 and variants thereof.

The term "variant" is defined under item 4.3.

In the context of the invention, an enzyme, the polypeptide sequence of which is a variant of one of SEQ ID NO: 10, SEQ ID NO: 11, SEQ ID NO: 12, SEQ ID NO: 13, SEQ ID NO: 14, SEQ ID NO: 15, SEQ ID NO: 16, has hydantoinase activity, preferably L-hydantoinase activity, more preferably is L-enantiospecific.

Whether a given enzyme $E_Y$, the polypeptide sequence of which is a variant of one of SEQ ID NO: 10, SEQ ID NO: 11, SEQ ID NO: 12, SEQ ID NO: 13, SEQ ID NO: 14, SEQ ID NO: 15, SEQ ID NO: 16, has hydantoinase activity, L-hydantoinase activity and is L-enantiospecific may be determined as set forth under items 4.5.10.2 and 4.5.10.3.1, respectively.

The hydantoinase activity of a given hydantoinase $E_{2V}$, the polypeptide sequence of which is a variant of one of SEQ ID NO: 10, SEQ ID NO: 11, SEQ ID NO: 12, SEQ ID NO: 13, SEQ ID NO: 14, SEQ ID NO: 15, SEQ ID NO: 16, relative to the hydantoinase activity of an hydantoinase $E_{2S}$, wherein the polypeptide sequence of $E_{2S}$ is selected from SEQ ID NO: 10, SEQ ID NO: 11, SEQ ID NO: 12, SEQ ID NO: 13, SEQ ID NO: 14, SEQ ID NO: 15, SEQ ID NO: 16, may be determined in the context of the present invention by the following Assay F:

4.5.11.2 Assay F

F-1 Assay $D_L$ as set forth under item 4.5.9.1 is conducted, wherein $E_{2S}$ is the enzyme to be tested. The obtained molar amount of the compound according to formula L-(II)(II)* is determined according to Assay $D_L$.

F-2 Step F-1 is repeated, except that, instead of $E_{2S}$, $E_{2V}$ is used as the enzyme to be tested.

F-3. Then, the molar amount of the compound according to formula L-(II)(II)* that is determined in step F-2, is divided by the molar amount of the compound according to formula L-(II)(II)* that is determined in step F-1, and the obtained ratio is multiplied by 100, giving the hydantoinase activity of hydantoinase $E_{2V}$ relative to the hydantoinase activity of the hydantoinase $E_{2S}$, in %.

4.5.12 Preferred Hydantoinase Variants of SEQ ID NOs: 10-16

In the context of the invention, hydantoinases $E_2$, the polypeptide sequence of which is selected from the group consisting of SEQ ID NO: 10, SEQ ID NO: 11; SEQ ID NO: 12, SEQ ID NO: 13, SEQ ID NO: 14, SEQ ID NO: 15, SEQ ID NO: 16, are generally denoted as "$E_{2S}$". Hydantoinases $E_2$, the polypeptide sequence of which is selected from variants of a sequence selected from the group consisting of SEQ ID NO: 10, SEQ ID NO: 11; SEQ ID NO: 12, SEQ ID NO: 13, SEQ ID NO: 14, SEQ ID NO: 15, SEQ ID NO: 16, are generally denoted as "$E_{2V}$".

In a preferred embodiment of the method according to the first aspect of the present invention, the reaction in step (b) is catalyzed by a hydantoinase $E_2$, preferably an L-hydantoinase $E_2$, and the polypeptide sequence of the hydantoinase $E_2$, preferably the L-hydantoinase $E_2$, is selected from the group consisting of SEQ ID NO: 10 and variants thereof, SEQ ID NO: 11 and variants thereof, SEQ ID NO: 12 and variants thereof, SEQ ID NO: 13 and variants thereof, SEQ ID NO: 14 and variants thereof, SEQ ID NO: 15 and variants thereof, SEQ ID NO: 16 and variants thereof. More preferably, the reaction in step (b) is catalyzed by a hydantoinase $E_2$, preferably an L-hydantoinase $E_2$, and the polypeptide sequence of the hydantoinase $E_2$, preferably the L-hydantoinase $E_2$, is selected from the group consisting of SEQ ID NO: 10 and variants of SEQ ID NO: 10.

4.5.12.1 Preferred Variants of SEQ ID NO: 10

According to the invention, the polypeptide sequence of the hydantoinase $E_2$, preferably the polypeptide sequence of the L-hydantoinase $E_2$, may also be a variant of SEQ ID NO: 10.

The hydantoinase $E_2$, the polypeptide sequence of which is SEQ ID NO: 10, is denoted as "$E_{210S}$". The hydantoinase $E_2$, the polypeptide sequence of which is selected from variants of SEQ ID NO: 10, are generally denoted as "$E_{210V}$".

A variant of the polypeptide sequence of SEQ ID NO: 10 is a polypeptide with sequence identity of at least 60%, preferably ≥65%, more preferably ≥70%, more preferably ≥75%, more preferably ≥80%, more preferably ≥85%, more preferably ≥90%, more preferably ≥91%, more preferably ≥92%, more preferably ≥93%, more preferably ≥94%, more preferably ≥95%, more preferably ≥96%, more preferably ≥97%, more preferably ≥98%, more preferably ≥99%, more preferably ≥99.9% sequence identity to polypeptide sequence SEQ ID NO: 10.

The polypeptide sequence of a variant of the polypeptide sequence SEQ ID NO: 10 is not identical to SEQ ID NO: 10.

According to the invention, a hydantoinase $E_{210V}$ has hydantoinase activity and preferably L-hydantoinase activity, determined as described under items 4.5.10.2 and 4.5.10.3.1.

According to the invention, a hydantoinase $E_{210V}$ preferably has hydantoinase activity of at least 1%, preferably of at least 10%, more preferably of at least 20%, more preferably of at least 30%, more preferably of at least 40%, more preferably of at least 50%, more preferably of at least 60%, more preferably of at least 70%, more preferably of at least 80%, more preferably of at least 90%, more preferably of at least 99%, more preferably of at least 100% the hydantoinase activity of the hydantoinase $E_{210S}$, wherein the hydantoinase activity of $E_{210V}$, relative to the hydantoinase activity of $E_{210S}$ is determined by Assay F described under item 4.5.11.2.

It is even more preferably according to the invention, that a hydantoinase $E_{210V}$ has hydantoinase activity in the range of 1 to 1000%, preferably in the range of 5 to 500%, more preferably in the range of 10 to 400%, more preferably in the range of 40 to 200%, more preferably in the range of 50 to 150%, more preferably in the range of 60 to 140%, more preferably in the range of 70 to 130%, more preferably in the range of 80 to 120%, more preferably in the range of 90 to 110%, more preferably 100% the hydantoinase activity of the hydantoinase $E_{210S}$, wherein the hydantoinase activity of $E_{210V}$, relative to the hydantoinase activity $E_{210S}$ is determined by Assay F described under item 4.5.11.2.

4.5.12.2 Preferred Variants of SEQ ID NO: 11

According to the invention, the polypeptide sequence of the hydantoinase $E_2$, preferably the polypeptide sequence of the L-hydantoinase $E_2$, may also be a variant of SEQ ID NO: 11.

The hydantoinase $E_2$, the polypeptide sequence of which is SEQ ID NO: 11, is denoted as "$E_{211S}$". The hydantoinase $E_2$, the polypeptide sequence of which is selected from variants of SEQ ID NO: 11, are generally denoted as "$E_{211V}$".

A variant of the polypeptide sequence of SEQ ID NO: 11 is a polypeptide with sequence identity of at least 60%, preferably ≥65%, more preferably ≥70%, more preferably ≥75%, more preferably ≥80%, more preferably ≥85%, more preferably ≥90%, more preferably ≥91%, more preferably ≥92%, more preferably ≥93%, more preferably ≥94%, more preferably ≥95%, more preferably ≥96%, more preferably ≥97%, more preferably ≥98%, more preferably ≥99%, more preferably ≥99.9% sequence identity to polypeptide sequence SEQ ID NO: 11.

The polypeptide sequence of a variant of the polypeptide sequence SEQ ID NO: 11 is not identical to SEQ ID NO: 11.

According to the invention, a hydantoinase $E_{211V}$ has hydantoinase activity and preferably L-hydantoinase activity, determined as described under items 4.5.10.2 and 4.5.10.3.1.

According to the invention, a hydantoinase $E_{211V}$ preferably has hydantoinase activity of at least 1%, preferably of at least 10%, more preferably of at least 20%, more preferably of at least 30%, more preferably of at least 40%, more preferably of at least 50%, more preferably of at least 60%, more preferably of at least 70%, more preferably of at least 80%, more preferably of at least 90%, more preferably of at least 99%, more preferably of at least 100% the hydantoinase activity of the hydantoinase $E_{211S}$, wherein the hydantoinase activity of $E_{211V}$, relative to the hydantoinase activity of $E_{211S}$ is determined by Assay F described under item 4.5.11.2.

It is even more preferably according to the invention, that a hydantoinase $E_{211V}$ has hydantoinase activity in the range of 1 to 1000%, preferably in the range of 5 to 500%, more preferably in the range of 10 to 400%, more preferably in the range of 40 to 200%, more preferably in the range of 50 to 150%, more preferably in the range of 60 to 140%, more preferably in the range of 70 to 130%, more preferably in the range of 80 to 120%, more preferably in the range of 90 to 110%, more preferably 100% the hydantoinase activity of the hydantoinase $E_{211S}$, wherein the hydantoinase activity of $E_{211V}$, relative to the hydantoinase activity $E_{211S}$ is determined by Assay F described under item 4.5.11.2.

4.5.12.3 Preferred Variants of SEQ ID NO: 12

According to the invention, the polypeptide sequence of the hydantoinase $E_2$, preferably the polypeptide sequence of the L-hydantoinase $E_2$, may also be a variant of SEQ ID NO: 12.

The hydantoinase $E_2$, the polypeptide sequence of which is SEQ ID NO: 12, is denoted as "$E_{212S}$". The hydantoinase $E_2$, the polypeptide sequence of which is selected from variants of SEQ ID NO: 12, are generally denoted as "$E_{212V}$".

A variant of the polypeptide sequence of SEQ ID NO: 12 is a polypeptide with sequence identity of at least 60%, preferably ≥65%, more preferably ≥70%, more preferably ≥75%, more preferably ≥80%, more preferably ≥85%, more preferably ≥90%, more preferably ≥91%, more preferably ≥92%, more preferably ≥93%, more preferably ≥94%, more preferably ≥95%, more preferably ≥96%, more preferably ≥97%, more preferably ≥98%, more preferably ≥99%, more preferably ≥99.9% sequence identity to polypeptide sequence SEQ ID NO: 12.

The polypeptide sequence of a variant of the polypeptide sequence SEQ ID NO: 12 is not identical to SEQ ID NO: 12.

According to the invention, a hydantoinase $E_{212V}$ has hydantoinase activity and preferably L-hydantoinase activity, determined as described under items 4.5.10.2 and 4.5.10.3.1.

According to the invention, a hydantoinase $E_{212V}$ preferably has hydantoinase activity of at least 1%, preferably of at least 10%, more preferably of at least 20%, more preferably of at least 30%, more preferably of at least 40%, more preferably of at least 50%, more preferably of at least 60%, more preferably of at least 70%, more preferably of at least 80%, more preferably of at least 90%, more preferably of at least 99%, more preferably of at least 100% the hydantoinase activity of the hydantoinase $E_{212S}$, wherein the hydantoinase activity of $E_{212V}$, relative to the hydantoinase activity of $E_{212S}$ is determined by Assay F described under item 4.5.11.2.

It is even more preferably according to the invention, that a hydantoinase $E_{212V}$ has hydantoinase activity in the range of 1 to 1000%, preferably in the range of 5 to 500%, more preferably in the range of 10 to 400%, more preferably in the range of 40 to 200%, more preferably in the range of 50 to 150%, more preferably in the range of 60 to 140%, more preferably in the range of 70 to 130%, more preferably in the range of 80 to 120%, more preferably in the range of 90 to 110%, more preferably 100% the hydantoinase activity of the hydantoinase $E_{212S}$, wherein the hydantoinase activity of $E_{212V}$, relative to the hydantoinase activity $E_{212S}$ is determined by Assay F described under item 4.5.11.2.

4.5.12.4 Preferred Variants of SEQ ID NO: 13

According to the invention, the polypeptide sequence of the hydantoinase $E_2$, preferably the polypeptide sequence of the L-hydantoinase $E_2$, may also be a variant of SEQ ID NO: 13.

The hydantoinase $E_2$, the polypeptide sequence of which is SEQ ID NO: 13, is denoted as "$E_{213S}$". The hydantoinase $E_2$, the polypeptide sequence of which is selected from variants of SEQ ID NO: 13, are generally denoted as "$E_{213V}$".

A variant of the polypeptide sequence of SEQ ID NO: 13 is a polypeptide with sequence identity of at least 60%, preferably ≥65%, more preferably ≥70%, more preferably ≥75%, more preferably ≥80%, more preferably ≥85%, more preferably ≥90%, more preferably ≥91%, more preferably ≥92%, more preferably ≥93%, more preferably ≥94%, more preferably ≥95%, more preferably ≥96%, more preferably ≥97%, more preferably ≥98%, more preferably ≥99%, more preferably ≥99.9% sequence identity to polypeptide sequence SEQ ID NO: 13.

The polypeptide sequence of a variant of the polypeptide sequence SEQ ID NO: 13 is not identical to SEQ ID NO: 13.

According to the invention, a hydantoinase $E_{213V}$ has hydantoinase activity and preferably L-hydantoinase activity, determined as described under items 4.5.10.2 and 4.5.10.3.1.

According to the invention, a hydantoinase $E_{213V}$ preferably has hydantoinase activity of at least 1%, preferably of at least 10%, more preferably of at least 20%, more preferably of at least 30%, more preferably of at least 40%, more preferably of at least 50%, more preferably of at least 60%, more preferably of at least 70%, more preferably of at least 80%, more preferably of at least 90%, more preferably of at least 99%, more preferably of at least 100% the hydantoinase activity of the hydantoinase $E_{213S}$, wherein the hydantoinase activity of $E_{213V}$, relative to the hydantoinase activity of $E_{213S}$ is determined by Assay F described under item 4.5.11.2.

It is even more preferably according to the invention, that a hydantoinase $E_{213V}$ has hydantoinase activity in the range of 1 to 1000%, preferably in the range of 5 to 500%, more preferably in the range of 10 to 400%, more preferably in the range of 40 to 200%, more preferably in the range of 50 to 150%, more preferably in the range of 60 to 140%, more preferably in the range of 70 to 130%, more preferably in the range of 80 to 120%, more preferably in the range of 90 to 110%, more preferably 100% the hydantoinase activity of the hydantoinase $E_{213S}$, wherein the hydantoinase activity of $E_{213V}$, relative to the hydantoinase activity $E_{213S}$ is determined by Assay F described under item 4.5.11.2.

4.5.12.5 Preferred Variants of SEQ ID NO: 14

According to the invention, the polypeptide sequence of the hydantoinase $E_2$, preferably the polypeptide sequence of the L-hydantoinase $E_2$, may also be a variant of SEQ ID NO: 14.

The hydantoinase $E_2$, the polypeptide sequence of which is SEQ ID NO: 14, is denoted as "$E_{214S}$". The hydantoinase $E_2$, the polypeptide sequence of which is selected from variants of SEQ ID NO: 14, are generally denoted as "$E_{214V}$".

A variant of the polypeptide sequence of SEQ ID NO: 14 is a polypeptide with sequence identity of at least 60%, preferably ≥65%, more preferably ≥70%, more preferably ≥75%, more preferably ≥80%, more preferably ≥85%, more preferably ≥90%, more preferably ≥91%, more preferably ≥92%, more preferably ≥93%, more preferably ≥94%, more preferably ≥95%, more preferably ≥96%, more preferably ≥97%, more preferably ≥98%, more preferably ≥99%, more preferably ≥99.9% sequence identity to polypeptide sequence SEQ ID NO: 14.

The polypeptide sequence of a variant of the polypeptide sequence SEQ ID NO: 14 is not identical to SEQ ID NO: 14.

According to the invention, a hydantoinase $E_{214V}$ has hydantoinase activity and preferably L-hydantoinase activity, determined as described under items 4.5.10.2 and 4.5.10.3.1.

According to the invention, a hydantoinase $E_{214V}$ preferably has hydantoinase activity of at least 1%, preferably of at least 10%, more preferably of at least 20%, more preferably of at least 30%, more preferably of at least 40%, more preferably of at least 50%, more preferably of at least 60%, more preferably of at least 70%, more preferably of at least 80%, more preferably of at least 90%, more preferably of at least 99%, more preferably of at least 100% the hydantoinase activity of the hydantoinase $E_{214S}$, wherein the hydantoinase activity of $E_{214V}$, relative to the hydantoinase activity of $E_{214S}$ is determined by Assay F described under item 4.5.11.2.

It is even more preferably according to the invention, that a hydantoinase $E_{214V}$ has hydantoinase activity in the range of 1 to 1000%, preferably in the range of 5 to 500%, more preferably in the range of 10 to 400%, more preferably in the range of 40 to 200%, more preferably in the range of 50 to 150%, more preferably in the range of 60 to 140%, more preferably in the range of 70 to 130%, more preferably in the range of 80 to 120%, more preferably in the range of 90 to 110%, more preferably 100% the hydantoinase activity of the hydantoinase $E_{214S}$, wherein the hydantoinase activity of $E_{214V}$, relative to the hydantoinase activity $E_{214S}$ is determined by Assay F described under item 4.5.11.2.

4.5.12.6 Preferred Variants of SEQ ID NO: 15

According to the invention, the polypeptide sequence of the hydantoinase $E_2$, preferably the polypeptide sequence of the L-hydantoinase $E_2$, may also be a variant of SEQ ID NO: 15.

The hydantoinase $E_2$, the polypeptide sequence of which is SEQ ID NO: 15, is denoted as "$E_{215S}$". The hydantoinase $E_2$, the polypeptide sequence of which is selected from variants of SEQ ID NO: 15, are generally denoted as "$E_{215V}$".

A variant of the polypeptide sequence of SEQ ID NO: 15 is a polypeptide with sequence identity of at least 60%, preferably ≥65%, more preferably ≥70%, more preferably ≥75%, more preferably ≥80%, more preferably ≥85%, more preferably ≥90%, more preferably ≥91%, more preferably ≥92%, more preferably ≥93%, more preferably ≥94%, more preferably ≥95%, more preferably ≥96%, more preferably ≥97%, more preferably ≥98%, more preferably ≥99%, more preferably ≥99.9% sequence identity to polypeptide sequence SEQ ID NO: 15.

The polypeptide sequence of a variant of the polypeptide sequence SEQ ID NO: 15 is not identical to SEQ ID NO: 15.

According to the invention, a hydantoinase $E_{215V}$ has hydantoinase activity and preferably L-hydantoinase activity, determined as described under items 4.5.10.2 and 4.5.10.3.1.

According to the invention, a hydantoinase $E_{215V}$ preferably has hydantoinase activity of at least 1%, preferably of at least 10%, more preferably of at least 20%, more preferably of at least 30%, more preferably of at least 40%, more preferably of at least 50%, more preferably of at least 60%, more preferably of at least 70%, more preferably of at least 80%, more preferably of at least 90%, more preferably of at least 99%, more preferably of at least 100% the hydantoinase activity of the hydantoinase $E_{215S}$, wherein the hydantoinase activity of $E_{215V}$, relative to the hydantoinase activity of $E_{215S}$ is determined by Assay F described under item 4.5.11.2.

It is even more preferably according to the invention, that a hydantoinase $E_{215V}$ has hydantoinase activity in the range of 1 to 1000%, preferably in the range of 5 to 500%, more preferably in the range of 10 to 400%, more preferably in the range of 40 to 200%, more preferably in the range of 50 to 150%, more preferably in the range of 60 to 140%, more preferably in the range of 70 to 130%, more preferably in the range of 80 to 120%, more preferably in the range of 90 to 110%, more preferably 100% the hydantoinase activity of the hydantoinase $E_{215S}$, wherein the hydantoinase activity of $E_{215V}$, relative to the hydantoinase activity $E_{215S}$ is determined by Assay F described under item 4.5.11.2.

4.5.12.7 Preferred Variants of SEQ ID NO: 16

According to the invention, the polypeptide sequence of the hydantoinase $E_2$, preferably the polypeptide sequence of the L-hydantoinase $E_2$, may also be a variant of SEQ ID NO: 16.

The hydantoinase $E_2$, the polypeptide sequence of which is SEQ ID NO: 16, is denoted as "$E_{216S}$". The hydantoinase $E_2$, the polypeptide sequence of which is selected from variants of SEQ ID NO: 16, are generally denoted as "$E_{216V}$".

A variant of the polypeptide sequence of SEQ ID NO: 16 is a polypeptide with sequence identity of at least 60%, preferably ≥65%, more preferably ≥70%, more preferably ≥75%, more preferably ≥80%, more preferably ≥85%, more preferably ≥90%, more preferably ≥91%, more preferably ≥92%, more preferably ≥93%, more preferably ≥94%, more preferably ≥95%, more preferably ≥96%, more preferably ≥97%, more preferably ≥98%, more preferably ≥99%, more preferably ≥99.9% sequence identity to polypeptide sequence SEQ ID NO: 16.

The polypeptide sequence of a variant of the polypeptide sequence SEQ ID NO: 16 is not identical to SEQ ID NO: 16.

According to the invention, a hydantoinase $E_{216V}$ has hydantoinase activity and preferably L-hydantoinase activity, determined as described under items 4.5.10.2 and 4.5.10.3.1.

According to the invention, a hydantoinase $E_{216V}$ preferably has hydantoinase activity of at least 1%, preferably of at least 10%, more preferably of at least 20%, more preferably of at least 30%, more preferably of at least 40%, more preferably of at least 50%, more preferably of at least 60%, more preferably of at least 70%, more preferably of at least 80%, more preferably of at least 90%, more preferably of at least 99%, more preferably of at least 100% the hydantoinase activity of the hydantoinase $E_{216S}$, wherein the hydantoinase activity of $E_{216V}$, relative to the hydantoinase activity of $E_{216S}$ is determined by Assay F described under item 4.5.11.2.

It is even more preferably according to the invention, that a hydantoinase $E_{216V}$ has hydantoinase activity in the range of 1 to 1000%, preferably in the range of 5 to 500%, more preferably in the range of 10 to 400%, more preferably in the range of 40 to 200%, more preferably in the range of 50 to 150%, more preferably in the range of 60 to 140%, more preferably in the range of 70 to 130%, more preferably in the range of 80 to 120%, more preferably in the range of 90 to 110%, more preferably 100% the hydantoinase activity of the hydantoinase $E_{216S}$, wherein the hydantoinase activity of $E_{216V}$, relative to the hydantoinase activity $E_{216S}$ is determined by Assay F described under item 4.5.11.2.

4.5.13 Preferred Method Conditions in Step (b)

The reaction in step (b) of the method according to the first aspect of the present invention may be carried out under conditions known to the skilled person.

The reaction medium is preferably aqueous, more preferably an aqueous buffer.

Exemplary buffers commonly used in biotransformation reactions and advantageously used herein include Tris, phosphate, or any of Good's buffers, such as 2-(N-morpholino)ethanesulfonic acid ("MES"), N-(2-acetamido)iminodiacetic acid ("ADA"), piperazine-N,N'-bis(2-ethanesulfonic acid) ("PIPES"), N-(2-acetamido)-2-aminoethanesulfonic acid ("ACES"), P-hydroxy-4-morpholinepropanesulfonic acid ("MOPSO"), cholamine chloride, 3-(N-morpholino)propanesulfonic acid ("MOPS"), N, N-Bis(2-hydroxyethyl)-2-aminoethanesulfonic acid ("BES"), 2-[[1,3-dihydroxy-2-(hydroxymethyl) propan-2-yl]amino]ethanesulfonic acid ("TES"), 4-(2-hydroxyethyl)-1-piperazineethanesulfonic acid ("HEPES"), 3-(Bis(2-hydroxyethyl)amino)-2-hydroxypropane-1-sulfonic acid ("DIPSO"), acetamidoglycine, 3-(N-Tris(hydroxymethyl)methylamino(-2-hydroxypropane) sulfonic acid ("TAPSO"), piperazine-N,N'-bis(2-hydroxypropanesulfonic acid) ("POPSO"), 4-(2-Hydroxyethyl) piperazine-1-(2-hydroxypropanesulfonic acid) ("HEPPSO"), 3-[4-(2-Hydroxyethyl)-1-piperazinyl]propanesulfonic acid ("HEPPS"), tricine, glycinamide, bicine, or 3-[[1,3-dihydroxy-2-(hydroxymethyl) propan-2-yl]amino]propane-1-sulfonic acid ("TAPS").

In some embodiments, ammonium can act as a buffer. One or more organic solvents can also be added to the reaction.

The buffer preferably contains metal salts, more preferably metal salts such as halogenides of metals, preferably halogenides of monovalent or bivalent or trivalent metals, preferably chlorides of monovalent or bivalent metals, preferably $CoCl_2$ or $MnCl_2$, preferably $CoCl_2$.

The concentration of these metal salts in the reaction medium is preferably in the range from 1 µM to 1 M, more preferably 1 mM to 100 mM, even more preferably 1 to 10 mM.

Preferably, step (b) of the method according to the first aspect of the invention is carried out in a phosphate buffer.

The pH of the reaction medium in step (b) of the method according to the first aspect of the invention is preferably in the range of from 2 to 10, more preferably in the range of from 5 to 8, more preferably 7.2 to 7.5, most preferably 7.5.

Preferably, step (b) of the method according to the first aspect of the invention is carried out at a temperature in the range of from 20° C. to 70° C., more preferably in the range of from 30° C. to 55° C., most preferably 50° C.

Preferably, the total concentration of all hydantoinases $E_2$ in the reaction solution in step (b) is in the range of from 1 µM to 10 mM, preferably 10 µM to 1 mM, more preferably 0.1 mM to 0.5 mM, most preferably 0.4 mM.

In alternative preferred embodiments, the total concentration of all hydantoinases $E_2$ in the reaction solution in step (b) is in the range of from 1 µg/l to 10 g/l, preferably 0.1 mg/l to 5 g/l, more preferably 1 mg/l to 1 g/l, more preferably 5 mg/l to 500 mg/l.

Preferably, the initial concentration of all the compounds according to formula L-(III) in the reaction medium in step (b) is in the range of from 1 µM to 1 M, preferably of from 10 µM to 0.5 M, more preferably of from 0.1 mM to 0.1 M, more preferably of from 1 mM to 10 mM, most preferably 1.25 mM.

If compounds according to formula D-(III) are present in the reaction medium in step (b), the initial concentration of all the compounds according to formula D-(III) in the reaction medium is preferably from 1% to 100% the concentration of all the compounds according to formula L-(III), more preferably 10% to 100% the concentration, even more preferably 50 to 100%, even more preferably 100% the concentration of all the compounds according to formula L-(III).

Preferably, step (b) is carried out in the same reaction medium in which step (c) is carried out.

In this case, preferably, the initial concentration of all the compounds according to formula L-(III) in the reaction medium in step (b) is in the range of from 1 µM to 1 M, preferably of from 10 µM to 0.5 M, more preferably of from 0.1 mM to 0.1 M, more preferably of from 1 mM to 10 mM, most preferably 1.25 mM.

"Initial concentration of all the compounds according to formula L-(III)/D-(III)" refers to the concentration of the respective compound L-(III) or D-(III), respectively, in the reaction medium when the respective compounds are employed in step (b).

4.5.14 Step (a)

In a preferred embodiment of the method according to the first aspect of the invention, the compound according to formula L-(III) is obtained by a step (a) in which a compound according to formula D-(III) is reacted to give a compound according to formula L-(III):

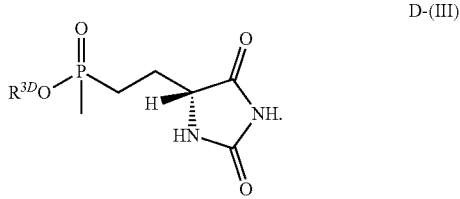

D-(III)

Step (a) gives the starting material for step (b).

$R^{3D}$ is a radical selected from the above-mentioned formulae (VIII), (IX), (X), preferably selected from the formulae (VIII), (IX), more preferably $R^{3D}$ has formula (VIII).

When $R^{3D}$ is a radical of the formula (VIII), the radical $R^{3D}$ may be selected from the above-mentioned formulae L-(VIII) and D-(VIII), preferably L-(VIII).

When $R^{3D}$ is a radical of the formula (IX), the radical $R^{3D}$ may be selected from the above-mentioned formulae L-(IX) and D-(IX), preferably L-(IX).

When $R^{3D}$ is a radical of the formula (X), the radical $R^{3D}$ may be selected from the above-mentioned formulae L-(X) and D-(X), preferably L-(X).

The reaction according step (a) may be carried out enzymatically or non-enzymatically, preferably enzymatically. More preferably, the reaction according step (a) is catalyzed by a hydantoin racemase $E_3$.

In preferred step (a), the compound according to formula D-(III) is employed in step (a) as a mixture $M_{III}$ of at least one compound D-(III) with at least one compound L-(III), wherein $R^{3L}=R^{3D}$.

In a preferred embodiment, the molar ratio of all compounds according to formula L-(III) in the mixture $M_{III}$ to all compounds according to formula D-(III) in the mixture $M_{III}$ is essentially 1:1.

In other preferred embodiments, the molar ratio of all compounds according to formula L-(III) in the mixture $M_{II}$ to all compounds according to formula D-(III) in the mixture $M_{III}$ is in the range of from 3:2 to 1:99, more preferably in the range of from 1.01:1 to 1:99, more preferably in the range of from 1:1 to 1:99, more preferably in the range of from 1:1.01 to 1:99, more preferably in the range of from 1:1.01 to 1:9, more preferably in the range of from 1:1.01 to 1:8, more preferably in the range of from 1:1.01 to 1:3.

Alternatively, D-(III) is comprised in an excess to L-(III) in mixture Mm, meaning that, while at least one compound according to formula L-(III) in the mixture $M_{III}$ to all compounds according to formula D-(III) in the mixture $M_{III}$ is <1:1, preferably <0.9:1, more preferably <0.75:1, more preferably <0.5:1, more preferably <0.2:1, more preferably <0.1:1, more preferably <0.01:1.

4.5.14.1 Step (a) without Enzymatic Catalysis

Step (a) may be carried out non-enzymatically, i.e. without the use of an enzyme. The reaction of compounds according to step D-(III) to compounds according to L-(III) proceeds in alkaline solution, as known to the skilled person and as described by Slomka et al., M. Bovarnick & H. T. Clarke, Journal of the American Chemical Society 1938, 60, 2426-2430, by R. A. Lazarus, J. Org. Chem. 1990, 55, 4755-4757, and by A. S. Bommarius, M. Kottenhahn, H. Klenk, K. Drauz: "A direct route from hydantoins to D-amino acids employing a resting cell biocatalyst with D-hydantoinase and D-carbamoylase acitivity" on page 164 and 167 in "Microbial Reagents in Organic Synthesis" Series C: Mathematical and Physical Sciences-Vol. 381, S. Servi (Ed.), 1992, Springer Science+Business Media, B. V., Dordrecht.

Therefore, if step (a) is carried out non-enzymatically, the conditions that are preferably applied in the reaction medium in which non-enzymatic step (a) is carried out are preferably those that are described for the preferred conditions for step (b) (item 4.5.13), except that the pH is ≥8, preferably in the range of 8 to 12, more preferably 8 to 11, more preferably 8 to 10, even more preferably 8 to 9. As in these embodiments, the preferred conditions in step (a) and (b) with respect to the pH ranges are different, it is preferable that the reaction media in steps (a) and (b) are different.

4.5.14.2 Enzymatic Conversion of D-(III) into L-(III)

Step (a) is preferably carried out enzymatically, i.e. the reaction according to step (a) is preferably catalyzed by a hydantoin racemase $E_3$.

Namely, it was surprisingly found that hydantoin racemases accept compounds of formula D-(III) as substrates and convert them to products according to formulae L-(III), and hence catalyze the reaction according to step (a), while there is no catalysis of the corresponding compound according to formula D-(III), in which R=H.

This finding is of high scientific and economic value, as it further expands the scope of new starting materials for the production of L-glufosinate alkyl esters and L-glufosinate via new synthetic routes. Moreover, this finding also opens new possibilities of enantioselective production of LGA from racemic mixtures of L-(III) and D-(III), as embodied in the method according to the second aspect of the invention.

In nature, hydantoin racemases catalyze the conversion of one of the two hydantoin enantiomers $H_L$ and $H_R$ into the other (see the following reaction <3>):

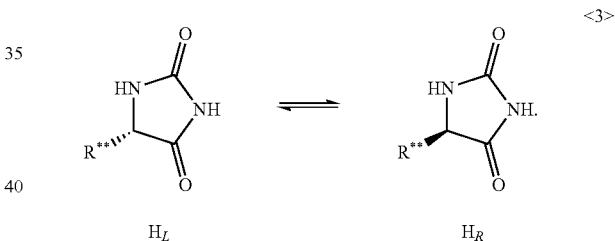

It was now surprisingly found that hydantoin racemases also accept substrates in which $R^{**}=R^Y=$

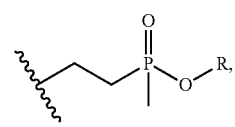

wherein $R=R^{3D}$.

Surprisingly, they do not accept substrates in which $R^{**}=R^Y=$

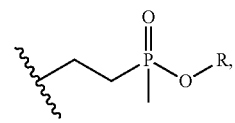

wherein R=H.

Suitable hydantoin racemases are described e.g. in WO 01/23582 A1 and by U. Engel, J. Rudat, C. Syldatk in "The hydantoinase process: recent developments for the production of non-canonical amino acids" in the book "Industrial biocatalysis" by P. Grunwald (Ed.), Pan Stanford Series on Biocatalysis, 2015, pages 817-862, and by F. J. Las Heras-Vazquez, J. M. Clemente-Jimenez, S. Martinez-Rodriguez, F. Rodriguez-Vico in "Hydantoin racemase: the key enzyme for the production of optically pure α-amino acids" in chapter 12 of the book "Modern Biocatalysis: Stereoselective and environmentally friendly reactions" by W. Fessner, T. Anthonsen (Eds), Weinheim: WILEY-VCH Verlag Gmbh & Co, 2009, pages 173-193.

A hydantoin racemase $E_3$ that may be used in optional step (a) of the method according to the first aspect of the invention may originate from *Agrobacterium* sp., in particular *Agrobacterium* strain IP_I-671; *Arthrobacter* sp., in particular *Arthrobacter aurescens*, more in particular *Arthrobacter aurescens* DSM 3745 or *Arthrobacter* sp. BT801; *Flavobacterium* sp., in particular *Flavobacterium* sp. AJ 11199; *Microbacterium* sp., in particular *Microbacterium liquefaciens*, preferably *Microbacterium liquefaciens* AJ 3912; *Pasteurella* sp., in particular *Pasteurella* sp. AJ11221; *Pseudomonas* sp., in particular *Pseudomonas* sp. NS671; *Pyrococcus* sp., in particular *Pyrococcus horikoshii* OT3; *Rhodococcus* sp., in particular *Rhodococcus* R04; *Sinorhizobium* sp., in particular *Sinorhizobium meliloti*, more in particular *Sinorhizobium meliloti* CECT 4114, most preferably from *Arthrobacter aurescens* DSM 3745.

A hydantoin racemase $E_3$ suitable for the method according to the present invention may be the enzyme HyuR, which originates from *Arthrobacter aurescens* DSM 3745. Another enzyme may be selected from HyuE, Hyu2, HRase, HyuA, PH1054.

The hydantoin racemase $E_3$ that may preferably be used in preferred step (a) of the method according to the first aspect of the invention may be categorized in the EC class 5.1.99.5.

The following table 3 gives preferred examples for polypeptide sequences of hydantoin racemase $E_3$ that may be preferably used in step (a) of the method according to the first aspect of the invention. The genes encoding the respective hydantoin racemase $E_3$ and the respective accession code are indicated as far as known.

TABLE 3

Hydantoin Racemases (EC 5.1.99.5)

| Strain | Gene name | GenBank/UniProt accession | SEQ ID NO: of the polypeptide |
|---|---|---|---|
| *Arthrobacter aurescens* DSM 3745 | hyuR | | SEQ ID NO: 17 |
| *Pseudomonas* sp. NS671 | hyuE | Q00924 | SEQ ID NO: 18 |
| *Rhodococcus* R04 | hyu2 | | SEQ ID NO: 19 |
| *Microbacterium liquefaciens* AJ 3912 | "HRase" | | SEQ ID NO: 20 |
| *Sinorhizobium meliloti* CECT 4114 | hyuA | Q6TMG4 | SEQ ID NO: 21 |
| *Flavobacterium* sp. AJ11199 | "HRase" | | SEQ ID NO: 22 |
| *Agrobacterium* IP_I-671 | hyuA | | SEQ ID NO: 23 |
| *Pasteurella* sp. AJ 11221 | not assigned | | SEQ ID NO: 24 |
| *Pyrococcus horikoshii* OT3 | PH1054 | O58781 | SEQ ID NO: 25 |
| *Arthrobacter* sp. BT801 | hyuA | AAL55411 | SEQ ID NO: 26 |

In a preferred embodiment of the preferred method according to the second aspect of the present invention, the reaction according to step (a) is catalyzed by a hydantoin racemase $E_3$, wherein the polypeptide sequence of $E_3$ is selected from the group consisting of SEQ ID NO: 17 and variants thereof, SEQ ID NO: 18 and variants thereof, SEQ ID NO: 19 and variants thereof, SEQ ID NO: 20 and variants thereof, SEQ ID NO: 21 and variants thereof, SEQ ID NO: 22 and variants thereof, SEQ ID NO: 23 and variants thereof, SEQ ID NO: 24 and variants thereof, SEQ ID NO: 25 and variants thereof, SEQ ID NO: 26 and variants thereof.

4.5.14.3 Assay G for Determining Hydantoin Racemase Activity

The skilled person is aware of hydantoin racemases, that may be used in preferred step (a) of the method according to the first aspect of the invention.

In particular, Assay G, described in the following, may be used to determine hydantoin racemase activity of a given enzyme $E_Z$ and may advantageously be used according to the invention to determine carbamoylase and L-carbamoylase activity in variants of SEQ ID NO: 17, variants of variants of SEQ ID NO: 18, variants of SEQ ID NO: 19, variants of SEQ ID NO: 20, variants of SEQ ID NO: 21, variants of SEQ ID NO: 22, variants of variants of SEQ ID NO: 23, variants of SEQ ID NO: 24, variants of SEQ ID NO: 25, variants of SEQ ID NO: 26.

For the purpose of Assay G, the molar mass of the enzyme $E_Z$ to be tested is calculated as the molar mass of the polypeptide sequence of $E_Z$.

Moreover, a substrate according to formula D-(III), wherein $R^{3D}$=n-butyl, is used in Assay G so that there is only one chiral carbon atom in the substrate. The compound according to formula D-(III), wherein $R^{3D}$=n-butyl, is denoted as "D-(III)+".

A product according to formula L-(III), wherein $R^{3L}$=n-butyl, is detected in Assay G.

The compound according to formula L-(III), wherein $R^{3L}$=n-butyl, is denoted as "L-(III)+".

Assay G:

To 0.9 ml of an aqueous reaction solution (phosphate buffer, pH 7.2, 10 mM Mg$_2$Cl), containing 50 mM of the pure D-enantiomer of an n-butyl ester of hydantoin glufosinate of the formula D-(III) (II)* are added 400 nmol of $E_Z$ in 0.1 ml aqueous phosphate buffer (pH 7.2, 10 mM MnCl$_2$). The resulting solution is incubated at 25° C., and the pH is held at pH 7.2 by addition of 0.5 M. After 300 minutes, the reaction is stopped by addition of 2 M HCl to achieve a pH of 2.5. The molar amount of the L-enantiomer of formula L-(III)(II)* is measured, at least every 3 minutes (determination by LC-MS, e.g. by the LC-MS method described in the example section, item 5.4, for the detection of LGA).

4.5.14.4 Assay H for Identifying Hydantoin Racemases

Whether a given enzyme $E_Z$ may be considered a hydantoin racemase $E_3$, may be determined in the context of the present invention by the following Assay H:

H-1 Firstly, Assay G as set forth under item 4.5.14.3 is conducted, and the obtained molar amount of L-(III)(II)* is determined according to Assay G.

H-2 Then, step H-1 is repeated, except that instead of the addition of 400 nmol $E_Z$ in 0.1 ml aqueous phosphate buffer (pH 7.2, 10 mM MnCl$_2$), 0.1 ml aqueous phosphate buffer (pH 7.2, 10 mM MnCl$_2$) without $E_Z$ is added.

4.5.14.5 Hydantoin Racemase Activity

If the molar amount of the compound of formula L-(III) (II)* that is determined in step H-1 is greater than the molar amount of the compound of formula L-(III)(II)* that is determined in step H-2, then $E_Z$ is deemed to have hydantoin racemase activity, and hence may be considered a hydantoin racemase $E_3$ in the context of the invention.

4.5.14.6 Assay J for Identifying Preferred Hydantoin Racemase Variants of SEQ ID NO: 17-26

An enzyme, the polypeptide sequence of which is selected from the group consisting of SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, has hydantoin racemase activity.

In a preferred embodiment of the method according to the first aspect of the invention, the polypeptide sequence of the hydantoin racemase $E_3$ is selected from the group consisting of SEQ ID NO: 17 and variants thereof, SEQ ID NO: 18 and variants thereof, SEQ ID NO: 19 and variants thereof, SEQ ID NO: 20 and variants thereof, SEQ ID NO: 21 and variants thereof, SEQ ID NO: 22 and variants thereof, SEQ ID NO: 23 and variants thereof, SEQ ID NO: 24 and variants thereof, SEQ ID NO: 25 and variants thereof, SEQ ID NO: 26 and variants thereof.

The term "variant" is defined under item 4.3.

In the context of the invention, an enzyme, the polypeptide sequence of which is a variant of one of SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, has hydantoin racemase activity.

Whether a given enzyme $E_Z$, the polypeptide sequence of which is a variant of one SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, has hydantoin racemase activity may be determined as set forth under items 4.5.14.4 and 4.5.14.5.

The hydantoin racemase activity of a given hydantoin racemase $E_{3V}$, the polypeptide sequence of which is a variant of one of SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, relative to the hydantoin racemase activity of a hydantoin racemase $E_{3S}$, wherein the polypeptide sequence of $E_{3S}$ is selected from SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, may be quantified in the context of the present invention by the following Assay J.

Assay J:

J-1 Firstly, Assay G as set forth under item 4.5.14.3 is conducted, wherein $E_{3S}$ is the enzyme to be tested. The molar amount of the compound according to formula L-(III)(II)* is determined according to Assay G.

J-2 Step J-1 is repeated, except that, instead of $E_{3S}$, $E_{3V}$ is used as the enzyme to be tested.

J-3. Then, the molar amount of the compound according to formula L-(III)(II)* is determined in step J-2, is divided by the molar amount of the compound according to formula L-(III), wherein R=n-butyl, is determined in step J-1, and the obtained ratio is multiplied by 100, giving the hydantoin racemase activity of hydantoin racemase $E_{3V}$, relative to the hydantoin racemase activity of the hydantoin racemase $E_{3S}$, in %.

4.5.14.7 Preferred Hydantoin Racemase Variants SEQ ID NO: 17-26

In the context of the present invention, hydantoin racemase $E_3$, the polypeptide sequence of which is selected from the group consisting of SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, are generally denoted as "$E_{3S}$".

Hydantoin racemases $E_3$, the polypeptide sequence of which is selected from variants of a sequence selected from the group consisting of f SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, are generally denoted as "$E_{3V}$".

In a preferred embodiment of the method according to the first aspect of the present invention, the reaction in step (a) is catalyzed by a hydantoin racemase $E_3$, and the polypeptide sequence of the hydantoin racemase $E_3$ is selected from the group consisting of SEQ ID NO: 17 and variants thereof, SEQ ID NO: 18 and variants thereof, SEQ ID NO: 19 and variants thereof, SEQ ID NO: 20 and variants thereof, SEQ ID NO: 21 and variants thereof, SEQ ID NO: 22 and variants thereof, SEQ ID NO: 23 and variants thereof, SEQ ID NO: 24 and variants thereof, SEQ ID NO: 25 and variants thereof, SEQ ID NO: 26 and variants thereof. More preferably, the reaction in step (a) is catalyzed by a hydantoin racemase $E_3$, and the polypeptide sequence of the hydantoin racemase $E_3$ is selected from the group consisting of SEQ ID NO: 1 and variants of SEQ ID NO: 1.

4.5.14.7.1 Preferred Variants of SEQ ID NO: 17

According to the invention, the polypeptide sequence of the hydantoin racemase $E_3$ may also be a variant of SEQ ID NO: 17.

The hydantoin racemase $E_3$, the polypeptide sequence of which is SEQ ID NO: 17, is denoted as "$E_{317S}$". Hydantoin racemases $E_3$, the polypeptide sequence of which is selected from variants of SEQ ID NO: 17, are generally denoted as "$E_{317V}$".

A variant of the polypeptide sequence of SEQ ID NO: 17 is a polypeptide with sequence identity of at least 60%, preferably ≥65%, more preferably ≥70%, more preferably ≥75%, more preferably ≥80%, more preferably ≥85%, more preferably ≥90%, more preferably ≥91%, more preferably ≥92%, more preferably ≥93%, more preferably ≥94%, more preferably ≥95%, more preferably ≥96%, more preferably ≥97%, more preferably ≥98%, more preferably ≥99%, more preferably ≥99.9% sequence identity to polypeptide sequence SEQ ID NO: 17.

The polypeptide sequence of a variant of the polypeptide sequence SEQ ID NO: 17 is not identical to SEQ ID NO: 17.

According to the invention, a hydantoin racemase $E_{317V}$ has hydantoin racemase activity, determined as described under item 4.5.14.4 and 4.5.14.5.

According to the invention, a hydantoin racemase $E_{317V}$ preferably has hydantoin racemase activity of at least 1%, preferably of at least 10%, more preferably of at least 20%, more preferably of at least 30%, more preferably of at least 40%, more preferably of at least 50%, more preferably of at least 60%, more preferably of at least 70%, more preferably of at least 80%, more preferably of at least 90%, more preferably of at least 99%, more preferably of at least 100% the hydantoin racemase of the hydantoin racemase $E_{317S}$, wherein the hydantoin racemase activity of $E_{317V}$ relative to the hydantoin racemase activity $E_{317S}$ is determined by Assay J described under item 4.5.14.6.

It is even more preferably according to the invention, that a hydantoin racemase $E_{317V}$ has hydantoin racemase activity in the range of 1 to 1000%, preferably in the range of 5 to 500%, more preferably in the range of 10 to 400%, more preferably in the range of 40 to 200%, more preferably in the range of 50 to 150%, more prefab in the range of 60 to 140%, more preferably in the range of 70 to 130%, more preferably in the range of 80 to 120%, more preferably in the range of 90 to 110%, more preferably 100% the hydantoin racemase activity of the hydantoin racemase $E_{317S}$, wherein the hydantoin racemase activity of $E_{317V}$, relative to the hydantoin racemase activity of $E_{317S}$ is determined by Assay J described under item 4.5.14.6.

4.5.14.7.2 Preferred Variants of SEQ ID NO: 18

According to the invention, the polypeptide sequence of the hydantoin racemase $E_3$ may also be a variant of SEQ ID NO: 18.

The hydantoin racemase $E_3$, the polypeptide sequence of which is SEQ ID NO: 18, is denoted as "$E_{318S}$". Hydantoin racemases $E_3$, the polypeptide sequence of which is selected from variants of SEQ ID NO: 18, are generally denoted as "$E_{318V}$".

A variant of the polypeptide sequence of SEQ ID NO: 18 is a polypeptide with sequence identity of at least 60%, preferably ≥65%, more preferably ≥70%, more preferably ≥75%, more preferably ≥80%, more preferably ≥85%, more preferably ≥90%, more preferably ≥91%, more preferably ≥92%, more preferably ≥93%, more preferably ≥94%, more preferably ≥95%, more preferably ≥96%, more preferably ≥97%, more preferably ≥98%, more preferably ≥99%, more preferably ≥99.9% sequence identity to polypeptide sequence SEQ ID NO: 18.

The polypeptide sequence of a variant of the polypeptide sequence SEQ ID NO: 18 is not identical to SEQ ID NO: 18.

According to the invention, a hydantoin racemase $E_{318V}$ has hydantoin racemase activity, determined as described under item 4.5.14.4 and 4.5.14.5.

According to the invention, a hydantoin racemase $E_{318V}$ preferably has hydantoin racemase activity of at least 1%, preferably of at least 10%, more preferably of at least 20%, more preferably of at least 30%, more preferably of at least 40%, more preferably of at least 50%, more preferably of at least 60%, more preferably of at least 70%, more preferably of at least 80%, more preferably of at least 90%, more preferably of at least 99%, more preferably of at least 100% the hydantoin racemase of the hydantoin racemase $E_{318S}$, wherein the hydantoin racemase activity of $E_{318V}$, relative to the hydantoin racemase activity $E_{318S}$ is determined by Assay J described under item 4.5.14.6.

It is even more preferably according to the invention, that a hydantoin racemase $E_{318V}$ has hydantoin racemase activity in the range of 1 to 1000%, preferably in the range of 5 to 500%, more preferably in the range of 10 to 400%, more preferably in the range of 40 to 200%, more preferably in the range of 50 to 150%, more preferably in the range of 60 to 140%, more preferably in the range of 70 to 130%, more preferably in the range of 80 to 120%, more preferably in the range of 90 to 110%, more preferably 100% the hydantoin racemase activity of the hydantoin racemase $E_{318S}$, wherein the hydantoin racemase activity of $E_{318V}$, relative to the hydantoin racemase activity of $E_{318S}$ is determined by Assay J described under item 4.5.14.6.

4.5.14.7.3 Preferred Variants of SEQ ID NO: 19

According to the invention, the polypeptide sequence of the hydantoin racemase $E_3$ may also be a variant of SEQ ID NO: 19.

The hydantoin racemase $E_3$, the polypeptide sequence of which is SEQ ID NO: 19, is denoted as "$E_{319S}$". Hydantoin racemases $E_3$, the polypeptide sequence of which is selected from variants of SEQ ID NO: 19, are generally denoted as "$E_{319V}$".

A variant of the polypeptide sequence of SEQ ID NO: 19 is a polypeptide with sequence identity of at least 60%, preferably ≥65%, more preferably ≥70%, more preferably ≥75%, more preferably ≥80%, more preferably ≥85%, more preferably ≥90%, more preferably ≥91%, more preferably ≥92%, more preferably ≥93%, more preferably ≥94%, more preferably ≥95%, more preferably ≥96%, more preferably ≥97%, more preferably ≥98%, more preferably ≥99%, more preferably ≥99.9% sequence identity to polypeptide sequence SEQ ID NO: 19.

The polypeptide sequence of a variant of the polypeptide sequence SEQ ID NO: 19 is not identical to SEQ ID NO: 19.

According to the invention, a hydantoin racemase $E_{319V}$ has hydantoin racemase activity, determined as described under item 4.5.14.4 and 4.5.14.5.

According to the invention, a hydantoin racemase $E_{319V}$ preferably has hydantoin racemase activity of at least 1%, preferably of at least 10%, more preferably of at least 20%, more preferably of at least 30%, more preferably of at least 40%, more preferably of at least 50%, more preferably of at least 60%, more preferably of at least 70%, more preferably of at least 80%, more preferably of at least 90%, more preferably of at least 99%, more preferably of at least 100% the hydantoin racemase of the hydantoin racemase $E_{319S}$, wherein the hydantoin racemase activity of $E_{319V}$, relative to the hydantoin racemase activity $E_{319S}$ is determined by Assay J described under item 4.5.14.6.

It is even more preferably according to the invention, that a hydantoin racemase $E_{319V}$ has hydantoin racemase activity in the range of 1 to 1000%, preferably in the age of 5 to 500%, more preferably in the range of 10 to 400%, more preferably in the range of 40 to 200%, more preferably in the range of 50 to 150%, more preferably in the range of 0 to 140%, more preferably in the range of 70 to 130%, more preferably in the range of 80 to 120%, more preferably in the range of 90 to 110%, more preferably 100% the hydantoin racemase activity of the hydantoin racemase $E_{319S}$, wherein the hydantoin racemase activity of $E_{319V}$, relative to the hydantoin racemase activity of $E_{319S}$ is determined by Assay J described under item 4.5.14.6.

4.5.14.7.4 Preferred Variants of SEQ ID NO: 20

According to the invention, the polypeptide sequence of the hydantoin racemase $E_3$ may also be a variant of SEQ ID NO: 20.

The hydantoin racemase $E_3$, the polypeptide sequence of which is SEQ ID NO: 20, is denoted as "$E_{320S}$". Hydantoin racemases $E_3$, the polypeptide sequence of which is selected from variants of SEQ ID NO: 20, are generally denoted as "$E_{320V}$".

A variant of the polypeptide sequence of SEQ ID NO: 20 is a polypeptide with sequence identity of at least 60%, preferably ≥65%, more preferably ≥70%, more preferably ≥75%, more preferably ≥80%, more preferably ≥85%, more preferably ≥90%, more preferably ≥91%, more preferably ≥92%, more preferably ≥93%, more preferably ≥94%, more preferably ≥95%, more preferably ≥96%, more preferably ≥97%, more preferably ≥98%, more preferably ≥99%, more preferably ≥99.9% sequence identity to polypeptide sequence SEQ ID NO: 20.

The polypeptide sequence of a variant of the polypeptide sequence SEQ ID NO: 20 is not identical to SEQ ID NO: 20.

According to the invention, a hydantoin racemase $E_{320V}$ has hydantoin racemase activity, determined as described under item 4.5.14.4 and 4.5.14.5.

According to the invention, a hydantoin racemase $E_{320V}$ preferably has hydantoin racemase activity of at least 1%, preferably of at least 10%, more preferably of at least 20%, more preferably of at least 30%, more preferably of at least 40%, more preferably of at least 50%, more preferably of at least 60%, more preferably of at least 70%, more preferably of at least 80%, more preferably of at least 90%, more preferably of at least 99%, more preferably of at least 100% the hydantoin racemase of the hydantoin racemase $E_{320S}$, wherein the hydantoin racemase activity of $E_{320V}$, relative to the hydantoin racemase activity $E_{320S}$ is determined by Assay J described under item 4.5.14.6.

It is even more preferably according to the invention, that a hydantoin racemase $E_{320V}$ has hydantoin racemase activity in the range of 1 to 1000%, preferably in the range of 5 to 500%, more preferably in the range of 10 to 400%, more preferably in the range of 40 to 200%, more preferably in the range of 50 to 150%, more preferably in the range of 60 to 140%, more preferably in the range of 70 to 130%, more preferably in the range of 80 to 120%, more preferably in the range of 90 to 110%, more preferably 100% the hydantoin racemase activity of the hydantoin racemase $E_{320S}$, wherein the hydantoin racemase activity of $E_{320V}$, relative to the hydantoin racemase activity of $E_{320S}$ is determined by Assay J described under item 4.5.14.6.

4.5.14.7.5 Preferred Variants of SEQ ID NO: 21

According to the invention, the polypeptide sequence of the hydantoin racemase $E_3$ may also be a variant of SEQ ID NO: 21.

The hydantoin racemase $E_3$, the polypeptide sequence of which is SEQ ID NO: 21, is denoted as "$E_{321S}$". Hydantoin racemases $E_3$, the polypeptide sequence of which is selected from variants of SEQ ID NO: 21, are generally denoted as "$E_{321V}$".

A variant of the polypeptide sequence of SEQ ID NO: 21 is a polypeptide with sequence identity of at least 60%, preferably ≥65%, more preferably ≥70%, more preferably ≥75%, more preferably ≥80%, more preferably ≥85%, more preferably ≥90%, more preferably ≥91%, more preferably ≥92%, more preferably ≥93%, more preferably ≥94%, more preferably ≥95%, more preferably ≥96%, more preferably ≥97%, more preferably ≥98%, more preferably ≥99%, more preferably ≥99.9% sequence identity to polypeptide sequence SEQ ID NO: 21.

The polypeptide sequence of a variant of the polypeptide sequence SEQ ID NO: 21 is not identical to SEQ ID NO: 21.

According to the invention, a hydantoin racemase $E_{321V}$ has hydantoin racemase activity, determined as described under item 4.5.14.4 and 4.5.14.5.

According to the invention, a hydantoin racemase $E_{321V}$ preferably has hydantoin racemase activity of at least 1%, preferably of at least 10%, more preferably of at least 20%, more preferably of at least 30%, more preferably of at least 40%, more preferably of at least 50%, more preferably of at least 60%, more preferably of at least 70%, more preferably of at least 80%, more preferably of at least 90%, more preferably of at least 99%, more preferably of at least 100% the hydantoin racemase of the hydantoin racemase $E_{321S}$, wherein the hydantoin racemase activity of $E_{321V}$, relative to the hydantoin racemase activity $E_{321S}$ is determined by Assay J described under item 4.5.14.6.

It is even more preferably according to the invention, that a hydantoin racemase $E_{321V}$ has hydantoin racemase activity in the range of 1 to 1000%, preferably in the range of 5 to 500%, more preferably in the range of 10 to 400%, more preferably in the range of 40 to 200%, more preferably in the range of 50 to 150%, more preferably in the range of 60 to 140%, more preferably in the range of 70 to 130%, more preferably in the range of 80 to 120%, more preferably in the range of 90 to 110%, more preferably 100% the hydantoin racemase activity of the hydantoin racemase $E_{321S}$, wherein the hydantoin racemase activity of $E_{321V}$, relative to the hydantoin racemase activity of $E_{321S}$ is determined by Assay J described under item 4.5.14.6.

4.5.14.7.6 Preferred Variants of SEQ ID NO: 22

According to the invention, the polypeptide sequence of the hydantoin racemase $E_3$ may also be a variant of SEQ ID NO: 22.

The hydantoin racemase $E_3$, the polypeptide sequence of which is SEQ ID NO: 22, is denoted as "$E_{322S}$". Hydantoin racemases $E_3$, the polypeptide sequence of which is selected from variants of SEQ ID NO: 22, are generally denoted as "$E_{322V}$".

A variant of the polypeptide sequence of SEQ ID NO: 22 is a polypeptide with sequence identity of at least 60%, preferably ≥65%, more preferably ≥70%, more preferably ≥75%, more preferably ≥80%, more preferably ≥85%, more preferably ≥90%, more preferably ≥91%, more preferably ≥92%, more preferably ≥93%, more preferably ≥94%, more preferably ≥95%, more preferably ≥96%, more preferably ≥97%, more preferably ≥98%, more preferably ≥99%, more preferably ≥99.9% sequence identity to polypeptide sequence SEQ ID NO: 22.

The polypeptide sequence of a variant of the polypeptide sequence SEQ ID NO: 22 is not identical to SEQ ID NO: 22.

According to the invention, a hydantoin racemase $E_{322V}$ has hydantoin racemase activity, determined as described under item 4.5.14.4 and 4.5.14.5.

According to the invention, a hydantoin racemase $E_{322V}$ preferably has hydantoin racemase activity of at least 1%, preferably of at least 10%, more preferably of at least 20%, more preferably of at least 30%, more preferably of at least 40%, more preferably of at least 50%, more preferably of at least 60%, more preferably of at least 70%, more preferably of at least 80%, more preferably of at least 90%, more preferably of at least 99%, more preferably of at least 100% the hydantoin racemase of the hydantoin racemase $E_{322S}$, wherein the hydantoin racemase activity of $E_{322V}$, relative to the hydantoin racemase activity $E_{322S}$ is determined by Assay J described under item 4.5.14.6.

It is even more preferably according to the invention, that a hydantoin racemase $E_{322V}$ has hydantoin racemase activity in the range of 1 to 1000%, preferably in the range of 5 to 500%, more preferably in the range of 10 to 400%, more preferably in the range of 40 to 200%, more preferably in the range of 50 to 150%, more preferably in the range of 60 to 140%, more preferably in the range of 70 to 130%, more preferably in the range of 80 to 120%, more preferably in the range of 90 to 110%, more preferably 100% the hydantoin racemase activity of the hydantoin racemase $E_{322S}$, wherein the hydantoin racemase activity of $E_{322V}$, relative to the hydantoin racemase activity of $E_{322S}$ is determined by Assay J described under item 4.5.14.6.

4.5.14.7.7 Preferred Variants of SEQ ID NO: 23

According to the invention, the polypeptide sequence of the hydantoin racemase $E_3$ may also be a variant of SEQ ID NO: 23.

The hydantoin racemase $E_3$, the polypeptide sequence of which is SEQ ID NO: 23, is denoted as "$E_{323S}$". Hydantoin racemases $E_3$, the polypeptide sequence of which is selected from variants of SEQ ID NO: 23, are generally denoted as "$E_{323V}$".

A variant of the polypeptide sequence of SEQ ID NO: 23 is a polypeptide with sequence identity of at least 60%, preferably ≥65%, more preferably ≥70%, more preferably ≥75%, more preferably ≥80%, more preferably ≥85%, more preferably ≥90%, more preferably ≥91%, more preferably ≥92%, more preferably ≥93%, more preferably ≥94%, more preferably ≥95%, more preferably ≥96%, more preferably ≥97%, more preferably ≥98%, more preferably ≥99%, more preferably ≥99.9% sequence identity to polypeptide sequence SEQ ID NO: 23.

The polypeptide sequence of a variant of the polypeptide sequence SEQ ID NO: 23 is not identical to SEQ ID NO: 23.

According to the invention, a hydantoin racemase $E_{323V}$ has hydantoin racemase activity, determined as described under item 4.5.14.4 and 4.5.14.5.

According to the invention, a hydantoin racemase $E_{323V}$ preferably has hydantoin racemase activity of at least 1%, preferably of at least 10%, more preferably of at least 20%, more preferably of at least 30%, more preferably of at least 40%, more preferably of at least 50%, more preferably of at least 60%, more preferably of at least 70%, more preferably of at least 80%, more preferably of at least 90%, more preferably of at least 99%, more preferably of at least 100% the hydantoin racemase of the hydantoin racemase $E_{323S}$, wherein the hydantoin racemase activity of $E_{323V}$, relative to the hydantoin racemase activity $E_{323S}$ is determined by Assay J described under item 4.5.14.6.

It is even more preferably according to the invention, that a hydantoin racemase $E_{323V}$ has hydantoin racemase activity in the range of 1 to 1000%, preferably in the range of 5 to 500%, more preferably in the range of 10 to 400%, more preferably in the range of 40 to 200%, more preferably in the range of 50 to 150%, more preferably in the range of 60 to 140%, more preferably in the range of 70 to 130%, more preferably in the range of 80 to 120%, more preferably in the range of 90 to 110%, more preferably 100% the hydantoin racemase activity of the hydantoin racemase $E_{323S}$, wherein the hydantoin racemase activity of $E_{323V}$, relative to the hydantoin racemase activity of $E_{323S}$ is determined by Assay J described under item 4.5.14.6.

4.5.14.7.8 Preferred Variants of SEQ ID NO: 24

According to the invention, the polypeptide sequence of the hydantoin racemase $E_3$ may also be a variant of SEQ ID NO: 24.

The hydantoin racemase $E_3$, the polypeptide sequence of which is SEQ ID NO: 24, is denoted as "$E_{324S}$". Hydantoin racemases $E_3$, the polypeptide sequence of which is selected from variants of SEQ ID NO: 24, are generally denoted as "$E_{324V}$".

A variant of the polypeptide sequence of SEQ ID NO: 24 is a polypeptide with sequence identity of at least 60%, preferably ≥65%, more preferably ≥70%, more preferably ≥75%, more preferably ≥80%, more preferably ≥85%, more preferably ≥90%, more preferably ≥91%, more preferably ≥92%, more preferably ≥93%, more preferably ≥94%, more preferably ≥95%, more preferably ≥96%, more preferably ≥97%, more preferably ≥98%, more preferably ≥99%, more preferably ≥99.9% sequence identity to polypeptide sequence SEQ ID NO: 24.

The polypeptide sequence of a variant of the polypeptide sequence SEQ ID NO: 24 is not identical to SEQ ID NO: 24.

According to the invention, a hydantoin racemase $E_{324V}$ has hydantoin racemase activity, determined as described under item 4.5.14.4 and 4.5.14.5.

According to the invention, a hydantoin racemase $E_{324V}$ preferably has hydantoin racemase activity of at least 1%, preferably of at least 10%, more preferably of at least 20%, more preferably of at least 30%, more preferably of at least 40%, more preferably of at least 50%, more preferably of at least 60%, more preferably of at least 70%, more preferably of at least 80%, more preferably of at least 90%, more preferably of at least 99%, more preferably of at least 100% the hydantoin racemase of the hydantoin racemase $E_{324S}$, wherein the hydantoin racemase activity of $E_{324V}$, relative to the hydantoin racemase activity $E_{324S}$ is determined by Assay J described under item 4.5.14.6.

It is even more preferably according to the invention, that a hydantoin racemase $E_{324V}$ has hydantoin racemase activity in the range of 1 to 1000%, preferably in the range of 5 to 500%, more preferably in the range of 10 to 400%, more preferably in the range of 40 to 200%, more preferably in the range of 50 to 150%, more preferably in the range of 60 to 140%, more preferably in the range of 70 to 130%, more preferably in the range of 80 to 120%, more preferably in the range of 90 to 110%, more preferably 100% the hydantoin racemase activity of the hydantoin racemase $E_{324S}$, wherein the hydantoin racemase activity of $E_{324V}$, relative to the hydantoin racemase activity of $E_{324S}$ is determined by Assay J described under item 4.5.14.6.

4.5.14.7.9 Preferred Variants of SEQ ID NO: 25

According to the invention, the polypeptide sequence of the hydantoin racemase $E_3$ may also be a variant of SEQ ID NO: 25.

The hydantoin racemase $E_3$, the polypeptide sequence of which is SEQ ID NO: 25, is denoted as "$E_{325S}$". Hydantoin racemases $E_3$, the polypeptide sequence of which is selected from variants of SEQ ID NO: 25, are generally denoted as "$E_{325V}$".

A variant of the polypeptide sequence of SEQ ID NO: 25 is a polypeptide with sequence identity of at least 60%, preferably ≥65%, more preferably ≥70%, more preferably ≥75%, more preferably ≥80%, more preferably ≥85%, more preferably ≥90%, more preferably ≥91%, more preferably ≥92%, more preferably ≥93%, more preferably ≥94%, more preferably ≥95%, more preferably ≥96%, more preferably ≥97%, more preferably ≥98%, more preferably ≥99%, more preferably ≥99.9% sequence identity to polypeptide sequence SEQ ID NO: 25.

The polypeptide sequence of a variant of the polypeptide sequence SEQ ID NO: 25 is not identical to SEQ ID NO: 25.

According to the invention, a hydantoin racemase $E_{325V}$ has hydantoin racemase activity, determined as described under item 4.5.14.4 and 4.5.14.5.

According to the invention, a hydantoin racemase $E_{325V}$ preferably has hydantoin racemase activity of at least 1%, preferably of at least 10%, more preferably of at least 20%, more preferably of at least 30%, more preferably of at least 40%, more preferably of at least 50%, more preferably of at least 60%, more preferably of at least 70%, more preferably of at least 80%, more preferably of at least 90%, more preferably of at least 99%, more preferably of at least 100% the hydantoin racemase of the hydantoin racemase $E_{325S}$, wherein the hydantoin racemase activity of $E_{325V}$, relative to the hydantoin racemase activity $E_{325S}$ is determined by Assay J described under item 4.5.14.6.

It is even more preferably according to the invention, that a hydantoin racemase $E_{325V}$ has hydantoin racemase activity in the range of 1 to 1000%, preferably in the range of 5 to 500%, more preferably in the range of 10 to 400%, more preferably in the range of 40 to 200%, more preferably in the range of 50 to 150%, more preferably in the range of 60 to 140%, more preferably in the range of 70 to 130%, more preferably in the range of 80 to 120%, more preferably in the range of 90 to 110%, more preferably 100% the hydantoin racemase activity of the hydantoin racemase $E_{325S}$, wherein the hydantoin racemase activity of $E_{325V}$, relative to the hydantoin racemase activity of $E_{325S}$ is determined by Assay J described under item 4.5.14.6.

4.5.14.7.10 Preferred Variants of SEQ ID NO: 26

According to the invention, the polypeptide sequence of the hydantoin racemase $E_3$ may also be a variant of SEQ ID NO: 26.

The hydantoin racemase $E_3$, the polypeptide sequence of which is SEQ ID NO: 26, is denoted as "$E_{326S}$". Hydantoin racemases $E_3$, the polypeptide sequence of which is selected from variants of SEQ ID NO: 26, are generally denoted as "$E_{326V}$".

A variant of the polypeptide sequence of SEQ ID NO: 26 is a polypeptide with sequence identity of at least 60%, preferably ≥65%, more preferably ≥70%, more preferably ≥75%, more preferably ≥80%, more preferably ≥85%, more preferably ≥90%, more preferably ≥91%, more preferably ≥92%, more preferably ≥93%, more preferably ≥94%, more preferably ≥95%, more preferably ≥96%, more preferably ≥97%, more preferably ≥98%, more preferably ≥99%, more preferably ≥99.9% sequence identity to polypeptide sequence SEQ ID NO: 26.

The polypeptide sequence of a variant of the polypeptide sequence SEQ ID NO: 26 is not identical to SEQ ID NO: 26.

According to the invention, a hydantoin racemase $E_{326V}$ has hydantoin racemase activity, determined as described under item 4.5.14.4 and 4.5.14.5.

According to the invention, a hydantoin racemase $E_{326V}$ preferably has hydantoin racemase activity of at least 1%, preferably of at least 10%, more preferably of at least 20%, more preferably of at least 30%, more preferably of at least 40%, more preferably of at least 50%, more preferably of at least 60%, more preferably of at least 70%, more preferably of at least 80%, more preferably of at least 90%, more preferably of at least 99%, more preferably of at least 100% the hydantoin racemase of the hydantoin racemase $E_{326S}$, wherein the hydantoin racemase activity of $E_{326V}$, relative to the hydantoin racemase activity $E_{326S}$ is determined by Assay J described under item 4.5.14.6.

It is even more preferably according to the invention, that a hydantoin racemase $E_{326V}$ has hydantoin racemase activity in the range of 1 to 1000%, preferably in the range of 5 to 500%, more preferably in the range of 10 to 400%, more preferably in the range of 40 to 200%, more preferably in the range of 50 to 150%, more preferably in the range of 60 to 140%, more preferably in the range of 70 to 130%, more preferably in the range of 80 to 120%, more preferably in the range of 90 to 110%, more preferably 100% the hydantoin racemase activity of the hydantoin racemase $E_{326S}$, wherein the hydantoin racemase activity of $E_{326V}$, relative to the hydantoin racemase activity of $E_{326S}$ is determined by Assay J described under item 4.5.14.6.

4.5.15 Preferred Method Conditions in Step (a)

In this preferred embodiment, in which step (a) is catalyzed by a hydantoin racemase $E_3$, the reaction in step (a) may be carried out under conditions known to the skilled person.

The reaction medium is preferably aqueous, more preferably an aqueous buffer.

Exemplary buffers commonly used in biotransformation reactions and advantageously used herein include Tris, phosphate, or any of Good's buffers, such as 2-(N-morpholino)ethanesulfonic acid ("MES"), N-(2-acetamido)iminodiacetic acid ("ADA"), piperazine-N,N'-bis(2-ethanesulfonic acid) ("PIPES"), N-(2-acetamido)-2-aminoethanesulfonic acid ("ACES"), P-hydroxy-4-morpholinepropanesulfonic acid ("MOPSO"), cholamine chloride, 3-(N-morpholino)propanesulfonic acid ("MOPS"), N, N-Bis(2-hydroxyethyl)-2-aminoethanesulfonic acid ("BES"), 2-[[1,3-dihydroxy-2-(hydroxymethyl) propan-2-yl]amino]ethanesulfonic acid ("TES"), 4-(2-hydroxyethyl)-1-piperazineethanesulfonic acid ("HEPES"), 3-(Bis(2-hydroxyethyl)amino)-2-hydroxypropane-1-sulfonic acid ("DIPSO"), acetamidoglycine, 3-(N-Tris(hydroxymethyl)methylamino(-2-hydroxypropane) sulfonic acid ("TAPSO"), piperazine-N,N'-bis(2-hydroxypropanesulfonic acid) ("POPSO"), 4-(2-Hydroxyethyl) piperazine-1-(2-hydroxypropanesulfonic acid) ("HEPPSO"), 3-[4-(2-Hydroxyethyl)-1-piperazinyl]propanesulfonic acid ("HEPPS"), tricine, glycinamide, bicine, or 3-[[1,3-dihydroxy-2-(hydroxymethyl) propan-2-yl]amino]propane-1-sulfonic acid ("TAPS").

In some embodiments, ammonium can act as a buffer. One or more organic solvents can also be added to the reaction.

The buffer preferably contains metal salts, more preferably metal salts such as halogenides of monovalent or bivalent metals (e.g. $CoCl_2$, $MnCl_2$).

The concentration of these metal salts in the reaction medium is preferably in the range from 1 μM to 1 M, more preferably 1 mM to 100 mM, even more preferably 1 to 10 mM.

Preferably, step (a) of the method according to the first aspect of the invention is carried out in a phosphate buffer.

The pH of the reaction medium in step (a) of the method according to the first aspect of the invention is preferably in the range of from 2 to 10, more preferably in the range of from 5 to 8, more preferably 7.2 to 7.5, most preferably 7.5.

Preferably, step (a) of the method according to the first aspect of the invention is carried out at a temperature in the range of from 20° C. to 70° C., more preferably in the range of from 30° C. to 55° C., most preferably 50° C.

In this preferred embodiment, in which step (a) is catalyzed by a hydantoin racemase $E_3$, the preferred reaction conditions in step (a) are the same as described for steps (b) and (c), confer items 4.5.7 and 4.5.13, respectively. It is even more preferred to carry out step (a) concomitantly with steps (b) and (c).

Preferably, the total concentration of all hydantoin racemases $E_3$ in the reaction solution in step (a) is in the range of from 1 μM to 10 mM, preferably 10 μM to 1 mM, more preferably 0.1 mM to 0.5 mM, most preferably 0.4 mM.

In alternative preferred embodiments, the total concentration of all hydantoin racemases $E_3$ in the reaction solution in step (a) is in the range of from 1 μg/l to 10 g/l, preferably 0.1 mg/l to 5 g/l, more preferably 1 mg/l to 1 g/l, more preferably 5 mg/l to 500 mg/l.

Preferably, step (a) is carried out in the same reaction medium in which steps (c) and (b) are carried out. The advantage is that this allows for a one-pot synthesis in which all the steps (a), (b), and (c) are carried out.

Preferably, the initial concentration of all the compounds according to formula D-(III) in the reaction medium in step (a) is in the range of from 1 μM to 1 M, preferably of from 10 μM to 0.5 M, more preferably of from 0.1 mM to 0.1 M, more preferably of from 1 mM to 10 mM, most preferably 1.25 mM.

If compounds according to formula L-(III) are present in the reaction medium in step (a), the initial concentration of all the compounds according to formula L-(III) in the reaction medium is preferably from 1 to 100 times the concentration of all the compounds according to formula D-(III), more preferably 1 to 10 times the concentration, even more preferably 1 to 2 times even more preferably the same as the concentration of all the compounds according to formula D-(III).

"Initial concentration of all the compounds according to formula L-(III)/D-(III)" refers to the concentration of the respective compound L-(III) or D-(III), respectively, in the reaction medium when the respective compounds are employed in step (a).

4.6 Second Aspect: Method for Production of an L-Glufosinate P-Ester

In a second aspect, the present invention relates to a further method for the production of an L-glufosinate P-ester according to formula L-(I):

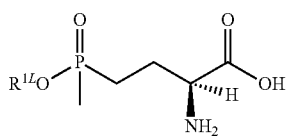

L-(I)

from a mixture $M_{IIIA}$ comprising at least one compound L-(III) and at least one compound D-(III):

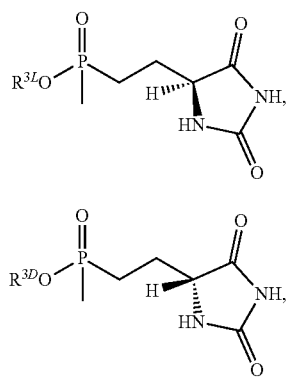

wherein $R^{1L}$ is a radical selected from the above-mentioned formulae (VIII), (IX), (X), preferably selected from the above-mentioned formulae (IX), (X), more preferably $R^{1L}$ has formula (X).

When $R^{1L}$ is a radical of the formula (VIII), the radical $R^{1L}$ may be selected from the above-mentioned formulae L-(VIII) and D-(VIII), preferably L-(VIII).

When $R^{1L}$ is a radical of the formula (IX), the radical $R^{1L}$ may be selected from the above-mentioned formulae L-(IX) and D-(IX), preferably L-(IX).

When $R^{1L}$ is a radical of the formula (X), the radical $R^{1L}$ may be selected from the above-mentioned formulae L-(X) and D-(X), preferably L-(X).

$R^{3L}$ is a radical selected from the above-mentioned formulae (VIII), (IX), (X), preferably selected from the formulae (VIII), (IX), more preferably $R^{3L}$ has formula (VIII).

When $R^{3L}$ is a radical of the formula (VIII), the radical $R^{3L}$ may be selected from the above-mentioned formulae L-(VIII) and D-(VIII), preferably L-(VIII).

When $R^{3L}$ is a radical of the formula (IX), the radical $R^{3L}$ may be selected from the above-mentioned formulae L-(IX) and D-(IX), preferably L-(IX).

When $R^{3L}$ is a radical of the formula (X), the radical $R^{3L}$ may be selected from the above-mentioned formulae L-(X) and D-(X), preferably L-(X).

$R^{3D}$ is a radical selected from the above-mentioned formulae (VIII), (IX), (X), preferably selected from the formulae (VIII), (IX), more preferably $R^{3D}$ has formula (VIII).

When $R^{3D}$ is a radical of the formula (VIII), the radical $R^{3D}$ may be selected from the above-mentioned formulae L-(VIII) and D-(VIII), preferably L-(VIII).

When $R^{3D}$ is a radical of the formula (IX), the radical $R^{3D}$ may be selected from the above-mentioned formulae L-(IX) and D-(IX), preferably L-(IX).

When $R^{3D}$ is a radical of the formula (X), the radical $R^{3D}$ may be selected from the above-mentioned formulae L-(X) and D-(X), preferably L-(X).

In this method according to the second aspect of the invention, a mixture $M_{IIIA}$ comprising at least one compound L-(III) and at least one compound D-(III), wherein preferably $R^{3L}=R^{3D}$, is provided, and subjected to at least two enzymatic reactions (ii) and (iii), giving a composition $M_I$ comprising at least one compound L-(I) and optionally D-(I). Therefore, the reaction according to the preferred second aspect of the invention is enzymatic.

The method for the production of an L-glufosinate P-ester according to formula L-(I), according to the second aspect of the invention is L-enantioselective, in particular L-enantiospecific, because $M_I$ either comprises compounds according to formula L-(I), but not compounds according to formula D-(I) (in which case it is "L-enantiospecific") or, when $M_I$ comprises compounds according to formulae L-(I) and D-(I), the molar ratio of all compounds according to formula L-(I) in $M_I$ to all compounds according to formula D-(I) in $M_I$ is greater than the molar ratio of all compounds according to formula L-(III) in $M_{IIIA}$ to all compounds of formula D-(III) in $M_{IIIA}$ (in which case it is "L-enantioselective, but not L-enantiospecific").

In a particular embodiment of the method according to the second aspect of the invention, $M_I$ comprises at least one compound according to formula L-(I) and at least one compound according to formula D-(I) and the molar ratio of all compounds according to formula L-(I) in $M_I$ to all compounds according to formula D-(I) in $M_I$ is greater than the molar ratio of all compounds according to formula L-(III) in $M_{IIIA}$ to all compounds of formula D-(III) in $M_{IIIA}$ (in which case the method according to the second aspect of the invention is "L-enantioselective, but not L-enantiospecific").

In a preferred embodiment of the method according to the second aspect of the invention, a mixture $M_{IIIA}$ comprising at least one compound L-(III) and at least one compound D-(III), wherein $R^{3L}=R^{3D}$, is provided in step (a).

In the method according to the second aspect of the invention, it is possible to enrich the amount of compounds according to formula L-(I) over compounds according to formula D-(I) in the product composition $M_I$, which means that the molar ratio of all compounds according to formula L-(I) in $M_I$ to all compounds according to formula D-(I) in $M_I$ is greater than the molar ratio of all compounds according to formula L-(III) in $M_{IIIA}$ to all compounds of formula D-(III) in $M_{IIIA}$ provided in step (i-A).

In particular, the molar amount of compounds of formula L-(I) per compound of formula D-(I) in $M_I$ is greater than the molar amount of compounds of formula L-(III) per compound of formula D-(III) in $M_{IIIA}$, in particular by a factor of XL, wherein XL is at least 1.1, preferably at least 1.5, more preferably at least 2, more preferably at least 5, even more preferably at least 9, even more preferably at least 99. In another preferred embodiment XL is in the range of 1.1 to 99, preferably in the range of 1.5 to 9, even more preferably in the range of 2 to 5.

4.6.1 Step (i-A)

In a first step of the method according to the second aspect of the invention, a mixture $M_{IIIA}$ comprising at least one compound L-(III) and at least one compound D-(III) is provided.

In a preferred embodiment, the molar ratio of all compounds according to formula L-(III) in the mixture $M_{IIIA}$ to all compounds according to formula D-(III) in the mixture Mil is essentially 1:1.

Alternatively, compounds according to formula D-(III) are comprised in an excess to compounds according to formula L-(III) in mixture $M_{IIIA}$, meaning that, while L-(III) is present in mixture $M_{IIIA}$, the molar ratio of all compounds according to formula L-(III) to all compounds according to formula D-(III) in mixture $M_{IIIA}$ is <1:1, preferably <0.9:1, more preferably <0.75:1, more preferably <0.5:1, more preferably <0.2:1, more preferably <0.1:1, more preferably <0.01:1.

In other preferred embodiments, the molar ratio of all compounds according to formula L-(III) in the mixture $M_{IIIA}$ to all compounds according to formula D-(III) in the mixture $M_{IIIA}$ is in the range of from 3:2 to 1:99, more preferably in the range of from 1.01:1 to 1:99, more preferably in the range of from 1:1 to 1:99, more preferably in the range of from 1:1.01 to 1:99, more preferably in the range of from 1:1.01 to 1:9, more preferably in the range of from 1:1.01 to 1:8, more preferably in the range of from 1:1.01 to 1:3.

Alternatively, D-(III) is comprised in an excess to L-(III) in mixture $M_{IIIA}$, meaning that, while at least one compound according to formula L-(III) is in the mixture $M_{IIIA}$, the molar ratio of all compounds according to formula L-(III) is in the mixture $M_{IIIA}$ to all compounds according to formula D-(III) in the mixture $M_{IIIA}$ is <1:1, preferably <0.9:1, more preferably <0.75:1, more preferably <0.5:1, more preferably <0.2:1, more preferably <0.1:1, more preferably <0.01:1.

A mixture of these compounds can be obtained by the skilled person, for example by organic synthesis as set forth in DE 31 42 036 A1 and by Slomka et al.

E. Ware, Chem. Rev. 1950, 46, 403-470 and C. Avendaño & J. C. Menendez, "Hydantoin and its derivates" in Kirk-Othmer Encyclopedia of Chemical Technology 2000 give a general overview over hydantoin chemistry.

Preferably, the mixture $M_{IIIA}$ is provided in step (i-A) in a reaction medium.

Namely, the reaction medium in step (i-A) is preferably aqueous, more preferably an aqueous buffer.

Exemplary buffers commonly used in biotransformation reactions and advantageously used in step (i-A) include Tris, phosphate, or any of Good's buffers, such as 2-(N-morpholino) ethanesulfonic acid ("MES"), N-(2-acetamido)iminodiacetic acid ("ADA"), piperazine-N,N'-bis(2-ethanesulfonic acid) ("PIPES"), N-(2-acetamido)-2-aminoethanesulfonic acid ("ACES"), P-hydroxy-4-morpholinepropanesulfonic acid ("MOPSO"), cholamine chloride, 3-(N-morpholino) propanesulfonic acid ("MOPS"), N,N-Bis(2-hydroxyethyl)-2-aminoethanesulfonic acid ("BES"), 2-[[1,3-dihydroxy-2-(hydroxymethyl) propan-2-yl]amino]ethanesulfonic acid ("TES"), 4-(2-hydroxyethyl)-1-piperazineethanesulfonic acid ("HEPES"), 3-(Bis(2-hydroxyethyl)amino)-2-hydroxypropane-1-sulfonic acid ("DIPSO"), acetamidoglycine, 3-(N-Tris(hydroxymethyl)methylamino(-2-hydroxypropane) sulfonic acid ("TAPSO"), piperazine-N,N'-bis(2-hydroxypropanesulfonic acid) ("POPSO"), 4-(2-Hydroxyethyl) piperazine-1-(2-hydroxypropanesulfonic acid) ("HEPPSO"), 3-[4-(2-Hydroxyethyl)-1-piperazinyl]propanesulfonic acid ("HEPPS"), tricine, glycinamide, bicine, or 3-[[1,3-dihydroxy-2-(hydroxymethyl) propan-2-yl]amino]propane-1-sulfonic acid ("TAPS").

In some embodiments, ammonium can act as a buffer. One or more organic solvents can also be added to the reaction.

The buffer preferably contains metal salts, more preferably metal salts such as halogenides of monovalent or bivalent metals (e.g. $CoCl_2$, $MnCl_2$).

The concentration of these metal salts in the reaction medium in step (i-A) is preferably in the range from 1 µM to 1 M, more preferably 1 mM to 100 mM, even more preferably 1 to 10 mM.

Preferably, step (i-A) of the method according to the second aspect of the invention is carried out in a phosphate buffer.

The pH of the reaction medium in step (i-A) of the method according to the first aspect of the invention is preferably in the range of from 2 to 10, more preferably in the range of from 5 to 8, more preferably 7.2 to 7.5, most preferably 7.5.

More preferably, the concentration of all the compounds according to formula D-(III) in the reaction medium provided in step (i-A) is in the range of from 1 µM to 1 M, preferably of from 10 µM to 0.5 M, more preferably of from 0.1 mM to 0.1 M, more preferably of from 1 mM to 10 mM, most preferably 1.25 mM.

Concerning the compounds according to formula L-(III) that are present in the reaction medium preferably provided in step (i-A), the concentration of all the compounds according to formula L-(III) in the reaction medium is preferably from 1 to a 100 times the concentration of all the compounds according to formula D-(III), more preferably 1 to 10 times the concentration, even more preferably 1 to 2 times even more preferably the same as the concentration of all the compounds according to formula D-(III).

4.6.2 Optional Step (i-B)

In an optional step (i-B), at least a part of the compounds D-(III) comprised by the mixture $M_{IIIA}$ are reacted into compounds according to the formula L-(III), giving a composition $M_{IIIB}$ comprising compounds according to formula L-(III) and optionally compounds according to formula D-(III). It goes without saying that the molar ratio of all compounds according to formula L-(III) to all compounds in formula D-(III) in mixture $M_{IIIB}$ is greater than the molar ratio of all compounds according to formula L-(III) to all compounds in formula D-(III) in mixture $M_{IIIA}$.

In case step (i-B) is carried out, it is preferably carried out as described for step (a) under items 4.5.14 and 4.5.15.

In particular, the reaction according to step (i-B) is catalyzed by a hydantoin racemase $E_3$ as described with respect to step (a).

Preferably, the hydantoin racemase $E_3$ used in step (i-B) is categorized in the EC class 5.1.99.5.

In another embodiment, the polypeptide sequence of the hydantoin racemase $E_3$ used in step (i-B) is selected from the group consisting of SEQ ID NO: 17 and variants thereof, SEQ ID NO: 18 and variants thereof, SEQ ID NO: 19 and variants thereof, SEQ ID NO: 20 and variants thereof, SEQ ID NO: 21 and variants thereof, SEQ ID NO: 22 and variants thereof, SEQ ID NO: 23 and variants thereof, SEQ ID NO: 24 and variants thereof, SEQ ID NO: 25 and variants thereof, SEQ ID NO: 26 and variants thereof, most preferably selected from SEQ ID NO: 17 and variants thereof.

Preferably, the hydantoin racemase $E_3$ used in step (i-B) is selected from the group consisting of $E_{317S}$ and $E_{317V}$ (both described under item 4.5.14.7.1), $E_{318S}$ and $E_{318V}$ (both described under item 4.5.14.7.2), $E_{319S}$ and $E_{319V}$ (both described under item 4.5.14.7.3), $E_{320S}$ and $E_{320V}$ (both described under item 4.5.14.7.4), $E_{321S}$ and $E_{321V}$ (both described under item 4.5.14.7.5), $E_{322S}$ and $E_{322V}$ (both described under item 4.5.14.7.6), $E_{323S}$ and $E_{323V}$ (both described under item 4.5.14.7.7), $E_{324S}$ and $E_{324V}$ (both described under item 4.5.14.7.8), $E_{325S}$ and $E_{325V}$ (both described under item 4.5.14.7.9), $E_{326S}$ and $E_{326V}$ (both described under item 4.5.14.7.10), more preferably from $E_{317S}$ and $E_{317V}$, even more preferably from $E_{317S}$.

The reaction conditions in step (i-B) are preferably as described with respect to step (a) under item 4.5.15.

Namely, the reaction medium in step (i-B) is preferably aqueous, more preferably an aqueous buffer.

Exemplary buffers commonly used in biotransformation reactions and advantageously used in step (i-B) include Tris, phosphate, or any of Good's buffers, such as 2-(N-morpholino) ethanesulfonic acid ("MES"), N-(2-acetamido)iminodiacetic acid ("ADA"), piperazine-N,N'-bis(2-ethanesulfonic acid) ("PIPES"), N-(2-acetamido)-2-aminoethanesulfonic acid ("ACES"), P-hydroxy-4-morpholinepropanesulfonic acid ("MOPSO"), cholamine chloride, 3-(N-morpholino) propanesulfonic acid ("MOPS"), N,N-Bis(2-hydroxyethyl)-2-aminoethanesulfonic acid ("BES"), 2-[[1,3-dihydroxy-2-(hydroxymethyl) propan-2-yl]amino]ethanesulfonic acid ("TES"), 4-(2-hydroxyethyl)-1-piperazineethanesulfonic acid ("HEPES"), 3-(Bis(2-hydroxyethyl)amino)-2-hydroxypropane-1-sulfonic acid ("DIPSO"), acetamidoglycine, 3-(N-Tris(hydroxymethyl)methylamino(-2-hydroxypropane) sulfonic acid ("TAPSO"), piperazine-N,N'-bis(2-hydroxypropanesulfonic acid) ("POPSO"), 4-(2-Hydroxyethyl) piperazine-1-(2-hydroxypropanesulfonic acid) ("HEPPSO"), 3-[4-(2-Hydroxyethyl)-1-piperazinyl]propanesulfonic acid ("HEPPS"), tricine, glycinamide, bicine, or 3-[[1,3-dihydroxy-2-(hydroxymethyl) propan-2-yl]amino]propane-1-sulfonic acid ("TAPS").

In some embodiments, ammonium can act as a buffer. One or more organic solvents can also be added to the reaction.

The buffer preferably contains metal salts, more preferably metal salts such as halogenides of monovalent or bivalent metals (e.g. $CoCl_2$, $MnCl_2$).

The concentration of these metal salts in the reaction medium in step (i-B) is preferably in the range from 1 μM to 1 M, more preferably 1 mM to 100 mM, even more preferably 1 to 10 mM.

Preferably, step (i-B) of the method according to the second aspect of the invention is carried out in a phosphate buffer.

The pH of the reaction medium in step (i-B) of the method according to the first aspect of the invention is preferably in the range of from 2 to 10, more preferably in the range of from 5 to 8, more preferably 7.2 to 7.5, most preferably 7.5.

Preferably, step (i-B) of the method according to the first aspect of the invention is carried out at a temperature in the range of from 20° C. to 70° C., more preferably in the range of from 30° C. to 55° C., most preferably 50° C.

Preferably, the total concentration of all hydantoin racemases $E_3$ in the reaction solution in step (i-B) is in the range of from 1 μM to 10 mM, preferably 10 μM to 1 mM, more preferably 0.1 mM to 0.5 mM, most preferably 0.4 mM.

In alternative preferred embodiments, the total concentration of all hydantoin racemases $E_3$ in the reaction solution in step (i-B) is in the range of from 1 μg/l to 10 g/l, preferably 0.1 mg/l to 5 g/l, more preferably 1 mg/l to 1 g/l, more preferably 5 mg/l to 500 mg/l.

Preferably, step (i-B) is carried out in the same reaction medium in which steps (ii) and (iii) are carried out. The advantage is that this allows for a one-pot synthesis in which all the steps (i-B), (ii), and (iii) are carried out.

At the end of optional step (i-B), a composition $M_{IIIB}$ comprising compounds according to formula L-(III) and optionally compounds according to formula D-(III) is obtained, preferably a composition $M_{IIIB}$ comprising compounds according to formula L-(III) and compounds according to formula D-(III) is obtained.

4.6.3 Step (ii)

In step (ii) of the method according to the second aspect of the invention, the mixture $M_{IIIA}$ or, in case step (i-B) is carried out, composition $M_{IIIB}$, is subjected to step (b) as described above under item 4.5.8-4.5.13.

In other words: in those embodiments, in which step (i-B) is not carried out, $M_{IIIA}$ is subjected to step (b) as described above under item 4.5.8-4.5.13.

In case step (i-B) is carried out, $M_{IIIB}$ obtained after step (i-B) is subjected to step (b) as described above under item 4.5.8-4.5.13.

The reaction according to step (ii) is catalyzed by a hydantoinase $E_2$ as described with respect to step (b), preferably by an L-hydantoinase $E_2$ as described with respect to step (b).

More preferably, the hydantoinase $E_2$, even more preferably the L-hydantoinase $E_2$ used in step (ii) is categorized in the EC class 3.5.2.2.

In another preferred embodiment, the polypeptide sequence of the hydantoinase $E_2$, even more preferably the L-hydantoinase $E_2$ used in step (ii) is selected from the group consisting of SEQ ID NO: 10 and variants thereof, SEQ ID NO: 11 and variants thereof, SEQ ID NO: 12 and variants thereof, SEQ ID NO: 13 and variants thereof, SEQ ID NO: 14 and variants thereof, SEQ ID NO: 15 and variants thereof, SEQ ID NO: 16 and variants thereof, even more preferably from SEQ ID NO: 10 and variants thereof.

Preferably, the hydantoinase $E_2$, even more preferably the L-hydantoinase $E_2$ used in step (ii) is selected from the group consisting of $E_{210S}$ and $E_{210V}$ (both described under item 4.5.12.1), $E_{211S}$ and $E_{211V}$ (both described under item 4.5.12.2), $E_{212S}$ and $E_{212V}$ (both described under item 4.5.12.3), $E_{213S}$ and $E_{213V}$ (both described under item 4.5.12.4), $E_{214S}$ and $E_{214V}$ (both described under item 4.5.12.5), $E_{215S}$ and $E_{215V}$ (both described under item 4.5.12.6), $E_{216S}$ and $E_{216V}$ (both described under item 4.5.12.7), more preferably from $E_{210S}$ and $E_{210V}$, even more preferably from $E_{210S}$.

The reaction conditions in step (ii) are preferably as described with respect to step (b) under item 4.5.13.

Namely, the reaction medium in step (ii) is preferably aqueous, more preferably an aqueous buffer.

Exemplary buffers commonly used in biotransformation reactions and advantageously used in step (ii) include Tris, phosphate, or any of Good's buffers, such as 2-(N-morpholino) ethanesulfonic acid ("MES"), N-(2-acetamido)iminodiacetic acid ("ADA"), piperazine-N,N'-bis(2-ethanesulfonic acid) ("PIPES"), N-(2-acetamido)-2-aminoethanesulfonic acid ("ACES"), P-hydroxy-4-morpholinepropanesulfonic acid ("MOPSO"), cholamine chloride, 3-(N-morpholino) propanesulfonic acid ("MOPS"), N,N-Bis(2-hydroxyethyl)-2-aminoethanesulfonic acid ("BES"), 2-[[1,3-dihydroxy-2-(hydroxymethyl) propan-2-yl]amino]ethanesulfonic acid ("TES"), 4-(2-hydroxyethyl)-1-piperazineethanesulfonic acid ("HEPES"), 3-(Bis(2-hydroxyethyl)amino)-2-hydroxypropane-1-sulfonic acid ("DIPSO"), acetamidoglycine, 3-(N-Tris(hydroxymethyl)methylamino(-2-hydroxypropane) sulfonic acid ("TAPSO"), piperazine-N, N-bis(2-hydroxypropane-sulfonic acid) ("POPSO"), 4-(2-Hydroxyethyl) piperazine-1-(2-hydroxypropanesulfonic acid) ("HEPPSO"), 3-[4-(2-Hydroxyethyl)-1-piperazinyl]propanesulfonic acid ("HEPPS"), tricine, glycinamide, bicine, or 3-[[1,3-dihydroxy-2-(hydroxymethyl) propan-2-yl]amino]propane-1-sulfonic acid ("TAPS").

In some embodiments, ammonium can act as a buffer. One or more organic solvents can also be added to the reaction.

The buffer preferably contains metal salts, more preferably metal salts such as halogenides of monovalent or bivalent metals (e.g. $CoCl_2$, $MnCl_2$).

The concentration of these metal salts in the reaction medium is preferably in the range from 1 µM to 1 M, more preferably 1 mM to 100 mM, even more preferably 1 to 10 mM.

Preferably, step (ii) of the method according to the second aspect of the invention is carried out in a phosphate buffer.

The pH of the reaction medium in step (ii) of the method according to the first aspect of the invention is preferably in the range of from 2 to 10, more preferably in the range of from 5 to 8, more preferably 7.2 to 7.5, most preferably 7.5.

Preferably, step (ii) of the method according to the first aspect of the invention is carried out at a temperature in the range of from 20° C. to 70° C., more preferably in the range of from 30° C. to 55° C., most preferably 50° C.

Preferably, the total concentration of all hydantoinases $E_2$ in the reaction solution in step (ii) is in the range of from 1 µM to 10 mM, preferably 10 µM to 1 mM, more preferably 0.1 mM to 0.5 mM, most preferably 0.4 mM.

In alternative preferred embodiments, the total concentration of all hydantoinases $E_2$ in the reaction solution in step (ii) is in the range of from 1 µg/l to 10 g/l, preferably 0.1 mg/l to 5 g/l, more preferably 1 mg/l to 1 g/l, more preferably 5 mg/l to 500 mg/l.

Preferably, step (ii) is carried out in the same reaction medium in which step (iii) is carried out.

At the end of step (ii), a composition $M_{II}$ comprising at least one compound according to formula L-(II) and optionally at least one compound according to formula D-(II), wherein L-(II) and D-(II) have the above-mentioned formulae, is obtained.

4.6.4 Step (iii)

In step (iii) of the method according to the second aspect of the invention, $M_{II}$ obtained in step (ii) is subjected to step (c) as described above under items 4.5.1 to 4.5.7 wherein the reaction according to step (iii) is catalyzed by an L-carbamoylase $E_1$.

This brings about that compounds according to formula L-(I) are enriched over compounds according to formulas D-(I) in $M_I$, i.e., compared to the molar ratio of compounds according to formula L-(I) to compounds according to formulas D-(I) in $M_{IIIA}$.

More preferably, the L-carbamoylase $E_1$ used in step (iii) is categorized in the EC class 3.5.1.87. In another preferred embodiment, the polypeptide sequence of the L-carbamoylase $E_1$ used in step (iii) is selected from the group consisting of SEQ ID NO: 1 and variants thereof, SEQ ID NO: 2 and variants thereof, SEQ ID NO: 3 and variants thereof, SEQ ID NO: 4 and variants thereof, SEQ ID NO: 5 and variants thereof, SEQ ID NO: 6 and variants thereof, SEQ ID NO: 7 and variants thereof, SEQ ID NO: 8 and variants thereof, SEQ ID NO: 9 and variants thereof.

Preferably, the L-carbamoylase $E_1$ used in step (iii) is selected from the group consisting of $E_{101S}$ and $E_{101V}$ (both described under item 4.5.6.1), $E_{102S}$ and $E_{102V}$ (both described under item 4.5.6.2), $E_{103S}$ and $E_{103V}$ (both described under item 4.5.6.3), $E_{104S}$ and $E_{104V}$ (both described under item 4.5.6.4), $E_{105S}$ and $E_{105V}$ (both described under item 4.5.6.5), $E_{106S}$ and $E_{106V}$ (both described under item 4.5.6.6), $E_{107S}$ and $E_{107V}$ (both described under item 4.5.6.7), $E_{108S}$ and $E_{108V}$ (both described under item 4.5.6.8), $E_{109S}$ and $E_{109V}$ (both described under item 4.5.6.9), more preferably from $E_{101S}$ and $E_{101V}$, even more preferably from $E_{101S}$.

The reaction conditions in step (iii) are preferably as described with respect to step (c) under item 4.5.7.

Namely, the reaction medium in step (iii) is preferably aqueous, more preferably an aqueous buffer.

Exemplary buffers commonly used in biotransformation reactions and advantageously used in step (iii) include Tris, phosphate, or any of Good's buffers, such as 2-(N-morpholino) ethanesulfonic acid ("MES"), N-(2-acetamido)iminodiacetic acid ("ADA"), piperazine-N,N'-bis(2-ethanesulfonic acid) ("PIPES"), N-(2-acetamido)-2-aminoethanesulfonic acid ("ACES"), P-hydroxy-4-morpholinepropanesulfonic acid ("MOPSO"), cholamine chloride, 3-(N-morpholino) propanesulfonic acid ("MOPS"), N,N-Bis(2-hydroxyethyl)-2-aminoethanesulfonic acid ("BES"), 2-[[1,3-dihydroxy-2-(hydroxymethyl) propan-2-yl]amino]ethanesulfonic acid ("TES"), 4-(2-hydroxyethyl)-1-piperazineethanesulfonic acid ("HEPES"), 3-(Bis(2-hydroxyethyl)amino)-2-hydroxypropane-1-sulfonic acid ("DIPSO"), acetamidoglycine, 3-(N-Tris(hydroxymethyl)methylamino(-2-hydroxypropane) sulfonic acid ("TAPSO"), piperazine-N,N'-bis(2-hydroxypropane-sulfonic acid) ("POPSO"), 4-(2-Hydroxyethyl) piperazine-1-(2-hydroxypropanesulfonic acid) ("HEPPSO"), 3-[4-(2-Hydroxyethyl)-1-piperazinyl]propanesulfonic acid ("HEPPS"), tricine, glycinamide, bicine, or 3-[[1,3-dihydroxy-2-(hydroxymethyl) propan-2-yl]amino]propane-1-sulfonic acid ("TAPS").

In some embodiments, ammonium can act as a buffer. One or more organic solvents can also be added to the reaction.

The buffer preferably contains metal salts, more preferably metal salts such as halogenides of monovalent or bivalent metals (e.g. $CoCl_2$, $MnCl_2$).

The concentration of these metal salts in the reaction medium is preferably in the range from 1 µM to 1 M, more preferably 1 mM to 100 mM, even more preferably 1 to 10 mM.

Preferably, step (iii) of the method according to the second aspect of the invention is carried out in a phosphate buffer.

The pH of the reaction medium in step (iii) of the method according to the first aspect of the invention is preferably in the range of from 2 to 10, more preferably in the range of from 5 to 8, more preferably 7.2 to 7.5, most preferably 7.5.

Preferably, step (iii) of the method according to the first aspect of the invention is carried out at a temperature in the range of from 20° C. to 70° C., more preferably in the range of from 30° C. to 55° C., most preferably 50° C.

Preferably, the total concentration of all carbamoylases $E_1$ in the reaction solution in step (iii) is in the range of from 1 µM to 10 mM, preferably 10 µM to 1 mM, more preferably 0.1 mM to 0.5 mM, most preferably 0.4 mM.

In alternative preferred embodiments, the total concentration of all carbamoylases $E_1$ in the reaction solution in step (iii) is in the range of from 1 µg/l to 10 g/l, preferably 0.1 mg/l to 5 g/l, more preferably 1 mg/l to 1 g/l, more preferably 5 mg/l to 500 mg/l.

At the end of step (i), a mixture $M_I$ comprising compounds according to formula L-(I) and optionally compounds according to formula D-(I) is obtained, preferably a mixture $M_I$ comprising compounds according to formula L-(I) and compounds according to formula D-(I) is obtained.

4.7 Saponification

The L-glufosinate P ester according to formula L-(I) produced with the method according to the first or second aspect can then be saponified to produce LGA, for example in an acidic aqueous medium, preferably at pH<7, even more preferably at an pH between <6, more preferably at an pH<3, even more preferably at an pH of <1. These saponification conditions are known to the skilled person and described e.g by H. J. Zeiss, J. Org. Chem. 1991, 56, 1783-1788.

5. EXAMPLES

5.1 Example 1 Identification of Suitable Enzymes and Construction of Plasmids Genes of different origins encoding a hydantoinase (dihydropyrimidinase, EC 3.5.2.2), L-carbamoylase (N-carbamoyl-L-amino-acid hydrolase, EC 3.5.1.87) and hydantoin racemase (EC 5.1.99.5) were tested for their ability to react with different hydantoin substrates according to formula L-(III) and D-(III) to form the respective enantioselective L-glufosinate derivative according to formula L-(I).

5.1.1 Examined Enzymes

Details of the strains and genes of the respective enzymes that were used in the examples are summarized in table 4.

TABLE 4

| Plasmid | Enzyme | Donor Strain | Gene name | SEQ ID NO: of the poly-nucleotides | SEQ ID NO: of the poly-peptides |
|---|---|---|---|---|---|
| pOM22c | L-carbamoylase | *Arthrobacter* sp. DSM 3747 | hyuC | SEQ ID NO: 27 | SEQ ID NO: 1 |
| pOM22c | hydantoinase | *Arthrobacter* sp. DSM 9771 | hyuH | SEQ ID NO: 28 | SEQ ID NO: 10 |
| pOM21c | hydantoin racemase | *Arthrobacter* sp. DSM 3745 | hyuR | SEQ ID NO: 29 | SEQ ID NO: 17 |

5.1.2 Cloning of the Enzymes

Cloning of the hydantoin racemase and generation of the plasmid pOM21c (FIG. 1) was carried out as described in example 1 of WO 2004/111227 A2. In particular, a polynucleotide was used which comprised the respective gene (SEQ ID NO: 29) and additional sequences for NdeI and PstI restriction sites.

Cloning of hydantoinase and L-carbamoylase into the rhamnose expression vector pJOE4036 was carried out in a plasmid derivative of the rhamnose expression vector pJOE4036.

Polynucleotides comprising the genes of the respective enzymes (SEQ ID NOs: 27, 28) were synthesized by GeneArt (ThermoFisher Scientific (Waltham, USA)). The polynucleotides carried additional sequences for EcoR1 and HindIII restriction sites. Both enzymes were cloned into pJOE4036 using those restriction sites resulting in the plasmid pOM22c, under the control of a rhamnose promotor (FIG. 2).

5.2 Example 2: Production of Strains Positive for Hydantoinase, L-Carbamoylase and Hydantoin Racemase Chemically competent *E. coli* ET5 cells (as described in WO 2004/042047 A1) were transformed with 10 ng of the plasmid pOM22c generated according to Example 1.

The generated strain which was positive for hydantoinase- and carbamoylase was rendered chemically competent and transformed with 10 ng of the plasmid pOM21c.

An *E. coli* ET5 strain transformed with pOM21c or pOM22c was incubated under shaking (250 U/min) at 30° C. for 18 hours in LB medium containing ampicillin (100 µg/l), chloramphenicol (50 µg/l), and 2 g/l rhamnose.

The biomass was separated by centrifugation, resuspended in 50 mM phosphate buffer (pH 7.2) and applied in biotransformation tests in the following examples. The concentration of the biomass in the solution was 40-50 g/l. The solution was used as catalyst ("catalyst 1") in the following.

The concentration of the respective polypeptide carbamoylase, hydantoinase and racemase in the obtained solution may be determined by SDS page and analysis of the respective bands via the software GelQuant® (BiochemLabSolutions).

5.3 Inventive Example 11 and Comparative Examples C1 to C4: Production of P-Alkyl Phosphinothricin Ester Using the Strains Produced in Examples 1 and 2

In the following examples, different hydantoin substrates were tested to determine whether the respective polypeptide catalyzed the reaction of the respective substrate enantioselectively to give the corresponding L amino acid.

5.3.1 Comparative Example C1

In comparative example C1, a racemic mixture Mc1 of 1.25 mmol L-(IV)$_{c1}$ and 1.25 mmol D-(IV)$_{c1}$, wherein L-(IV)$_{c1}$ and D-(IV)$_{c1}$ are hydantoins with the following formulae, was used as substrate:

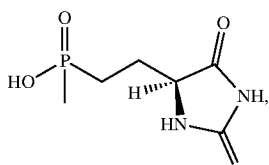
L-(IV)$_{C1}$

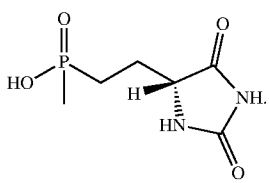
D-(IV)$_{C1}$

The mixture Mc1 was dissolved in a stirring reactor with 25 ml water. 2.4 g of the catalyst 1 was added, followed by the addition of 50 µl CoCl$_2$ solution. The suspension was set to pH 7.5 with 0.5 M NaOH. The total volume was replenished with water to 50 ml, so that the concentration of each enantiomer L-(IV)$_{c1}$ and D-(IV)$_{c1}$ was 0.025 mol/l. The pH was held between 7.0 and 7.5 by HCl-titration or NaOH-titration. The temperature was maintained at 37° C. by a thermostat during the reaction.

The reaction was stopped after 120 hours by addition of 2 N HCl until pH 2.5 was reached. The biomass was separated by centrifugation or filtration.

The enzyme reaction was monitored by ninhydrin test to determine the formation of amino acids. No formation of amino acids was detected by the ninhydrine test.

5.3.2 Comparative Example C2

In comparative example C2, a racemic mixture Mc2 of 1.25 mmol L-(V)$_{c2}$ and 1.25 mmol D-(V)$_{c2}$, wherein L-(V)$_{c2}$ and D-(V)$_{c2}$ are carbamoylates with the following formulae, was used as substrate:

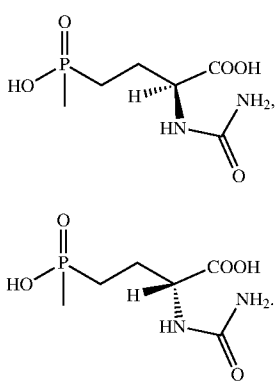
L-(V)$_{C2}$

D-(V)$_{C2}$

The mixture Mc2 was dissolved in a stirring reactor with 25 ml water. 2.4 g of the catalyst 1 was added, followed by the addition of 50 µl CoCl$_2$ solution. The suspension was set to pH 7.5 with 0.5 M NaOH. The total volume was replenished with water to 50 ml, so that the concentration of each enantiomer L-(V)$_{c2}$ and D-(V)$_{c2}$ was 0.025 mol/l. The pH was held between 7.0 and 7.5 by HCl-titration or NaOH-titration. The temperature was maintained at 37° C. by a thermostat during the reaction.

The reaction was stopped after 120 hours by addition of 2 N HCl until pH 2.5 was reached. The biomass was separated by centrifugation or filtration.

The enzyme reaction was monitored by ninhydrin test to determine the formation of amino acids. No formation of amino acids was detected by the ninhydrine test.

5.3.3 Example C3 (not According to the Invention)

In example C3, a racemic mixture Mc3 of 1.25 mmol L-(VI)$_{c3}$ and 1.25 mmol D-(VI)$_{c3}$, wherein L-(VI)$_{c3}$ and D-(VI)$_{c3}$ were hydantoins with the following formulae, was used as substrate:

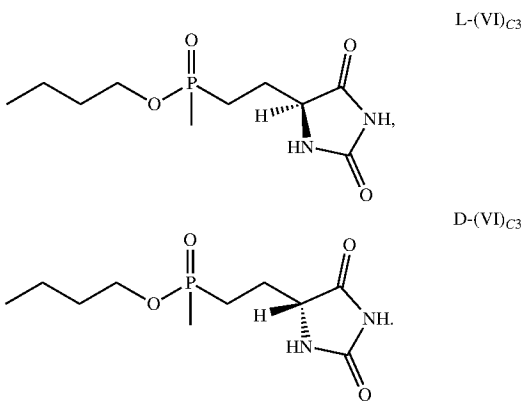
L-(VI)$_{C3}$

D-(VI)$_{C3}$

The mixture M$_{II}$ was dissolved in a stirring reactor with 25 ml water. 2.4 g of the catalyst 1 was added, followed by the addition of 50 µl CoCl$_2$ solution. The suspension was set to pH 7.5 with 0.5 M NaOH. The total volume was replenished with water to 50 ml, so that the concentration of each enantiomer L-(VI)$_{c3}$ and D-(VI)$_{c3}$ was 0.025 mol/l. The pH was held between 7.0 and 7.5 by HCl-titration or NaOH-titration. The temperature was maintained at 37° C. by a thermostat during the reaction.

The reaction was stopped after 120 hours by addition of 2 N HCl until pH 2.5 was reached. The biomass was separated by centrifugation or filtration.

The enzyme reaction was monitored by ninhydrin test to determine the formation of amino acids. Formation of amino acids was detected by the ninhydrine test.

In a final step the reaction mixture was saponified at 100° C. for 10 hours by adding 6 M HCl to obtain L-glufosinate and, if present, D-glufosinate. The final reaction mixture was analysed by LC-MS with a CR-I column as described under item 5.4 to determine the enantiomeric excess ("ee") of either D- or L-glufosinate. An ee of LGA of 79% over the D-enantiomer was detected. The ee of the L-enantiomer ("ee$_L$") is determined by the following formula in the context of the invention, wherein m$_L$ and m$_D$ are the detected molar masses of L- and D-glufosinate, respectively:

$$ee_L = \frac{(m_L - m_D) \times 100\%}{(m_L + m_D)}.$$

5.3.4 Example C4 (not According to the Invention)

In example C4, a racemic mixture Mc4 of 1.25 mmol L-(VII)$_{c4}$ and 1.25 mmol D-(VII)$_{c4}$, wherein L-(VII)$_{c4}$ and D-(VII)$_{c4}$ were hydantoins with the following formulae, was used as substrate:

L-(VII)$_{C4}$

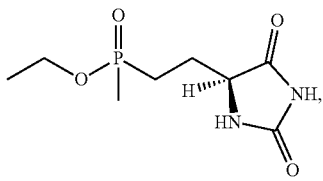

D-(VII)$_{C4}$

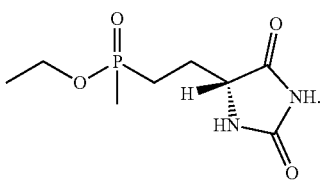

The mixture Mc4 was dissolved in a stirring reactor with 25 ml water. 2.4 g of the catalyst 1 was added, followed by the addition of 50 μl CoCl$_2$ solution. The suspension was set to pH 7.5 with 0.5 M NaOH. The total volume was replenished with water to 50 ml, so that the concentration of each enantiomer L-(VII)$_{c4}$ and D-(VII)$_{c4}$ was 0.025 mol/l. The pH was held between 7.0 and 7.5 by HCl-titration or NaOH-titration. The temperature was maintained at 37° C. by a thermostat during the reaction.

The reaction was stopped after 120 hours by addition of 2 N HCl until pH 2.5 was reached. The biomass was separated by centrifugation or filtration.

The enzyme reaction was monitored by ninhydrin test to determine the formation of amino acids. Formation of amino acids was detected by the ninhydrine test.

In a final step the reaction mixture was saponified at 100° C. for 10 hours by adding 6 M HCl to obtain L-glufosinate and, if present, D-glufosinate. The final reaction mixture was analysed by LC-MS with a CR-I column as described under item 5.4 to determine the enantiomeric excess ("ee") of either D- or L-glufosinate. An ee of LGA of 77% over the D-enantiomer was detected.

5.3.5 Inventive Example 11

In example 11, a mixture Mm of 0.625 mmol L-(VIII)$_{I1}$, 0.625 mmol L-(VIII)$_{I1'}$, 0.625 mmol D-(VIII)$_{I1}$, and 0.625 mmol D-(VIII)$_{I1'}$, wherein L-(VIII)$_{I1}$, L-(VIII)$_{I1'}$, D-(VIII), and D-(VIII) n' were hydantoins with the following formulae, is used as substrate:

L-(VIII)$_{I1}$

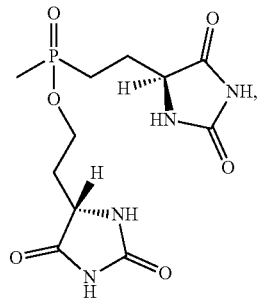

D-(VIII)$_{I1}$

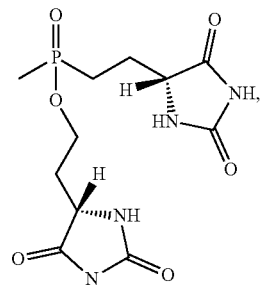

D-(VIII)$_{I1'}$

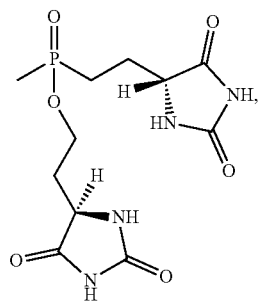

L-(VIII)$_{I1'}$

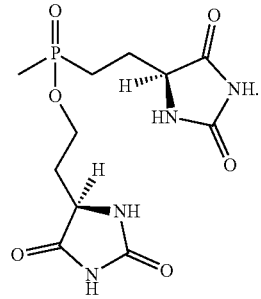

These compounds may be obtained from mixtures of L-homoserine/D-homoserine by a synthesis method as set forth in CN 111662325 A.

The mixture Mm is dissolved in a stirring reactor with 25 ml water. 2.4 g of the catalyst 1 is added, followed by the addition of 50 μl CoCl$_2$ solution. The suspension is set to pH 7.5 with 0.5 M NaOH. The total volume is replenished with water to 50 ml, so that the concentration of each isomer L-(VIII)$_{I1}$, L-(VIII)$_{I1'}$, D-(VIII)$_{I1}$, and D-(VIII)$_{I1'}$ is 0.0125 mol/l. The pH is held between 7.0 and 7.5 by HCl-titration or NaOH-titration. The temperature is maintained at 37° C. by a thermostat during the reaction.

The reaction is stopped after 120 hours by addition of 2 N HCl until pH 2.5 is reached. The biomass is separated by centrifugation or filtration.

The enzyme reaction is monitored by ninhydrin test to determine the formation of amino acids. Formation of amino acids may be detected by the ninhydrine test.

In a final step the reaction mixture is saponified at 100° C. for 10 hours by adding 6 M HCl to obtain L-glufosinate and, if present, D-glufosinate. The final reaction mixture is analysed by LC-MS with a CR-I column as described under item 5.4 to determine the enantiomeric excess ("ee") of either D- or L-glufosinate. An ee of LGA over the D-enantiomer may be detected (not quantified). The ee of the L-enantiomer ("ee$_L$") is determined by the following formula in the context of the invention, wherein m$_L$ and m$_D$ are the detected molar masses of L- and D-glufosinate, respectively:

$$ee_L = \frac{(m_L - m_D) \times 100\%}{(m_L + m_D)}.$$

5.3.5 Results

The results of the examples C1, C2, C3, C4 are summarized in table 5.

TABLE 5

| Example | substrate | Ninhydrine test | $ee_L$ |
|---|---|---|---|
| C1 | L-(IV)$_{C1}$, D-(IV)$_{C1}$ | Negative | — |
| C2 | L-(V)$_{C2}$, D-(V)$_{C2}$ | Negative | — |
| C3 | L-(VI)$_{C3}$, D-(VI)$_{C3}$ | Positive | 79% |
| C4 | L-(VII)$_{C4}$, D-(VII)$_{C4}$ | Positive | 77% |

5.3.6 Conclusion

The results as summarized in table 5 show that certain hydantoin esters such as the alkylated hydantoin esters can be used as substrates for the enzymatic enantioselective synthesis of L-glufosinate (C3, C4). In contrast, substrates in which the phosphinic acid group is not protected are not accepted by the catalytic system (C1, C2). In this regard, C2 suggests that at least one reason for this is that the L-carbamoylase enzyme does not accept the respective substrate in which the phosphinic acid function is not protected by an ester group.

Analogous results are obtained, when compound mixtures according to the scope of the invention, i.e. of compounds according to L-(III) and D-(III), wherein R$^{3L}$ and R$^{3D}$ are preferably identical, such as in inventive example 11, are used.

Moreover, in contrast to the process for enantioselective production according to the prior art (CN 111662325 A), the ee excess could be maintained throughout the process, because saponification is carried out not at the hydantoin stage, but at the stage of the amino acid ester.

5.4 Analytical Methods

L-glufosinate and D-glufosinate were detected by LC-MS ("Liquid Chromatography-Mass Spectrometry") with a chiral column [Daicel CROWNPAK CR-I-(−)] as follows. For hydantoins, a Daicel Chiralpak IA-U column may also be used.

This detection method may also be used for detection and quantification of the the LGA P-(n-butyl) ester according to formula L-(I) (II)* according to Assay A$_L$ (item 4.5.3.1);

the D-glufosinate P-(n-butyl) ester according to formula D-(I)(II)* according to Assay A$_D$ (item 4.5.3.2);

the carbamoyl LGA P-(n-butyl) ester according to formula L-(II)(II)* according to Assay D$_L$ (item 4.5.9.1);

the carbamoyl D-glufosinate P-(n-butyl) ester according to formula D-(II)(II)* according to Assay D$_D$ (item 4.5.9.2);

the L-enantiomer of a n-butyl ester of hydantoin glufosinate of the formula L-(III)(II)* according to Assay G (item 4.5.14.3).

the D-enantiomer of a n-butyl ester of hydantoin glufosinate of the formula D-(III)(II)* according to Assay G (item 4.5.14.3).

5.4.1 Acquisition Method Details

CR-I-(−), 3.0 mm I.D.×150 mm, 5 μm, Crownpak, Part. No. 54784
MS QQQ Mass Spectrometer 6420, Agilent
ESI+
MS2 SIM, Glufosinat m/z 182.06 Unit Positive
Centroid

5.4.2 Source Parameter

Parameter Value (+); Gas Temp (° C.): 350; Gas Flow (l/min): 12; Nebulizer (psi): 25; Capillary (V): 3000; Sampler Module: G1329B; Injection Volume 1.00 μL; 5° C.

5.4.3 Binary Pump Module

G1312B
Flow: 0.200 mL/min;
Channel A: H$_2$O with trifluoroacetic acid (TFA) pH1.15;
Channel B: ACN (acetonitrile);
isocratic 80.0% A/20.0% B; stop time 7.00 min
Column Comp. Module: G1316A
Temperature 5.0° C.

---

The invention claimed is:

1. A method for the production of an L-glufosinate P-ester according to formula L-(I), the method comprising:

(c) reacting a compound according to formula L-(II) to give a compound according to formula L-(I)

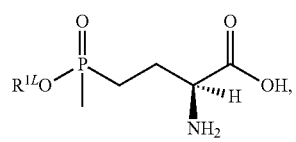

L-(I)

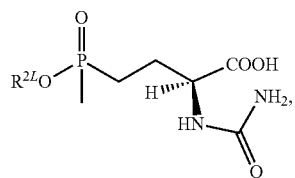

L-(II)

wherein the reaction according to (c) is catalyzed by an L-carbamoylase $E_1$ categorized in EC class 3.5.1.87, wherein $R^{1L}$ and $R^{2L}$ are radicals selected from the group consisting of formulae (VIII), (IX), and (X)

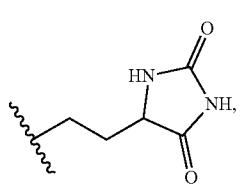

(VIII)

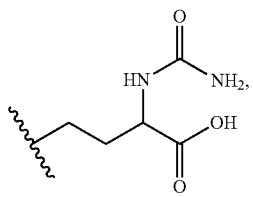

(IX)

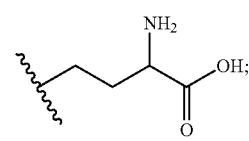

(X)

and wherein $R^{1L}=R^{2L}$.

2. The method according to claim 1, wherein $R^{1L}$ and $R^{2L}$ are radicals that are each independently selected from the group consisting of formulae (IX) and (X).

3. The method according to claim 1, wherein a polypeptide sequence of the L-carbamoylase $E_1$ is selected from the group consisting of SEQ ID NO: 1, SEQ ID NO: 2, SEQ ID NO: 3 SEQ ID NO: 4 SEQ ID NO: 5, SEQ ID NO: 6, SEQ ID NO: 7, SEQ ID NO: 8, SEQ ID NO: 9, and variant amino acid sequences having at least 90% sequence identity to one of SEQ ID NOS: 1-9.

4. The method according to claim 1, wherein the compound according to formula L-(II) is obtained by (b) in which a compound according to formula L-(III) is reacted to give a compound according to formula L-(II):

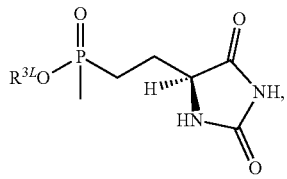

L-(III)

wherein the reaction according to (b) is catalyzed by a hydantoinase $E_2$ categorized in EC class 3.5.2.2, and wherein $R^{3L}$ is a radical that is selected from the group consisting of formulae (VIII), (IX), and (X).

5. The method according to claim 4, wherein $R^{3L}$ is a radical of the formula (VIII).

6. The method according to claim 4, wherein a polypeptide sequence of the hydantoinase $E_2$ is selected from the group consisting of SEQ ID NO: 10, SEQ ID NO: 11, SEQ ID NO: 12, SEQ ID NO: 13, SEQ ID NO: 14, SEQ ID NO: 16, and variant amino acid sequences having at least 90% sequence identity to one of SEQ ID NOS: 10-16.

7. The method according to claim 4, wherein the hydantoinase $E_2$ is an L-hydantoinase $E_2$.

8. The method according to claim 4, wherein the compound according to formula L-(III) is obtained by (a) in which a compound according to formula D-(III) is reacted to give a compound according to formula L-(III):

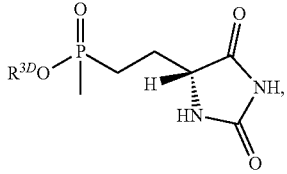

D-(III)

and wherein $R^{3D}$ is a radical that is selected from the group consisting of formulae (VIII), (IX), and (X).

9. The method according to claim 8, wherein $R^{3D}$ is a radical of the formula (VIII).

10. The method according to claim 8, wherein the reaction according to (a) is catalyzed by a hydantoin racemase $E_3$ categorized in EC class 5.1.99.5.

11. The method according to claim 10, wherein a polypeptide sequence of the hydantoin racemase $E_3$ is selected from the group consisting of SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, and variant amino acid sequences having at least 90% sequence identity to one of SEQ ID NOS: 18-26.

12. The method according to claim 1, wherein the compound according to formula L-(I) is saponified to give L-glufosinate.

13. A method for the production of an L-glufosinate P-ester according to formula L-(I):

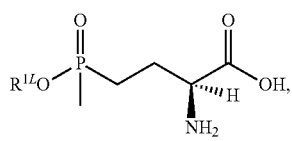

L-(I)

the method comprising:
(i-A) providing a mixture MIIA comprising at least one compound L-(III) and at least one compound D-(III), wherein L-(III) and D-(III) have the following formulae:

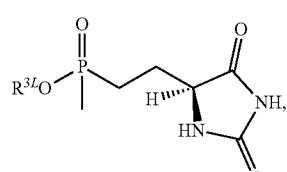

L-(III)

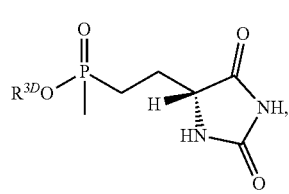

D-(III)

(i-B) (a) reacting at least a part of the compounds according to formula D-(III) comprised by the mixture $M_{IIIA}$ into the compound according to formula L-(III) to form a composition $M_{IIIB}$ comprising compounds according to formula L-(III) and compounds according to formula D-(III), and
(ii) subjecting composition $M_{IIIB}$ to a reaction according to (b), giving a composition Mu comprising at least one compound according to formula L-(II) and at least one compound according to formula D-(II), wherein the reaction according to (b) is catalyzed by a hydantoinase $E_2$ categorized in EC class 3.5.2.2, wherein L-(II) and D-(II) have the following formulae:

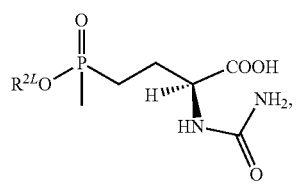

L-(II)

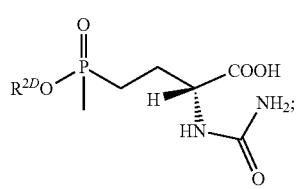

D-(II)

and
(iii) subjecting composition Mu to a reaction according to (c), wherein the reaction according to (c) is catalyzed by an L-carbamoylase $E_1$, giving a composition $M_I$ comprising at least one compound according to formula L-(I) and at least one compound according to formula D-(I), wherein a molar ratio of all compounds according to formula L-(I) in composition $M_1$ to all compounds according to formula D-(I) in composition $M_I$ is greater than a molar ratio of all compounds according to formula L-(III) in $M_{IIIA}$ to all compounds of formula D-(III) in $M_{IIIA}$, wherein D-(I) has the following formula:

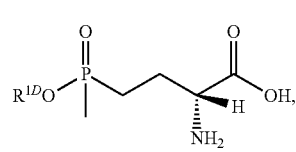

D-(I)

and
wherein $R^{1L}$, $R^{1D}$, $R^{2L}$, $R^{2D}$, $R^{3L}$ and $R^{3D}$ are each the same radical selected from the group consisting of formulae (VIII), (IX), and (X) having the following formulae:

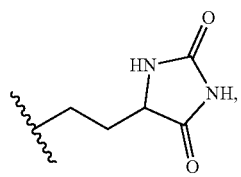

(VIII)

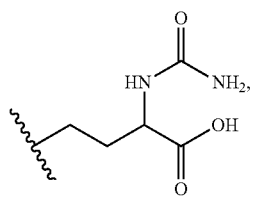

(IX)

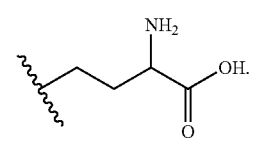

(X)

* * * * *

SEQUENCE LISTING

<160> NUMBER OF SEQ ID NOS: 29

<210> SEQ ID NO 1
<211> LENGTH: 414
<212> TYPE: PRT
<213> ORGANISM: Arthrobacter sp.
<220> FEATURE:
<221> NAME/KEY: misc_feature
<222> LOCATION: 1..414
<223> OTHER INFORMATION: Arthrobacter sp. DSM 3747 (strain)
<220> FEATURE:
<221> NAME/KEY: gene
<222> LOCATION: 1..414
<223> OTHER INFORMATION: HyuC

<400> SEQUENCE: 1

Met Thr Leu Gln Lys Ala Gln Ala Glu Arg Ile Glu Lys Glu Ile Trp
1               5                   10                  15

Glu Leu Ser Arg Phe Ser Ala Glu Gly Pro Gly Val Thr Arg Leu Thr

```
            20                  25                  30
Tyr Thr Pro Glu His Ala Ala Arg Glu Thr Leu Ile Ala Ala Met
        35                  40                  45
Glu Ala Ala Leu Ser Val Arg Glu Asp Ala Leu Gly Asn Ile Ile
        50                  55                  60
Gly Arg Arg Glu Gly Thr Asp Pro Gln Leu Pro Ala Ile Ala Val Gly
65                  70                  75                  80
Ser His Phe Asp Ser Val Arg Asn Gly Gly Met Phe Asp Gly Thr Ala
                85                  90                  95
Gly Val Val Cys Ala Leu Glu Ala Ala Arg Val Met Leu Glu Ser Gly
            100                 105                 110
Tyr Val Asn Arg His Pro Phe Glu Phe Ile Ala Ile Val Glu Glu Glu
            115                 120                 125
Gly Ala Arg Phe Ser Ser Gly Met Leu Gly Gly Arg Ala Ile Ala Gly
            130                 135                 140
Leu Val Ala Asp Arg Glu Leu Asp Ser Leu Val Asp Glu Asp Gly Val
145                 150                 155                 160
Ser Val Arg Gln Ala Ala Thr Ala Phe Gly Leu Lys Pro Gly Glu Leu
                165                 170                 175
Gln Ala Ala Arg Ser Ala Ala Asp Leu Arg Ala Phe Ile Glu Leu
            180                 185                 190
His Ile Glu Gln Gly Pro Ile Leu Glu Gln Glu Gln Ile Glu Ile Gly
            195                 200                 205
Val Val Thr Ser Ile Val Gly Val Arg Ala Leu Arg Val Ala Val Lys
            210                 215                 220
Gly Arg Ser Ala His Ala Gly Thr Thr Pro Met His Leu Arg Gln Asp
225                 230                 235                 240
Ala Leu Val Pro Ala Ala Leu Met Val Arg Glu Val Asn Arg Phe Val
                245                 250                 255
Asn Glu Ile Ala Asp Gly Thr Val Ala Thr Val Gly His Leu Thr Val
                260                 265                 270
Ala Pro Gly Gly Gly Asn Gln Val Pro Gly Glu Val Glu Phe Thr Leu
                275                 280                 285
Asp Leu Arg Ser Pro His Glu Glu Ser Leu Arg Val Leu Ile Asn Arg
            290                 295                 300
Ile Ser Val Met Val Gly Glu Val Ala Ser Gln Ala Gly Val Ala Ala
305                 310                 315                 320
Asp Val Asp Glu Phe Phe Asn Leu Ser Pro Val Gln Leu Ala Pro Thr
                325                 330                 335
Met Val Asp Ala Val Arg Glu Ala Ala Ser Ala Leu Gln Phe Thr His
                340                 345                 350
Arg Asp Ile Ser Ser Gly Ala Gly His Asp Ser Met Phe Ile Ala Gln
            355                 360                 365
Val Thr Asp Val Gly Met Val Phe Val Pro Ser Arg Ala Gly Arg Ser
            370                 375                 380
His Val Pro Glu Glu Trp Thr Asp Phe Asp Asp Leu Arg Lys Gly Thr
385                 390                 395                 400
Glu Val Val Leu Arg Val Met Lys Ala Leu Asp Arg Gly Ser
                405                 410

<210> SEQ ID NO 2
<211> LENGTH: 409
<212> TYPE: PRT
<213> ORGANISM: Geobacillus stearothermophilus
```

```
<220> FEATURE:
<221> NAME/KEY: gene
<222> LOCATION: 1..409
<223> OTHER INFORMATION: AmaB

<400> SEQUENCE: 2
```

Met Ile Gln Gly Glu Arg Leu Trp Gln Arg Leu Met Glu Leu Gly Glu
1               5                   10                  15

Val Gly Lys Gln Pro Ser Gly Gly Val Thr Arg Leu Ser Phe Thr Ala
            20                  25                  30

Glu Glu Arg Arg Ala Lys Asp Leu Val Ala Ser Tyr Met Arg Glu Ala
                35                  40                  45

Gly Leu Phe Val Tyr Glu Asp Ala Ala Gly Asn Leu Ile Gly Arg Lys
    50                  55                  60

Glu Gly Thr Asn Pro Asp Ala Thr Val Val Leu Val Gly Ser His Leu
65              70                  75                  80

Asp Ser Val Tyr Asn Gly Gly Cys Phe Asp Gly Pro Leu Gly Val Leu
                85                  90                  95

Ala Gly Val Glu Val Val Gln Thr Met Asn Glu His Gly Val Val Thr
            100                 105                 110

His His Pro Ile Glu Val Ala Phe Thr Asp Glu Gly Ala Arg
                115                 120                 125

Phe Arg Phe Gly Met Ile Gly Ser Arg Ala Met Ala Gly Thr Leu Pro
    130                 135                 140

Pro Glu Ala Leu Glu Cys Arg Asp Ala Glu Gly Ile Ser Leu Ala Glu
145                 150                 155                 160

Ala Met Lys Gln Ala Gly Leu Asp Pro Asp Arg Leu Pro Gln Ala Ala
                165                 170                 175

Arg Lys Pro Gly Thr Val Lys Ala Tyr Val Glu Leu His Ile Glu Gln
            180                 185                 190

Gly Arg Val Leu Glu Glu Thr Gly Leu Pro Val Gly Ile Val Thr Gly
        195                 200                 205

Ile Ala Gly Leu Ile Trp Val Lys Phe Thr Ile Glu Gly Lys Ala Glu
210                 215                 220

His Ala Gly Ala Thr Pro Met Ser Leu Arg Arg Asp Pro Met Ala Ala
225                 230                 235                 240

Ala Ala Gln Ile Ile Ile Val Ile Glu Glu Ala Arg Arg Thr Gly
                245                 250                 255

Thr Thr Val Gly Thr Val Gly Gln Leu His Val Tyr Pro Gly Gly Ile
            260                 265                 270

Asn Val Ile Pro Glu Arg Val Glu Phe Val Leu Asp Leu Arg Asp Leu
        275                 280                 285

Lys Ala Glu Val Arg Asp Gln Val Trp Lys Ala Ile Ala Val Arg Ala
    290                 295                 300

Glu Thr Ile Ala Lys Glu Arg Asn Val Arg Val Thr Thr Glu Arg Leu
305                 310                 315                 320

Gln Glu Met Pro Pro Val Leu Cys Ser Asp Val Lys Arg Ala Ala
                325                 330                 335

Glu Ala Ala Cys Gln Lys Leu Gly Tyr Pro Ser Phe Trp Leu Pro Ser
            340                 345                 350

Gly Ala Ala His Asp Ser Val Gln Leu Ala Pro Ile Cys Pro Ile Gly
        355                 360                 365

Met Ile Phe Val Arg Ser Gln Asp Gly Val Ser His Ser Pro Ala Glu
    370                 375                 380

```
Trp Ser Thr Lys Glu Asp Cys Ala Ala Gly Ala Glu Val Leu Tyr His
385                 390                 395                 400

Thr Val Trp Gln Leu Ala Gln Gly Glu
                405

<210> SEQ ID NO 3
<211> LENGTH: 420
<212> TYPE: PRT
<213> ORGANISM: Pseudomonas sp.
<220> FEATURE:
<221> NAME/KEY: misc_feature
<222> LOCATION: 1..420
<223> OTHER INFORMATION: Pseudomonas sp. QR-101 (strain)
<220> FEATURE:
<221> NAME/KEY: gene
<222> LOCATION: 1..420
<223> OTHER INFORMATION: AtcC

<400> SEQUENCE: 3

Met Ser Gly Val Asn Ser Met Asn Arg Thr Pro Gly Ile Gln Pro Glu
1               5                   10                  15

Arg Leu Trp Gly Asp Leu Met Ser Thr Ala Lys Phe Gly Ala Leu Gly
            20                  25                  30

Glu Thr Gly Met Arg Arg Leu Ala Leu Ser Asn Glu Asp Arg Gln Val
        35                  40                  45

Arg Asp Trp Phe Val Ala Gln Cys Arg Glu Leu Gly Cys Thr Ile Asp
    50                  55                  60

Ile Asp Gln Ile Gly Asn Ile Phe Ala Thr Tyr Pro Gly Leu Asp Ala
65                  70                  75                  80

Ser Leu Ala Pro Ile Ala Met Gly Ser His Leu Asp Thr Gln Pro Ala
                85                  90                  95

Gly Gly Arg Phe Asp Gly Ile Leu Gly Val Leu Ala Gly Ile Glu Val
            100                 105                 110

Leu Arg Ser Leu His Asp Ala Ser Val Arg Pro Ala His Pro Ile Thr
        115                 120                 125

Val Ile Val Trp Thr Asn Glu Glu Gly Ser Arg Phe Ala Pro Ala Met
    130                 135                 140

Met Gly Ser Gly Val Tyr Cys Gly Ala His Gln Trp Glu Thr Val Ala
145                 150                 155                 160

Ala Thr Cys Asp Lys Ser Gly Val Ser Val Ala Gln Ala Leu Asp Ala
                165                 170                 175

Ile Gly Tyr Ala Gly Glu His Glu Pro Gly Phe Met Gln Phe Ser Ala
            180                 185                 190

Tyr Leu Glu Leu His Ile Glu Gln Gly Pro Val Leu Glu Ala Glu Asn
        195                 200                 205

Ile Glu Ile Gly Val Val Asp Ala Val Gln Gly Val Cys Trp Leu Asp
    210                 215                 220

Ile Lys Val Pro Gly Val Ser Ala His Ala Gly Gly Arg Pro Met Thr
225                 230                 235                 240

Met Arg Asp Asp Ala Leu Val Ala Ala Ser Lys Ile Val Leu Ala Val
                245                 250                 255

Glu Ala Val Ala Ser Ala His Leu Pro Gly Val Gly Thr Ile Gly Tyr
            260                 265                 270

Ile Ser Ala Gly Pro Asn Ser Arg Asn Val Ile Pro Gly Thr Val Ala
        275                 280                 285

Leu Glu Val Asp Leu Arg His Pro Asp Asp Ala Glu Leu Ser Ala Leu
    290                 295                 300
```

```
Glu Asn Glu Val Thr Ala Glu Ile Lys Arg Ile Cys Pro Ala Ala Glu
305                 310                 315                 320

Val Gln Arg Val Trp Arg Lys Pro Val Thr Phe Asp Ser Arg Ile
            325                 330                 335

Val Asp Ala Ile Ala Ala Arg Thr Glu Ala Leu Gly Tyr Ser Ala Arg
            340                 345                 350

Arg Met Val Ser Gly Ala Gly His Asp Ala Ala His Val Ala Gly Ile
            355                 360                 365

Ala Pro Ser Ala Met Ile Phe Ile Pro Ser Tyr Leu Gly Leu Ser His
            370                 375                 380

Asn Val Arg Glu Tyr Ser Ser Pro Glu Gln Cys Ala Gln Gly Ala Thr
385                 390                 395                 400

Val Leu Leu Gly Ala Val Leu Asp Leu Asp Asn Leu Leu Ala Asp
            405                 410                 415

Ser Arg Thr Gly
            420

<210> SEQ ID NO 4
<211> LENGTH: 409
<212> TYPE: PRT
<213> ORGANISM: Geobacillus kaustophilus
<220> FEATURE:
<221> NAME/KEY: gene
<222> LOCATION: 1..409
<223> OTHER INFORMATION: Lnc

<400> SEQUENCE: 4

Met Ile Gln Gly Glu Arg Leu Trp Gln Arg Leu Met Glu Leu Gly Glu
1               5                   10                  15

Val Gly Lys Lys Pro Ser Gly Gly Val Thr Arg Leu Ser Phe Thr Ala
            20                  25                  30

Glu Glu Arg Arg Ala Lys Asp Leu Val Ala Ser Tyr Met Arg Glu Ala
            35                  40                  45

Gly Leu Phe Val Tyr Glu Asp Thr Ala Gly Asn Leu Ile Gly Arg Lys
        50                  55                  60

Glu Gly Ala Asn Pro Asp Ala Pro Val Val Leu Val Gly Ser His Leu
65                  70                  75                  80

Asp Ser Val Tyr Asn Gly Gly Cys Phe Asp Gly Pro Leu Gly Val Leu
                85                  90                  95

Ala Gly Val Glu Val Val Gln Thr Met Asn Glu His Gly Val Val Thr
            100                 105                 110

His His Pro Ile Glu Val Val Ala Phe Thr Asp Glu Glu Gly Ala Arg
        115                 120                 125

Phe Arg Phe Gly Met Ile Gly Ser Arg Ala Met Ala Gly Thr Leu Leu
130                 135                 140

Pro Glu Ala Leu Glu Cys Arg Asp Ala Asn Gly Ile Ser Ile Ala Glu
145                 150                 155                 160

Ala Met Arg Gln Thr Gly Leu Asp Pro Asp Arg Leu Pro Gln Ala Ala
                165                 170                 175

Arg Lys Pro Gly Thr Val Lys Ala Tyr Val Glu Leu His Ile Glu Gln
            180                 185                 190

Gly Arg Val Leu Glu Glu Ala Gly Leu Pro Val Gly Ile Val Thr Gly
        195                 200                 205

Ile Ala Gly Leu Ile Trp Val Lys Phe Ile Glu Gly Lys Ala Glu
210                 215                 220

His Ala Gly Ala Thr Pro Met Ser Leu Arg Arg Asp Pro Met Ala Ala
```

```
                225                 230                 235                 240
    Ala Ala Gln Ile Ile Thr Val Ile Glu Glu Ala Arg Arg Thr Gly
                    245                 250                 255

Thr Thr Val Gly Thr Val Gly Gln Leu His Val Tyr Pro Gly Ile
                    260                 265                 270

Asn Val Ile Pro Glu Arg Val Glu Phe Val Leu Asp Leu Arg Asp Leu
                    275                 280                 285

Lys Ala Glu Val Arg Asp Gln Val Trp Asn Asp Ile Ala Ser Arg Ala
                    290                 295                 300

Glu Thr Ile Ala Lys Glu Arg Asn Val Arg Leu Thr Thr Glu Arg Leu
    305                 310                 315                 320

Gln Glu Met Ala Pro Val Leu Cys Ser Glu Val Lys Gln Ala Ala
                    325                 330                 335

Glu Arg Ala Cys Lys Gln Leu Gly Tyr Pro Pro Phe Trp Leu Pro Ser
                    340                 345                 350

Gly Ala Ala His Asp Gly Val Gln Leu Ala Pro Ile Cys Pro Ile Gly
                    355                 360                 365

Met Ile Phe Val Arg Ser Gln Asp Gly Val Ser His Ser Pro Ala Glu
                    370                 375                 380

Trp Ser Thr Lys Glu Asp Cys Ala Val Gly Ala Glu Val Leu Tyr His
    385                 390                 395                 400

Thr Val Trp Gln Leu Ala Gln Gly Glu
                    405

<210> SEQ ID NO 5
    <211> LENGTH: 412
    <212> TYPE: PRT
    <213> ORGANISM: Paenarthrobacter aurescens
    <220> FEATURE:
    <221> NAME/KEY: gene
    <222> LOCATION: 1..412
    <223> OTHER INFORMATION: HyuC

<400> SEQUENCE: 5

Met Thr Leu Gln Lys Ala Gln Ala Glu Arg Ile Glu Lys Glu Ile Arg
    1               5                   10                  15

Glu Leu Ser Arg Phe Ser Ala Glu Gly Pro Gly Val Thr Arg Leu Thr
                    20                  25                  30

Tyr Thr Pro Glu His Ala Ala Arg Glu Thr Leu Ile Ala Ala Met
                    35                  40                  45

Lys Ala Ala Ala Leu Ser Val Arg Glu Asp Ala Leu Gly Asn Ile Ile
                    50                  55                  60

Gly Arg Arg Glu Gly Thr Asp Pro Glu Leu Pro Ala Ile Ala Val Gly
    65                  70                  75                  80

Ser His Phe Asp Ser Val Arg Asn Gly Gly Met Phe Asp Gly Thr Ala
                    85                  90                  95

Gly Val Val Cys Ala Leu Glu Ala Ala Arg Val Met Leu Glu Asn Gly
                    100                 105                 110

Tyr Val Asn Arg His Pro Phe Glu Phe Ile Ala Ile Val Glu Glu Glu
                    115                 120                 125

Gly Ala Arg Phe Ser Ser Gly Met Leu Gly Gly Arg Ala Ile Ala Gly
                    130                 135                 140

Leu Val Ala Asp Arg Glu Leu Asp Ser Leu Val Asp Glu Asp Gly Val
    145                 150                 155                 160

Ser Val Arg Gln Ala Ala Thr Ala Phe Gly Leu Lys Pro Gly Glu Leu
                    165                 170                 175
```

```
Gln Ala Ala Ala Arg Ser Ala Ala Asp Leu Arg Ala Phe Ile Glu Leu
            180                 185                 190

His Ile Glu Gln Gly Pro Ile Leu Glu Gln Gln Ile Glu Ile Gly
        195                 200                 205

Val Val Thr Ser Ile Val Gly Val Arg Ala Leu Arg Val Ala Val Lys
    210                 215                 220

Gly Arg Ser Asp His Ala Gly Thr Thr Pro Met His Leu Arg Gln Asp
225                 230                 235                 240

Ala Leu Val Pro Ala Ala Leu Met Val Arg Glu Val Asn Arg Phe Val
                245                 250                 255

Asn Glu Ile Ala Asp Gly Thr Val Ala Thr Val Gly His Leu Thr Val
            260                 265                 270

Ala Pro Gly Gly Gly Asn Gln Val Pro Gly Glu Val Asp Phe Thr Leu
        275                 280                 285

Asp Leu Arg Ser Pro His Glu Glu Ser Leu Arg Val Leu Ile Asp Arg
    290                 295                 300

Ile Ser Val Met Val Gly Glu Val Ala Ser Gln Ala Gly Val Ala Ala
305                 310                 315                 320

Asp Val Asp Glu Phe Phe Asn Leu Ser Pro Val Gln Leu Ala Pro Thr
                325                 330                 335

Met Val Asp Ala Val Arg Glu Ala Ala Ser Ala Leu Gln Phe Thr His
            340                 345                 350

Arg Asp Ile Ser Ser Gly Ala Gly His Asp Ser Met Phe Ile Ala Gln
        355                 360                 365

Val Thr Asp Val Gly Met Val Phe Val Pro Ser Arg Ala Gly Arg Ser
    370                 375                 380

His Val Pro Glu Glu Trp Thr Asp Phe Asp Leu Arg Lys Gly Thr
385                 390                 395                 400

Glu Val Val Leu Arg Val Met Lys Ala Leu Asp Arg
                405                 410

<210> SEQ ID NO 6
<211> LENGTH: 416
<212> TYPE: PRT
<213> ORGANISM: Sinorhizobium meliloti
<220> FEATURE:
<221> NAME/KEY: gene
<222> LOCATION: 1..416
<223> OTHER INFORMATION: SinmeB_2280

<400> SEQUENCE: 6

Met Ala Ala Pro Gly Glu Asn Arg Arg Val Asn Ala Asp Arg Leu Trp
1               5                   10                  15

Asp Ser Leu Met Glu Met Ala Lys Ile Gly Pro Gly Ala Gly Gly
            20                  25                  30

Asn Asn Arg Gln Thr Leu Thr Asp Ala Asp Gly Glu Gly Arg Arg Leu
        35                  40                  45

Phe Gln Ser Trp Cys Glu Glu Ala Gly Leu Ser Met Gly Val Asp Lys
    50                  55                  60

Met Gly Thr Met Phe Leu Thr Arg Pro Gly Thr Asp Pro Asp Ala Leu
65                  70                  75                  80

Pro Val His Ile Gly Ser His Leu Asp Thr Gln Pro Thr Gly Gly Lys
                85                  90                  95

Phe Asp Gly Val Leu Gly Val Leu Ser Gly Leu Glu Ala Val Arg Thr
            100                 105                 110
```

```
Met Asn Asp Leu Gly Ile Lys Thr Lys His Pro Ile Val Val Thr Asn
            115                 120                 125

Trp Thr Asn Glu Glu Gly Ala Arg Phe Ala Pro Ala Met Leu Ala Ser
130                 135                 140

Gly Val Phe Ala Gly Val His Thr Leu Glu Tyr Ala Tyr Ala Arg Lys
145                 150                 155                 160

Asp Pro Glu Gly Lys Ser Phe Gly Asp Glu Leu Lys Arg Ile Gly Trp
                165                 170                 175

Leu Gly Asp Glu Glu Val Gly Ala Arg Lys Met His Ala Tyr Phe Glu
            180                 185                 190

Tyr His Ile Glu Gln Gly Pro Ile Leu Glu Ala Glu Asn Lys Gln Ile
        195                 200                 205

Gly Val Val Thr His Cys Gln Gly Leu Trp Trp Leu Glu Phe Thr Leu
    210                 215                 220

Thr Gly Arg Glu Ala His Thr Gly Ser Thr Pro Met Asp Met Arg Val
225                 230                 235                 240

Asn Ala Gly Leu Ala Met Ala Arg Ile Leu Glu Met Val Gln Thr Val
                245                 250                 255

Ala Met Glu Asn Gln Pro Gly Ala Val Gly Gly Val Gly Gln Met Phe
            260                 265                 270

Phe Ser Pro Asn Ser Arg Asn Val Leu Pro Gly Lys Val Val Phe Thr
        275                 280                 285

Val Asp Ile Arg Ser Pro Asp Gln Ala Lys Leu Asp Gly Met Arg Ala
    290                 295                 300

Arg Ile Glu Ala Glu Ala Pro Lys Ile Cys Glu Arg Leu Gly Val Gly
305                 310                 315                 320

Cys Ser Ile Glu Ala Val Gly His Phe Asp Pro Val Thr Phe Asp Pro
                325                 330                 335

Lys Leu Val Glu Thr Val Arg Gly Ala Ala Glu Lys Leu Gly Tyr Ser
            340                 345                 350

His Met Asn Leu Val Ser Gly Ala Gly His Asp Ala Cys Trp Ala Ala
        355                 360                 365

Lys Val Ala Pro Thr Thr Met Ile Met Cys Pro Cys Val Gly Gly Leu
    370                 375                 380

Ser His Asn Glu Ala Glu Asp Ile Ser Arg Glu Trp Ala Ala Ala Gly
385                 390                 395                 400

Ala Asp Val Leu Phe His Ala Val Leu Glu Thr Ala Glu Ile Val Glu
                405                 410                 415

<210> SEQ ID NO 7
<211> LENGTH: 413
<212> TYPE: PRT
<213> ORGANISM: Bacillus fordii
<220> FEATURE:
<221> NAME/KEY: misc_feature
<222> LOCATION: 1..413
<223> OTHER INFORMATION: Bacillus fordii MH602 (strain)

<400> SEQUENCE: 7

Met Glu Lys Gln Lys Val Leu Ile Asn Gly Glu Arg Leu Lys Asp Thr
1               5                   10                  15

Ile Glu Glu Phe Ala Asp Phe Gly Arg Thr Glu Lys Asn Gly Val Thr
                20                  25                  30

Arg Leu Ala Leu Ser Asp Val Asp Val Lys Ala Arg Arg His Phe Gln
            35                  40                  45

Ser Leu Cys Glu Gln Leu Gly Met Ser Val Val Trp Asp Asp Met Gly
```

```
            50                  55                  60
Asn Met Tyr Ala Lys Leu Pro Gly Ile Asp Asn Asp Gln Pro Pro Val
 65                  70                  75                  80

Val Ile Gly Ser His Leu Asp Ser Val Lys Lys Gly Arg Phe Asp
                 85                  90                  95

Gly Thr Leu Gly Val Leu Thr Gly Leu Glu Val Val Arg Thr Met Val
                100                 105                 110

Glu Asn Gly Ile Lys Pro Glu Ile Pro Ile Val Ala Asn Ile Thr
                115                 120                 125

Asn Glu Glu Gly Ala Arg Phe Glu Pro Ser Leu Met Ala Ser Gly Val
                130                 135                 140

Leu Ser Gly Arg Phe Asp Lys Ala Ala Met Leu Lys Ser Thr Asp Val
145                 150                 155                 160

Asp Gly Ile Thr Phe Ala Glu Ala Leu Lys Lys Ser Gly Tyr Glu Gly
                165                 170                 175

Lys Lys Glu Asn Arg Leu Lys Glu Ala Ala Phe Leu Glu Leu His
                180                 185                 190

Ile Glu Gln Gly Pro Val Leu Glu Ser Glu Asp Ile Gln Ile Gly Ile
                195                 200                 205

Val Glu Cys Val Val Gly Met Val Cys Phe Glu Ile Glu Val Thr Gly
210                 215                 220

Glu Ser Asp His Ala Gly Thr Thr Pro Met Ser Met Arg Lys Asp Ala
225                 230                 235                 240

Leu Phe Ala Ala Asn Gln Leu Ile Ser Glu Ile Arg Gln Lys Met Asn
                245                 250                 255

Arg Leu Asp Asp Gln Leu Val Tyr Thr Val Gly Arg Met Thr Val Ser
                260                 265                 270

Pro Asn Ile His Thr Val Ile Pro Asn Lys Val Val Phe Thr Ile Gly
                275                 280                 285

Ala Arg His Gln Asp Gly Lys Ile Ile Arg Gln Val Glu Glu Ile Ile
                290                 295                 300

Gln Gly Leu Pro Asn Ser Ser Gly Lys Glu Lys Cys Asn Val Thr Thr
305                 310                 315                 320

Thr Lys Leu Trp Asp Arg His Thr Val Trp Phe Asn Glu Glu Ile Val
                325                 330                 335

Asn Thr Leu Glu Lys Ser Ala Arg Ser Leu Gly Tyr Ser Phe Lys Arg
                340                 345                 350

Met Val Ser Gly Ala Gly His Asp Ala Gln Phe Ile Ala Thr Tyr Ile
                355                 360                 365

Pro Thr Ala Met Val Phe Val Pro Ser Ile Asn Gly Lys Ser His Asp
                370                 375                 380

Glu Asp Glu Leu Thr Thr Trp Glu Asp Cys Glu Asn Gly Val Asn Val
385                 390                 395                 400

Ile Leu Gln Thr Val Leu Asp Leu Thr Thr Asp Lys Leu
                405                 410

<210> SEQ ID NO 8
<211> LENGTH: 412
<212> TYPE: PRT
<213> ORGANISM: Arthrobacter sp.
<220> FEATURE:
<221> NAME/KEY: misc_feature
<222> LOCATION: 1..412
<223> OTHER INFORMATION: Arthrobacter sp. BT801 (strain)
<220> FEATURE:
<221> NAME/KEY: gene
```

<222> LOCATION: 1..412
<223> OTHER INFORMATION: HyuC

<400> SEQUENCE: 8

Met Thr Ser Leu Arg Ala Gln Ala Asp Arg Ile Glu Lys Asp Ile Arg
1               5                   10                  15

Asp Leu Ala Arg Phe Ser Ala Gly Gly Pro Gly Val Thr Arg Leu Ser
            20                  25                  30

Tyr Thr Pro Glu His Ala Ala Arg Asp Leu Ile Ile Ala Ala Met
        35                  40                  45

Gln Gln Ala Gly Leu Asp Val Arg Glu Asp Gly Leu Gly Asn Ile Thr
    50                  55                  60

Gly Arg Arg Glu Gly Ser Asp Pro Asp Leu Pro Ala Ile Ala Val Gly
65                  70                  75                  80

Ser His Phe Asp Ser Val Arg Asn Gly Gly Met Phe Asp Gly Thr Ala
                85                  90                  95

Gly Val Val Cys Ala Leu Glu Ala Ala Arg Val Val Asn Glu Ser Glu
            100                 105                 110

Tyr Val Asn Arg His Pro Phe Glu Phe Ile Ala Ile Val Glu Glu Glu
        115                 120                 125

Gly Ser Arg Phe Asn Ser Gly Met Leu Gly Gly Arg Ala Leu Ala Gly
    130                 135                 140

Leu Val Thr Asp Glu Asp Leu Asp Lys Leu Lys Asp Glu Asp Gly Ile
145                 150                 155                 160

Ser Val Arg Asp Ala Ala Thr Glu Phe Gly Leu Gln Pro Gly Asn Leu
                165                 170                 175

Gln Thr Ser Val Arg Ser Arg Leu Asp Leu Arg Ala Phe Ile Glu Pro
            180                 185                 190

His Ile Glu Gln Gly Pro Val Leu Glu Gln Gly Ile Glu Ile Gly
        195                 200                 205

Val Val Thr Ser Ile Val Gly Ile Arg Thr Leu Arg Val Ala Val Leu
    210                 215                 220

Gly Arg Ser Asp His Ala Gly Thr Thr Pro Met His Leu Arg Gln Asp
225                 230                 235                 240

Ala Leu Ile Pro Ser Ala Leu Met Val Arg Glu Val Asn Arg Leu Val
                245                 250                 255

Asn Glu Leu Gly Asp Glu Thr Val Ala Thr Val Gly His Leu Thr Val
            260                 265                 270

Ala Pro Gly Gly Ile Asn Gln Val Pro Gly Glu Val Asn Phe Thr Leu
        275                 280                 285

Asp Leu Arg Ser Pro His Glu Glu Ser Leu Lys Gln Ile Val Lys Gln
    290                 295                 300

Ile Thr Val Met Ile Gln Glu Val Ala Ser Gln Ala Glu Val Thr Ala
305                 310                 315                 320

Asn Val Glu Glu Phe Phe Ser Leu Asp Pro Val Pro Leu Ala Pro Ser
                325                 330                 335

Val Val Asp Ala Val Arg Gln Ala Ala Ser Asn Leu Arg Phe Ser His
            340                 345                 350

Arg Asp Met Pro Ser Gly Ala Gly His Asp Ser Met Phe Ile Ser Gln
        355                 360                 365

Val Thr Asp Val Gly Met Val Phe Val Pro Ser Arg Asp Gly Arg Ser
    370                 375                 380

His Val Pro Glu Glu Trp Ser Asp Phe Asp Asp Leu Arg Lys Gly Thr
385                 390                 395                 400

Asp Val Val Leu Gly Val Met Thr Ala Leu Asp Lys
            405                 410

<210> SEQ ID NO 9
<211> LENGTH: 412
<212> TYPE: PRT
<213> ORGANISM: Microbacterium liquefaciens
<220> FEATURE:
<221> NAME/KEY: misc_feature
<222> LOCATION: 1..412
<223> OTHER INFORMATION: Microbacterium liquefaciens AJ 3912 (strain)

<400> SEQUENCE: 9

Met Thr Leu Gln Gln Ala Arg Ala Asp Arg Ile Glu Glu Glu Leu Trp
1               5                   10                  15

Thr Leu Ser Arg Phe Ser Val Glu Gly Pro Gly Val Thr Arg Leu Thr
            20                  25                  30

Tyr Thr Pro Glu His Ala Ala Arg Glu Val Ile Val Ala Ala Met
        35                  40                  45

Gln Arg Thr Gly Leu Ser Val His Glu Asp Ala Leu Gly Asn Ile Ile
    50                  55                  60

Gly Arg Arg Glu Gly Ser Asp Pro Ala Leu Pro Ala Ile Ala Phe Gly
65                  70                  75                  80

Ser His Phe Asp Ser Val Arg Asn Gly Gly Met Phe Asp Gly Thr Ala
                85                  90                  95

Gly Val Val Cys Ala Leu Glu Ala Ala Arg Val Leu Gln Glu Ser Gly
            100                 105                 110

Tyr Val Asn Arg His Pro Leu Glu Val Ile Ala Ile Val Glu Glu Glu
        115                 120                 125

Gly Thr Arg Phe Ser Ser Gly Met Leu Gly Gly Arg Ala Ile Ala Gly
    130                 135                 140

Leu Val Ser Asp Ala Asp Leu Asp Thr Leu Val Asp Glu Asp Gly Val
145                 150                 155                 160

Thr Val Arg Glu Ala Ala Thr Ala Phe Gly Leu Glu Pro Gly Glu Leu
                165                 170                 175

Arg Thr Ala Ala Arg Thr Arg Asp Asp Leu Arg Ala Phe Ile Glu Leu
            180                 185                 190

His Ile Glu Gln Gly Pro Ile Leu Glu Gln Glu Lys Val Glu Ile Gly
        195                 200                 205

Val Val Thr Gly Ile Val Gly Val Arg Ala Phe Arg Ile Thr Val Glu
    210                 215                 220

Gly Arg Ser Asp His Ala Gly Thr Thr Pro Met His Leu Arg Gln Asp
225                 230                 235                 240

Ala Leu Val Pro Ala Ala Leu Met Val Arg Glu Ile Asn Arg Phe Val
                245                 250                 255

Asn Glu Ile Ala Asp Gly Thr Val Ala Thr Val Gly His Leu Thr Val
            260                 265                 270

Thr Pro Gly Gly Leu Asn Gln Val Pro Gly Gly Val Glu Phe Thr Leu
        275                 280                 285

Asp Leu Arg Ser Pro His Glu Glu Ser Ile Arg Leu Leu Val Asp Arg
    290                 295                 300

Ile Glu Ala Met Val Ala Glu Val Ala Ala Ala Gly Val Glu Ala
305                 310                 315                 320

Ala Val Asn Gly Phe Phe Ala Leu Ser Pro Val Gly Leu Ser Pro Val
                325                 330                 335

Val Val Asp Arg Val Arg Asp Ala Ala Ser Glu Leu Gly Phe Thr His
            340                 345                 350

Arg Asp Ile Thr Ser Gly Ala Gly His Asp Ser Met Phe Ile Ala Gln
            355                 360                 365

Ile Thr Asp Val Gly Met Val Phe Val Pro Ser Arg Ala Gly Arg Ser
370                 375                 380

His Val Pro Glu Glu Trp Ser Asp Phe Asp Asp Leu Arg Lys Gly Thr
385                 390                 395                 400

Asp Val Val Leu His Val Thr Ala Leu Asp Arg
                405                 410

<210> SEQ ID NO 10
<211> LENGTH: 420
<212> TYPE: PRT
<213> ORGANISM: Arthrobacter sp.
<220> FEATURE:
<221> NAME/KEY: misc_feature
<222> LOCATION: 1..420
<223> OTHER INFORMATION: Arthrobacter sp. DSM 9771 (strain)
<220> FEATURE:
<221> NAME/KEY: gene
<222> LOCATION: 1..420
<223> OTHER INFORMATION: HyuH

<400> SEQUENCE: 10

Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
            20                  25                  30

Ser Ser Asp Thr Ser Asp Val Glu Ala Ser Arg Thr Ile Asp Ala Gly
        35                  40                  45

Gly Lys Phe Val Met Pro Gly Val Val Asp Glu His Val His Ile Ile
    50                  55                  60

Asp Met Asp Leu Lys Asn Arg Tyr Gly Arg Phe Glu Leu Asp Ser Glu
65                  70                  75                  80

Ser Ala Ala Val Gly Gly Ile Thr Thr Ile Phe Glu Met Pro Phe Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Ala Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Ala Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Glu Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Arg Ala Gln Ser Glu Gly
                245                 250                 255

```
Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
        275                 280                 285

Arg Ser Ala Glu Met Asn Val Arg Leu Trp Glu Gln Leu Glu Asn Gly
    290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
        355                 360                 365

Ala Lys Leu Phe Gly Ile Tyr Pro Gln Lys Gly Thr Leu Gln Val Gly
    370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr
            420

<210> SEQ ID NO 11
<211> LENGTH: 479
<212> TYPE: PRT
<213> ORGANISM: Pseudomonas fluorescens

<400> SEQUENCE: 11

Met Ser Leu Leu Ile Arg Gly Ala Thr Val Ile Thr Tyr Asp Glu Arg
1               5                   10                  15

Tyr Arg Ala Asp Val Leu Cys Ala Gly Gly Leu Ile Arg Ala Ile Gly
            20                  25                  30

Thr Gly Leu Asp Val Pro Ala Gly Thr Glu Val Leu Asp Gly Ser Gly
        35                  40                  45

Gln Tyr Leu Met Pro Gly Gly Ile Asp Pro His Thr His Met Gln Leu
    50                  55                  60

Pro Phe Met Gly Thr Val Ala Ser Glu Asp Phe Phe Ser Gly Thr Ala
65                  70                  75                  80

Ala Gly Leu Ala Gly Gly Thr Thr Ser Ile Ile Asp Phe Val Ile Pro
                85                  90                  95

Asn Pro Gln Gln Ser Leu Met Glu Ala Phe His Gln Trp Arg Gly Trp
            100                 105                 110

Ala Glu Lys Ser Ala Ser Asp Tyr Gly Phe His Val Ala Ile Thr Trp
        115                 120                 125

Trp Ser Glu Gln Val Arg Glu Glu Met Ala Glu Leu Val Ser His His
    130                 135                 140

Gly Ile Asn Ser Phe Lys His Phe Met Ala Tyr Lys Asn Ala Ile Met
145                 150                 155                 160

Ala Ala Asp Asp Thr Leu Val Ala Ser Phe Glu Arg Cys Leu Glu Leu
                165                 170                 175

Gly Ala Val Pro Thr Val His Ala Glu Asn Gly Glu Leu Val Tyr His
            180                 185                 190

Leu Gln Arg Lys Leu Met Ala Gln Gly Ile Thr Gly Pro Glu Ala His
        195                 200                 205
```

-continued

Pro Leu Ser Arg Pro Ser Gln Val Glu Gly Glu Ala Ala Ser Arg Ala
    210                 215                 220

Ile Arg Ile Ala Glu Thr Ile Gly Thr Pro Leu Tyr Leu Val His Val
225                 230                 235                 240

Ser Thr Lys Glu Ala Leu Asp Glu Ile Thr Tyr Ala Arg Gly Lys Gly
                245                 250                 255

Gln Pro Val Tyr Gly Glu Val Leu Ala Gly His Leu Leu Asp Asp
                260                 265                 270

Ser Val Tyr Gln His Pro Asp Trp His Thr Ala Ala Gly Tyr Val Met
            275                 280                 285

Ser Pro Pro Phe Arg Pro Arg Gly His Gln Glu Ala Leu Trp His Gly
    290                 295                 300

Leu Gln Ser Gly Asn Leu His Thr Thr Ala Thr Asp His Cys Cys Phe
305                 310                 315                 320

Cys Ala Glu Gln Lys Ala Ala Gly Arg Asp Asp Phe Ser Lys Ile Pro
                325                 330                 335

Asn Gly Thr Ala Gly Ile Glu Asp Arg Met Ala Leu Leu Trp His Glu
            340                 345                 350

Gly Val Asn Thr Gly Arg Leu Ser Met Gln Glu Phe Val Ala Leu Thr
        355                 360                 365

Ser Thr Asn Thr Ala Lys Ile Phe Asn Leu Tyr Pro Arg Lys Gly Ala
370                 375                 380

Ile Arg Val Gly Ala Asp Ala Asp Leu Val Leu Trp Asp Pro Glu Gly
385                 390                 395                 400

Thr Arg Thr Ile Ser Ala Lys Thr His His Gln Lys Val Asp Phe Asn
                405                 410                 415

Ile Phe Glu Gly Lys Thr Val Arg Gly Val Pro Ser His Thr Ile Ser
            420                 425                 430

Gln Gly Lys Leu Val Trp Ala Asp Gly Asp Leu Arg Ala Glu Arg Gly
        435                 440                 445

Ala Gly Arg Tyr Val Glu Arg Pro Ala Tyr Pro Ser Val Phe Glu Gln
    450                 455                 460

Leu Ser Lys Arg Ala Glu His Ser Arg Pro Thr Ala Val Lys Arg
465                 470                 475

<210> SEQ ID NO 12
<211> LENGTH: 479
<212> TYPE: PRT
<213> ORGANISM: Pseudomonas aeruginosa
<220> FEATURE:
<221> NAME/KEY: gene
<222> LOCATION: 1..479
<223> OTHER INFORMATION: Dht

<400> SEQUENCE: 12

Met Ser Leu Leu Ile Arg Gly Ala Thr Val Val Thr His Glu Glu Ser
1               5                   10                  15

Tyr Arg Ala Asp Val Leu Cys Ala Asn Gly Leu Ile Gln Ala Ile Gly
                20                  25                  30

Glu Asn Leu Glu Thr Pro Ser Gly Cys Asp Val Leu Asp Gly Gly Gly
            35                  40                  45

Gln Tyr Leu Met Pro Gly Gly Ile Asp Pro His Thr His Met Gln Leu
        50                  55                  60

Pro Phe Met Gly Thr Val Ala Ser Glu Asp Phe Phe Ser Gly Thr Ala
65                  70                  75                  80

```
Ala Gly Leu Ala Gly Gly Thr Thr Ser Ile Ile Asp Phe Val Ile Pro
             85                  90                  95
Asn Pro Arg Gln Ser Leu Leu Glu Ala Phe His Thr Trp Arg Gly Trp
            100                 105                 110
Ala Gln Lys Ser Ala Ala Asp Tyr Gly Phe His Val Ala Ile Thr Trp
            115                 120                 125
Trp Ser Asp Glu Val Ala Arg Glu Met Gly Glu Leu Val Ala Gln His
    130                 135                 140
Gly Val Asn Ser Phe Lys His Phe Met Ala Tyr Lys Asn Ala Ile Met
145                 150                 155                 160
Ala Ala Asp Asp Thr Leu Val Ala Ser Phe Glu Arg Cys Leu Glu Leu
                165                 170                 175
Gly Ala Val Pro Thr Val His Ala Glu Asn Gly Glu Leu Val Phe His
            180                 185                 190
Leu Gln Gln Lys Leu Leu Ala Gln Gly Leu Thr Gly Pro Glu Ala His
            195                 200                 205
Pro Leu Ser Arg Pro Pro Gln Val Glu Gly Ala Ala Ser Arg Ala
    210                 215                 220
Ile Arg Ile Ala Glu Thr Leu Gly Thr Pro Leu Tyr Leu Val His Ile
225                 230                 235                 240
Ser Ser Arg Glu Ala Leu Asp Glu Ile Ala Tyr Ala Arg Ala Lys Gly
                245                 250                 255
Gln Pro Val Tyr Gly Glu Val Leu Ala Gly His Leu Leu Leu Asp Asp
            260                 265                 270
Ser Val Tyr Arg His Pro Asp Trp Ala Thr Ala Ala Gly Tyr Val Met
    275                 280                 285
Ser Pro Pro Phe Arg Pro Val Glu His Gln Glu Ala Leu Trp Arg Gly
290                 295                 300
Leu Gln Ser Gly Asn Leu His Thr Thr Ala Thr Asp His Cys Cys Phe
305                 310                 315                 320
Cys Ala Glu Gln Lys Ala Met Gly Arg Asp Asp Phe Ser Lys Ile Pro
                325                 330                 335
Asn Gly Thr Ala Gly Ile Glu Asp Arg Met Ala Leu Leu Trp Asp Ala
            340                 345                 350
Gly Val Asn Ser Gly Arg Leu Ser Met His Glu Phe Val Ala Leu Thr
            355                 360                 365
Ser Thr Asn Thr Ala Lys Ile Phe Asn Leu Phe Pro Arg Lys Gly Ala
    370                 375                 380
Ile Arg Val Gly Ala Asp Ala Asp Leu Val Leu Trp Asp Pro Gln Gly
385                 390                 395                 400
Ser Arg Thr Leu Ser Ala Ala Thr His His Gln Arg Val Asp Phe Asn
                405                 410                 415
Ile Phe Glu Gly Arg Thr Val Arg Gly Ile Pro Ser His Thr Ile Ser
            420                 425                 430
Gln Gly Lys Leu Leu Trp Ala Ala Gly Asp Leu Arg Ala Glu Pro Gly
            435                 440                 445
Ala Gly Arg Tyr Val Glu Arg Pro Ala Tyr Pro Ser Val Tyr Glu Val
    450                 455                 460
Leu Gly Arg Arg Ala Glu Arg Gln Arg Pro Val Ala Val Glu Arg
465                 470                 475
```

<210> SEQ ID NO 13
<211> LENGTH: 475
<212> TYPE: PRT

```
<213> ORGANISM: Bacillus fordii
<220> FEATURE:
<221> NAME/KEY: misc_feature
<222> LOCATION: 1..475
<223> OTHER INFORMATION: Bacillus fordii MH602 (strain)

<400> SEQUENCE: 13
```

| | | | | | | | | | | | | | | |
|---|---|---|---|---|---|---|---|---|---|---|---|---|---|---|
| Met | Lys | Lys | Ile | Ile | Lys | Asp | Gly | Thr | Val | Thr | Ser | Thr | Asp | Val |
| 1 | | | | 5 | | | | | 10 | | | | | 15 |
| Tyr | Thr | Ala | Asp | Val | Leu | Ile | Glu | Asp | Glu | Lys | Ile | Gln | Ala | Ile | Gly |
| | | | 20 | | | | | 25 | | | | | 30 | | |
| Gln | Asn | Ile | Ser | Asp | Ile | Tyr | Ala | Glu | Val | Ile | Asp | Ala | Ser | Gly | Tyr |
| | | | 35 | | | | | 40 | | | | | 45 | | |
| Tyr | Val | Met | Pro | Gly | Gly | Ile | Asp | Pro | His | Thr | His | Met | Asp | Met | Pro |
| 50 | | | | | 55 | | | | | 60 | | | | | |
| Phe | Gly | Gly | Thr | Val | Thr | Ala | Asp | Phe | Glu | Thr | Gly | Ser | Ile | Ala |
| 65 | | | | 70 | | | | | 75 | | | | | 80 |
| Ala | Ala | Cys | Gly | Gly | Thr | Thr | Thr | Ile | Ile | Asp | Phe | Cys | Leu | Thr | Gly |
| | | | 85 | | | | | 90 | | | | | 95 | | |
| Lys | Gly | Lys | Ser | Leu | Lys | Ser | Ala | Leu | Glu | Lys | Trp | His | Ala | Lys | Ser |
| | | | 100 | | | | | 105 | | | | | 110 | | |
| Ala | Gly | Lys | Ala | Val | Ile | Asp | Tyr | Gly | Phe | His | Leu | Gln | Ile | Ala | Glu |
| | | | 115 | | | | | 120 | | | | | 125 | | |
| Ala | Asn | Glu | Glu | Val | Phe | Met | Glu | Met | Pro | Gln | Ile | Ile | Glu | Glu |
| | | 130 | | | | | 135 | | | | | 140 | | |
| Gly | Val | Thr | Ser | Phe | Lys | Ile | Phe | Met | Ala | Tyr | Lys | Asp | Val | Leu | Gln |
| 145 | | | | | 150 | | | | | 155 | | | | | 160 |
| Ala | Asp | Asp | Glu | Thr | Leu | Phe | Gln | Thr | Leu | Val | Thr | Ala | Arg | Glu | His |
| | | | 165 | | | | | 170 | | | | | 175 | | |
| Gly | Gly | Leu | Val | Met | Val | His | Ala | Glu | Asn | Gly | Asp | Val | Ile | Asn | Tyr |
| | | | 180 | | | | | 185 | | | | | 190 | | |
| Leu | Thr | Glu | Lys | Ala | Leu | Lys | Glu | Gly | Asn | Thr | Glu | Pro | Ile | Tyr | His |
| | | | 195 | | | | | 200 | | | | | 205 | | |
| Ala | Leu | Thr | Arg | Pro | Pro | Glu | Leu | Glu | Gly | Glu | Ala | Thr | Gly | Arg | Ala |
| | | 210 | | | | | 215 | | | | | 220 | | |
| Ala | Arg | Leu | Thr | Ala | Leu | Ala | Asp | Ser | Gln | Leu | Tyr | Val | His | Val |
| 225 | | | | | 230 | | | | | 235 | | | | | 240 |
| Thr | Cys | Lys | Glu | Ala | Val | Glu | Gln | Ile | Ala | Glu | Ala | Arg | Arg | Gly |
| | | | 245 | | | | | 250 | | | | | 255 | |
| Tyr | Arg | Val | Phe | Gly | Glu | Thr | Cys | Pro | Gln | Tyr | Leu | Val | Leu | Asp | Gln |
| | | | 260 | | | | | 265 | | | | | 270 | | |
| Thr | Tyr | Leu | Glu | Arg | Pro | Asp | Phe | Glu | Gly | Ala | Lys | Tyr | Val | Trp | Ser |
| | | | 275 | | | | | 280 | | | | | 285 | | |
| Pro | Pro | Leu | Arg | Glu | Arg | Ser | Asn | Gln | Glu | Val | Leu | Trp | Asn | Ala | Leu |
| | | | 290 | | | | | 295 | | | | | 300 | | |
| Lys | Ser | Gly | Asp | Leu | Gln | Ala | Ile | Gly | Ser | Asp | His | Cys | Ser | Phe | Asn |
| 305 | | | | | 310 | | | | | 315 | | | | | 320 |
| Phe | Arg | Gly | Gln | Lys | Glu | Leu | Gly | Lys | Asn | Asp | Phe | Ser | Lys | Ile | Pro |
| | | | 325 | | | | | 330 | | | | | 335 | | |
| Asn | Gly | Gly | Pro | Phe | Val | Glu | Asp | Arg | Phe | Ser | Val | Leu | Phe | Ser | Glu |
| | | | 340 | | | | | 345 | | | | | 350 | | |
| Gly | Val | Lys | Lys | Gly | Arg | Ile | Ser | Ile | His | Asp | Phe | Val | Asn | Ile | Ile |
| | | | 355 | | | | | 360 | | | | | 365 | | |
| Ser | Thr | Gln | Ala | Ala | Lys | Leu | Phe | Gly | Leu | Phe | Pro | Arg | Lys | Gly | Thr |
| | | 370 | | | | | 375 | | | | | 380 | | |

```
Ile Ala Pro Gly Ser Asp Ala Asp Ile Val Ile Phe Asp Pro Asn Val
385                 390                 395                 400

Glu Arg Ile Ile Ser Val Glu Thr His His Met Asn Val Asp Tyr Ser
            405                 410                 415

Ala Leu Glu Gly Leu Lys Ile Ile Gly Glu Pro Ile Thr Val Leu Ser
            420                 425                 430

Arg Gly Asn Tyr Val Val Lys Asp Lys Glu Phe Val Gly Lys Pro Gly
            435                 440                 445

Lys Gly Lys Phe Leu Lys Cys Asn Lys Phe Asn His Asp Leu Tyr Lys
450                 455                 460

Glu Thr Gly Gln Leu Gly Leu Leu Lys Gly
465                 470                 475

<210> SEQ ID NO 14
<211> LENGTH: 458
<212> TYPE: PRT
<213> ORGANISM: Arthrobacter sp.
<220> FEATURE:
<221> NAME/KEY: misc_feature
<222> LOCATION: 1..458
<223> OTHER INFORMATION: Arthrobacter sp. BT801 (strain)
<220> FEATURE:
<221> NAME/KEY: gene
<222> LOCATION: 1..458
<223> OTHER INFORMATION: HyuH

<400> SEQUENCE: 14

Met Phe Asp Val Ile Val Lys Asn Cys Arg Ile Val Ser Ser Glu Gly
1               5                   10                  15

Ile Thr Glu Ala Asp Ile Leu Val Lys Glu Gly Lys Val Ala Ala Ile
            20                  25                  30

Ser Ser Glu Gly Leu Asn Asp Glu Val Gln Glu Thr Ile Asp Ala Gly
            35                  40                  45

Gly Lys Phe Val Leu Pro Gly Val Val Asp Glu His Val His Ile Ile
        50                  55                  60

Asp Met Asp Leu Lys Asp Gln Asn Gly Arg Phe Glu Phe Asp Ser Glu
65                  70                  75                  80

Ser Ala Ala Val Gly Gly Ile Thr Thr Ile Ile Glu Met Pro Ile Thr
                85                  90                  95

Ser Pro Pro Thr Thr Thr Leu Glu Ala Phe Leu Ala Lys Lys Lys Glu
            100                 105                 110

Ala Gly Asp Arg Leu Lys Val Asp Phe Ala Leu Tyr Gly Gly Gly Val
            115                 120                 125

Pro Gly Asn Leu Ser Glu Ile Arg Lys Met His Glu Ala Gly Ala Val
        130                 135                 140

Gly Phe Lys Ser Met Met Ala Ala Ser Val Pro Gly Met Phe Glu Ala
145                 150                 155                 160

Val Thr Asp Gly Glu Leu Phe Glu Ile Phe Gln Glu Ile Ala Thr Cys
                165                 170                 175

Gly Ser Val Ile Val Val His Ala Glu Asn Glu Thr Ile Ile Gln Ser
            180                 185                 190

Leu Gln Arg Gln Leu Lys Glu Ala Gly Arg Thr Asp Met Ala Ala Tyr
            195                 200                 205

Glu Ala Ser Gln Pro Ala Phe Gln Asn Glu Ala Ile Gln Arg Ala
        210                 215                 220

Leu Ala Leu Gln Lys Glu Thr Gly Cys Arg Leu Ile Val Leu His Val
225                 230                 235                 240
```

Ser Asn Pro Asp Gly Val Gln Leu Ile His Gln Ala Gln Ser Ser Gly
            245                 250                 255

Gln Asp Val His Cys Glu Ser Gly Pro Gln Tyr Leu Asn Ile Thr Ala
            260                 265                 270

Glu Asp Ala Ser Arg Ile Gly Pro Tyr Met Lys Ile Ala Pro Pro Val
            275                 280                 285

Arg Ser Ala Glu Met Asn Ala Arg Leu Trp Glu Gln Leu Glu Lys Gly
            290                 295                 300

Leu Ile Asp Thr Leu Gly Ser Asp His Gly Gly His Pro Lys Glu Asn
305                 310                 315                 320

Lys Glu Arg Gly Trp Asp Asn Val Trp Asp Ala Ser Asn Gly Ala Leu
                325                 330                 335

Gly Leu Glu Thr Ser Leu Pro Met Met Leu Thr Asn Gly Val Asn Arg
            340                 345                 350

Gly Arg Leu Ser Leu Glu Arg Leu Val Glu Val Met Cys Glu Asn Pro
            355                 360                 365

Ala Lys Leu Phe Gly Ile Tyr Pro Gln Lys Gly Thr Leu Gln Val Gly
            370                 375                 380

Ser Asp Ala Asp Leu Val Ile Val Asp Leu Glu Val Asp Asp Lys Val
385                 390                 395                 400

Asp Ala Ser Glu Phe Arg Ser Leu Leu Lys His Ser Pro Phe Asp Gly
                405                 410                 415

Met Pro Val Thr Gly Lys Pro Val Leu Thr Met Val Arg Gly Thr Val
            420                 425                 430

Val Ala Glu Asn Gly Lys Ile Leu Val Glu Pro Gly Phe Gly Gln Phe
            435                 440                 445

Val Thr Cys Arg Glu Ser Gln Asp Pro Lys
            450                 455

<210> SEQ ID NO 15
<211> LENGTH: 455
<212> TYPE: PRT
<213> ORGANISM: Alcaligenes faecalis
<220> FEATURE:
<221> NAME/KEY: misc_feature
<222> LOCATION: 1..455
<223> OTHER INFORMATION: Alcaligenes faecalis subsp. faecalis
      (subspecies)

<400> SEQUENCE: 15

Met Ser Asp Phe Asp Leu Val Val Arg Gly Asn Ile Val Glu Arg Asp
1               5                   10                  15

Arg Ile Ile Thr Asp Gly Trp Val Ala Val Arg Glu Gly Arg Val Ala
            20                  25                  30

Ala Arg Gly Ile Gly Ala Ala Pro Ser Ala Arg Glu His Val Asp Ala
            35                  40                  45

Arg Gly Met Trp Val Met Pro Gly Val Leu Asp Gly Gln Val His Ser
            50                  55                  60

Gly Ser Gln Ala Asn Gln Glu Gly Leu Gly Trp Ala Ser Arg Ala Ala
65                  70                  75                  80

Ala Ala Gly Gly Val Thr Thr Met Val Glu Met Pro His Asp Asp Pro
                85                  90                  95

Glu Pro Val Ala Ser Arg Ala Gln Leu Glu Asp Lys Ile Ala Arg Ile
            100                 105                 110

Glu Ser Asp Cys His Val Asp Val Ala Cys Tyr Gly Thr Leu Asn Asp
            115                 120                 125

Gln His Gly Leu Glu Ala Ala Gly Leu Ile Glu Gly Gly Val Cys
    130                 135                 140

Gly Phe Lys Phe Ser Thr Phe Glu Ala Ser Pro Asn Arg Ser Pro Arg
145                 150                 155                 160

Val Glu Glu Asp Ile Leu Met Glu Ala Phe Arg Leu Ile Ala Pro Ser
                165                 170                 175

Gly Leu Ala Cys Gly Val His Asn Gln Asp Gln Glu Leu Thr Arg Lys
            180                 185                 190

Asn Ile Lys Arg Met Val Glu Ala Gly Asp Thr Gly Trp Asp Ala Phe
        195                 200                 205

Leu Arg Ala His Thr Pro Leu Ile Glu Asn Leu Ala Thr Ser Ala Ile
    210                 215                 220

Tyr Glu Ile Gly Ala Gln Thr Gly Ala Arg Ala His Ala Val His Val
225                 230                 235                 240

Ser Leu Ser Arg Gly Phe Glu Ile Cys Asn Met Tyr Arg Arg Ala Gly
                245                 250                 255

Tyr Lys Ala Ser Ile Glu Thr Cys Val Gln Tyr Leu Met Leu Asn His
            260                 265                 270

Glu Glu His Thr Arg Arg Phe Gly Ala Lys Thr Lys His Tyr Pro Pro
        275                 280                 285

Ile Arg Pro Lys Ala Glu Met Asp Leu Leu Trp Thr His Ile Ala Asn
    290                 295                 300

Asp Glu Cys Thr Phe Val Ser Ser Asp His Val Ser Trp Gly Leu Glu
305                 310                 315                 320

Arg Lys Gln Phe Glu Asn Val Phe Gln Asn Ser Ser Gly Gly Pro Gly
                325                 330                 335

Leu Glu Thr Leu Leu Pro Ala Phe Trp Thr Gly Cys Ala Glu His Gly
            340                 345                 350

Ile Ser Pro Thr Met Val Val Lys Gln Leu Cys Trp Gly Pro Ala Gln
        355                 360                 365

His Phe Leu Leu Glu His Arg Lys Gly Ser Leu Asn Val Gly Ala Asp
    370                 375                 380

Ala Asp Ile Val Ile Val Lys Pro Asp Thr Tyr Arg Phe Asp Pro Ser
385                 390                 395                 400

Thr Ser Leu Ser Ala Val Thr Trp Ser Ser Phe Glu Asp Arg Glu Leu
                405                 410                 415

Gln Val Arg Val Glu Ala Thr Tyr Val Arg Gly Gln Leu Ala Trp Asp
            420                 425                 430

Gly Lys Thr Ile Arg Asn Ala Ala Gly Asp Gly Gln Phe Ile Arg Pro
        435                 440                 445

His Lys Ala Gly Glu Leu Ser
    450                 455

<210> SEQ ID NO 16
<211> LENGTH: 459
<212> TYPE: PRT
<213> ORGANISM: Microbacterium liquefaciens
<220> FEATURE:
<221> NAME/KEY: misc_feature
<222> LOCATION: 1..459
<223> OTHER INFORMATION: Microbacterium liquefaciens AJ 3912 (strain)

<400> SEQUENCE: 16

Met Phe Asp Val Ile Val Lys Asn Cys Arg Val Val Ser Ser Gln Gly
1               5                   10                  15

```
Ile Ile Glu Ala Asp Ile Leu Val Lys Asp Gly Arg Ile Ala Ala Ile
            20                  25                  30

Ser Glu Glu Pro Leu Glu Ala Glu Ala Arg Thr Ile Asp Ala Ala
        35                  40                  45

Gly Arg Phe Val Met Pro Gly Val Val Asp Glu His Val His Ile Ile
    50                  55                  60

Asp Met Asp Leu Lys Glu Val Tyr Gly Arg Phe Glu Leu Asp Ser Glu
65                  70                  75                  80

Ser Ala Ala Val Gly Val Thr Thr Ile Ile Glu Met Pro Ile Thr
                85                  90                  95

Phe Pro Pro Thr Thr Thr Leu Glu Ala Phe Leu Glu Lys Lys Lys Gln
            100                 105                 110

Gly Glu Gln Arg Leu Lys Val Asp Phe Ala Leu Tyr Gly Gly Gly Val
        115                 120                 125

Pro Gly Asn Leu Ser Glu Ile Arg Lys Met His Asp Ala Gly Ala Val
    130                 135                 140

Gly Phe Lys Ser Met Met Ala Ala Ser Val Pro Gly Met Phe Glu Ala
145                 150                 155                 160

Val Asp Asp Gly Gln Leu Phe Glu Ile Phe Gln Glu Ile Ala Ala Cys
            165                 170                 175

Gly Ser Val Ile Val Val His Ala Glu Asn Glu Met Leu Ile Gln Thr
        180                 185                 190

Leu Gln Lys Gln Leu Lys Ala Ala Gly Arg Lys Asp Leu Ala Ala Tyr
    195                 200                 205

Glu Ala Ser Gln Pro Val Phe Gln Glu Asn Glu Ala Ile Gln Arg Ala
210                 215                 220

Leu Leu Leu Gln Lys Glu Ala Gly Cys Arg Leu Ile Val Val His Val
225                 230                 235                 240

Ser Asn Pro Gly Gly Val Glu Leu Ile His Lys Ala Gln Ser Glu Gly
            245                 250                 255

Gln Asp Val His Cys Glu Ser Gly Pro Gln Tyr Leu Asn Leu Thr Met
        260                 265                 270

Asp Asp Ala Glu Lys Val Gly Pro Tyr Met Lys Ile Ala Pro Pro Val
    275                 280                 285

Arg Ser Ala Glu Leu Asn Ala Val Leu Trp Glu Gln Leu Glu Lys Gly
290                 295                 300

Tyr Ile Asp Thr Leu Gly Ser Asp His Gly Gly His Pro Val Glu Asn
305                 310                 315                 320

Lys Glu Gly Gly Trp Asp Asp Ile Trp Thr Ala Ser Asn Gly Ala Leu
            325                 330                 335

Gly Leu Glu Thr Ser Leu Pro Met Met Leu Thr Asn Gly Val Asn Lys
        340                 345                 350

Gly Arg Val Ser Leu Glu Arg Leu Val Glu Val Met Cys Glu Asn Pro
    355                 360                 365

Ala Lys Leu Phe Gly Ile Tyr Pro Gln Lys Gly Thr Leu Gln Val Gly
370                 375                 380

Ser Asp Ala Asp Leu Leu Ile Leu Asp Leu Glu Ile Glu Asp Arg Lys
385                 390                 395                 400

Val Asp Ala Ser Gln Phe Arg Ser Leu His Tyr Ser Pro Phe Asp
            405                 410                 415

Gly Arg Pro Val Thr Gly Ala Pro Val Leu Thr Met Ile Arg Gly Thr
        420                 425                 430

Val Val Ala Gln Asp Gly Glu Ile Leu Val Asp Gln Gly Phe Gly Gln
```

```
              435                 440                 445

Phe Val Thr Arg Arg Asp Ser Glu Val Ser Ser
    450                 455

<210> SEQ ID NO 17
<211> LENGTH: 236
<212> TYPE: PRT
<213> ORGANISM: Arthrobacter aurescens
<220> FEATURE:
<221> NAME/KEY: misc_feature
<222> LOCATION: 1..236
<223> OTHER INFORMATION: Arthrobacter aurescens DSM 3745 (strain)
<220> FEATURE:
<221> NAME/KEY: gene
<222> LOCATION: 1..236
<223> OTHER INFORMATION: HyuR

<400> SEQUENCE: 17

Met Arg Ile Leu Val Ile Asn Pro Asn Ser Ser Ala Leu Thr Glu
1               5                   10                  15

Ser Val Ala Asp Ala Ala Gln Gln Val Val Ala Thr Gly Thr Ile Ile
            20                  25                  30

Ser Ala Ile Asn Pro Ser Arg Gly Pro Ala Val Ile Glu Gly Ser Phe
            35                  40                  45

Asp Glu Ala Leu Ala Thr Phe His Leu Ile Glu Glu Val Glu Arg Ala
    50                  55                  60

Glu Arg Glu Asn Pro Pro Asp Ala Tyr Val Ile Ala Cys Phe Gly Asp
65                  70                  75                  80

Pro Gly Leu Asp Ala Val Lys Glu Leu Thr Asp Arg Pro Val Val Gly
                85                  90                  95

Val Ala Glu Ala Ala Ile His Met Ser Ser Phe Val Ala Ala Thr Phe
            100                 105                 110

Ser Ile Val Ser Ile Leu Pro Arg Val Arg Lys His Leu His Glu Leu
            115                 120                 125

Val Arg Gln Ala Gly Ala Thr Asn Arg Leu Ala Ser Ile Lys Leu Pro
    130                 135                 140

Asn Leu Gly Val Met Ala Phe His Glu Asp Glu His Ala Ala Leu Glu
145                 150                 155                 160

Thr Leu Lys Gln Ala Ala Lys Glu Ala Val Gln Glu Asp Gly Ala Glu
                165                 170                 175

Ser Ile Val Leu Gly Cys Ala Gly Met Val Gly Phe Ala Arg Gln Leu
            180                 185                 190

Ser Asp Glu Leu Gly Val Pro Val Ile Asp Pro Val Glu Ala Ala Cys
            195                 200                 205

Arg Val Ala Glu Ser Leu Val Ala Leu Gly Tyr Gln Thr Ser Lys Ala
    210                 215                 220

Asn Ser Tyr Gln Lys Pro Thr Glu Lys Gln Tyr Leu
225                 230                 235

<210> SEQ ID NO 18
<211> LENGTH: 249
<212> TYPE: PRT
<213> ORGANISM: Pseudomonas sp.
<220> FEATURE:
<221> NAME/KEY: misc_feature
<222> LOCATION: 1..249
<223> OTHER INFORMATION: Pseudomonas sp. NS671 (strain)
<220> FEATURE:
<221> NAME/KEY: gene
<222> LOCATION: 1..249
<223> OTHER INFORMATION: HyuE
```

<400> SEQUENCE: 18

Met Lys Ile Lys Val Ile Asn Pro Asn Thr Thr Leu Ala Met Thr Lys
1               5                   10                  15

Gly Ile Glu His Ala Ala Lys Ser Ala Ala Arg Ser Asp Thr Gln Ile
            20                  25                  30

Val Ala Val Ser Pro Lys Met Gly Pro Ala Ser Ile Glu Ser Tyr Tyr
        35                  40                  45

Asp Glu Tyr Leu Ser Ile Pro Gly Val Ile Glu Ile Lys Lys Gly
    50                  55                  60

Glu Glu Glu Gly Val Asp Ala Phe Val Ile Ala Cys Trp Gly Asp Pro
65                  70                  75                  80

Gly Leu His Ala Ala Arg Glu Val Thr Asp Lys Pro Val Val Gly Ile
            85                  90                  95

Ala Glu Ser Ser Val Tyr Leu Ala Ser Met Leu Ala Ala Arg Phe Ser
        100                 105                 110

Val Val Thr Val Leu Pro Arg Ile Lys Thr Met Leu Glu Asp Leu Val
        115                 120                 125

Asp Ser Tyr Gly Met Gln Lys Arg Val Leu Asn Ile Arg Thr Thr Pro
    130                 135                 140

Met Gly Val Leu Asp Phe Glu Arg Asp Pro Glu Ala Gly Ile Glu Met
145                 150                 155                 160

Leu Arg Gln Glu Gly Lys Arg Ala Val Glu Glu Asp Asn Ala Glu Ala
            165                 170                 175

Ile Leu Leu Gly Cys Ala Gly Met Ala Glu Phe Ala Asp Ser Leu Glu
        180                 185                 190

Lys Glu Leu Gly Val Pro Val Ile Asp Gly Val Val Ala Gly Val Lys
    195                 200                 205

Phe Ala Glu Thr Ile Val Asp Leu Gly Lys Lys Thr Ser Lys Leu Lys
210                 215                 220

Thr Tyr Lys Tyr Pro Glu Lys Lys Glu Tyr Val Gly Ala Leu Glu Asn
225                 230                 235                 240

Phe Gly Arg Asn Gln Thr Thr Thr Lys
                245

<210> SEQ ID NO 19
<211> LENGTH: 244
<212> TYPE: PRT
<213> ORGANISM: Rhodococcus
<220> FEATURE:
<221> NAME/KEY: misc_feature
<222> LOCATION: 1..244
<223> OTHER INFORMATION: Rhodococcus R04 (strain)
<220> FEATURE:
<221> NAME/KEY: gene
<222> LOCATION: 1..244
<223> OTHER INFORMATION: Hyu2

<400> SEQUENCE: 19

Met Phe Ile Lys Val Val Asn Pro Asn Thr Thr Trp Ser Met Thr Ala
1               5                   10                  15

Thr Ile Glu Ala Cys Ala Arg Ala Val Ala Gly Pro Gly Thr Arg Val
            20                  25                  30

Glu Ala Val Ser Pro Thr Met Gly Pro Pro Ser Ile Glu Ser His Tyr
        35                  40                  45

Asp Asp Ala Leu Ala Val Pro Gly Ile Leu Thr Glu Ile Glu Lys Gly
    50                  55                  60

```
Glu Arg Asp Gly Val Asp Gly Tyr Val Ile Ala Cys Phe Gly Asp Pro
 65                  70                  75                  80

Gly Leu Asp Ala Ala Arg Glu Leu Ala Gly Gly Pro Val Val Gly Ile
                 85                  90                  95

Ala Glu Ala Ala Met His Thr Ala Ala Val Leu Gly Arg Gly Phe Ser
            100                 105                 110

Val Val Thr Thr Leu Ala Arg Thr Gly Arg Ala Trp Asp Leu Ala
            115                 120                 125

His Arg Tyr Gly Met Arg Asp Ala Cys Arg Gly Val His Ala Cys Asp
            130                 135                 140

Leu Pro Val Leu Ala Leu Asp Ser Glu Pro Asp Ala Arg Lys Ile Val
145                 150                 155                 160

Thr Glu Ala Cys Leu Asp Ala Leu Tyr Glu Asp Gly Ser Asp Ala Ile
                165                 170                 175

Val Leu Gly Cys Ala Gly Met Ala Asp Leu Cys Ala His Ile Ser Ala
                180                 185                 190

Glu Ile Gly Val Pro Val Val Asp Gly Val Ala Ala Thr Leu Thr
            195                 200                 205

Val Gln Ser Leu Val Thr Met Gly Leu Ala Thr Gly Lys Arg Gly Glu
210                 215                 220

Phe Ala Ala Pro Pro Lys Arg Tyr Ala Gly Leu Leu Asp Gly Phe
225                 230                 235                 240

Thr Thr Gly Gly

<210> SEQ ID NO 20
<211> LENGTH: 236
<212> TYPE: PRT
<213> ORGANISM: Microbacterium liquefaciens
<220> FEATURE:
<221> NAME/KEY: misc_feature
<222> LOCATION: 1..236
<223> OTHER INFORMATION: Microbacterium liquefaciens AJ 3912 (strain)
<220> FEATURE:
<221> NAME/KEY: gene
<222> LOCATION: 1..236
<223> OTHER INFORMATION: HRase

<400> SEQUENCE: 20

Met Arg Ile His Val Ile Asn Pro Asn Ser Ser Val Asp Leu Thr Asp
 1               5                  10                  15

Ala Val Ala Glu Ala Ala Arg Ser Val Val Ser Pro Gly Thr Thr Ile
                 20                  25                  30

Thr Ala Val Asn Pro Ser Lys Gly Pro Thr Val Ile Glu Gly Ser Tyr
             35                  40                  45

Asp Glu Val Leu Ala Thr Tyr His Leu Val Glu Glu Val Arg Arg Ala
 50                  55                  60

Glu Arg Glu Asp Arg Pro Asp Ala Tyr Val Ile Ala Cys Phe Gly Asp
 65                  70                  75                  80

Pro Gly Leu Asp Ala Val Arg Glu Leu Thr Asp Arg Pro Val Val Gly
                 85                  90                  95

Ile Ala Glu Ala Ala Ile Gln Met Thr Ser Phe Val Ala Ala Ser Phe
            100                 105                 110

Ser Ile Val Ser Ile Leu Pro Arg Val Arg Lys His Leu His Glu Leu
            115                 120                 125

Val His Arg Ala Gly Ala Thr Asp Arg Leu Ala Ser Leu Lys Leu Pro
130                 135                 140

Asp Leu Gly Val Leu Ala Phe His Glu Asp Glu Ala Ala Ala Phe Glu
```

```
                145                 150                 155                 160
Thr Leu Arg Arg Val Ala Gly Glu Ala Val Arg Glu Asp Gly Ala Glu
                    165                 170                 175

Ser Ile Val Leu Gly Cys Ala Gly Met Ala Gly Phe Ala Arg Gln Leu
                180                 185                 190

Ser Glu Glu Leu Gly Val Pro Val Ile Asp Ala Val Glu Ala Ala Cys
                195                 200                 205

Arg Val Ala Glu Ser Leu Val Ala Leu Gly Tyr Arg Thr Ser Lys Ala
                210                 215                 220

Asn Thr Tyr Gln Ala Pro Thr Glu Lys Gln Tyr Leu
225                 230                 235

<210> SEQ ID NO 21
<211> LENGTH: 241
<212> TYPE: PRT
<213> ORGANISM: Sinorhizobium meliloti
<220> FEATURE:
<221> NAME/KEY: misc_feature
<222> LOCATION: 1..241
<223> OTHER INFORMATION: Sinorhizobium meliloti strain CECT 4114
      (strain)
<220> FEATURE:
<221> NAME/KEY: gene
<222> LOCATION: 1..241
<223> OTHER INFORMATION: HyuA

<400> SEQUENCE: 21

Met His Ile His Leu Ile Asn Pro Asn Ser Thr Ala Ser Met Thr Ala
1               5                   10                  15

Gln Ala Leu Glu Ser Ala Leu Leu Val Lys His Ala His Thr His Val
                20                  25                  30

Ser Ala Ser Asn Pro Thr Asp Thr Pro Ala Ser Ile Glu Gly Gly Ala
                35                  40                  45

Asp Glu Ala Met Ser Val Pro Gly Met Leu Ala Glu Ile Arg Gln Gly
            50                  55                  60

Glu Ala Gln Gly Val Asp Ala Tyr Val Ile Ala Cys Phe Asp Asp Pro
65              70                  75                  80

Gly Leu His Ala Ala Arg Glu Val Ala Lys Gly Pro Val Ile Gly Ile
                85                  90                  95

Cys Gln Ala Ala Val Gln Val Ala Met Thr Ile Ser Arg Arg Phe Ser
                100                 105                 110

Val Ile Thr Thr Leu Pro Arg Ser Val Pro Ile Ile Glu Asp Leu Val
                115                 120                 125

Ser Asp Tyr Gly Ala Glu Arg His Cys Arg Lys Val Arg Ala Ile Asp
                130                 135                 140

Leu Pro Val Leu Ala Leu Glu Glu Asp Pro Gln Arg Ala Glu Arg Leu
145                 150                 155                 160

Leu Leu Lys Glu Ile Glu Ile Ala Lys Ala Glu Asp Gly Ala Glu Ala
                165                 170                 175

Ile Val Leu Gly Cys Ala Gly Met Ser Ser Leu Cys Asp Arg Leu Gln
                180                 185                 190

Lys Ala Thr Gly Val Pro Val Ile Asp Gly Val Thr Ala Ala Val Lys
                195                 200                 205

Met Ala Glu Ala Leu Leu Gly Ala Gly Tyr Ala Thr Ser Lys Val Asn
                210                 215                 220

Thr Tyr Ala Tyr Pro Arg Ile Lys Ala Ala Ala Gly His Lys Val Cys
225                 230                 235                 240
```

Ala

<210> SEQ ID NO 22
<211> LENGTH: 243
<212> TYPE: PRT
<213> ORGANISM: Flavobacterium sp.
<220> FEATURE:
<221> NAME/KEY: misc_feature
<222> LOCATION: 1..243
<223> OTHER INFORMATION: Flavobacterium sp. AJ 11199 (strain)
<220> FEATURE:
<221> NAME/KEY: gene
<222> LOCATION: 1..243
<223> OTHER INFORMATION: HRase

<400> SEQUENCE: 22

```
Met Lys Ile Lys Val Ile Asn Pro Asn Thr Thr Leu Thr Met Thr Ala
1               5                   10                  15

Lys Ile Gly Glu Ala Ala Ala Val Ala Ser Ala Gly Thr Glu Val
            20                  25                  30

Val Ala Val Ser Pro Ala Met Gly Pro Ala Ser Ile Glu Gly His Tyr
        35                  40                  45

Asp Glu Ala Val Ser Ala Leu Gly Val Leu Asp Glu Val Arg Lys Gly
    50                  55                  60

Lys Ala Glu Gly Cys Asp Gly Tyr Leu Ile Ala Cys Phe Asp Asp Pro
65                  70                  75                  80

Gly Leu Gln Ala Ala Arg Glu Ile Ala Asp Gly Pro Val Val Gly Ile
                85                  90                  95

Ala Glu Ala Ala Met His Met Ala Ser Phe Val Ser Glu Gly Phe Ser
            100                 105                 110

Val Val Ala Thr Gly His Arg Ser Arg Ile Ile Leu Glu His Leu Ala
        115                 120                 125

Arg Ser Tyr Gly Met Glu His Lys Cys Arg Lys Val Arg Thr Thr Glu
    130                 135                 140

Leu Ala Val Leu Asp Leu Glu Val Glu Gly Ser Asp Ala Arg Gly Ile
145                 150                 155                 160

Ile Leu Glu Glu Cys Arg Arg Ala Ile Val Glu Asp His Ser Asp Cys
                165                 170                 175

Ile Val Leu Gly Cys Ala Gly Met Ala Asp Leu Ala Asp Tyr Ile Ser
            180                 185                 190

Lys Glu Leu Gly Val Pro Val Val Asp Gly Val Ala Ala Gly Val Lys
        195                 200                 205

Val Leu Glu Gly Leu Ile Gly Leu Arg Leu Ser Thr Ser Arg Ala Cys
    210                 215                 220

Gly Tyr Ala Tyr Pro Asn Pro Lys Thr Tyr Ser Gly Glu Met Ala Arg
225                 230                 235                 240

Phe Gln Pro
```

<210> SEQ ID NO 23
<211> LENGTH: 247
<212> TYPE: PRT
<213> ORGANISM: Agrobacterium sp.
<220> FEATURE:
<221> NAME/KEY: misc_feature
<222> LOCATION: 1..247
<223> OTHER INFORMATION: Agrobacterium sp. IP I-671 (strain)
<220> FEATURE:
<221> NAME/KEY: gene
<222> LOCATION: 1..247
<223> OTHER INFORMATION: HyuA

<400> SEQUENCE: 23

```
Met Lys Ile Lys Val Ile Asn Pro Asn Thr Thr Trp Thr Met Thr Asp
1               5                   10                  15

Lys Ile Ala Gly Ala Ala Arg Ala Ala Ala Pro Gly Thr Glu Ile
            20                  25                  30

Val Ala Val Ser Pro Asp Met Gly Pro Val Ser Ile Glu Gly Tyr Tyr
            35                  40                  45

Asp Glu Val Phe Ala Ala Val Gly Val Val Asp Glu Val Arg Lys Gly
            50                  55                  60

Glu Leu Glu Gly Cys Asp Gly Tyr Val Ile Ala Cys Phe Gly Asp Pro
65                  70                  75                  80

Gly Leu Asn Ala Ala Arg Glu Val Ala Arg Gly Pro Val Ile Gly Ile
                85                  90                  95

Ala Glu Ala Ala Met His Ala Ala Ser Leu Ile Gly Gly Ser Phe Ser
                100                 105                 110

Ile Ile Ser Met Leu Gly Arg Ser Arg Gly Val Leu Glu His Leu Val
            115                 120                 125

His Ser Tyr Gly Met Ala His Lys Cys Arg Ser Val Arg Met Thr Asp
    130                 135                 140

Leu Pro Val Leu Glu Phe Glu Glu Gly Ser Asp Ala Arg Arg Ile
145                 150                 155                 160

Val Val Glu Glu Cys Arg Arg Ala Ile Glu Gln Asp His Ala Asp Ser
                165                 170                 175

Val Leu Leu Gly Cys Gly Gly Met Ser Asp Leu Met Ala Tyr Val Ser
            180                 185                 190

Gln Glu Ile Gly Ala Pro Ala Ile Asp Gly Val Ser Ala Gly Val Lys
        195                 200                 205

Leu Val Glu Ala Leu Val Gly Met Gly Leu Gly Thr Ser Lys Arg Ala
    210                 215                 220

Gly Leu Arg Leu Ser Asp Arg Glu Ser Leu His Cys Ser Phe Ser Ser
225                 230                 235                 240

Phe Ala Pro Ser Arg Pro Arg
                245
```

<210> SEQ ID NO 24
<211> LENGTH: 247
<212> TYPE: PRT
<213> ORGANISM: Pasteurella sp.
<220> FEATURE:
<221> NAME/KEY: misc_feature
<222> LOCATION: 1..247
<223> OTHER INFORMATION: Pasteurella sp. AJ 11221 (strain)

<400> SEQUENCE: 24

```
Met Lys Ile Lys Val Ile Asn Pro Asn Thr Thr Trp Ser Met Thr Glu
1               5                   10                  15

Lys Ile Gly Glu Ala Ala Arg Arg Val Ala Ala Pro Gly Thr Glu Ile
            20                  25                  30

Val Ala Val Ser Pro Ala Met Gly Pro Val Ser Ile Glu Gly Phe Tyr
            35                  40                  45

Asp Glu Ala Phe Ala Ala Ile Gly Val Ile Asp Glu Val Arg Lys Gly
            50                  55                  60

Glu Glu Glu Gly Cys Asp Gly Tyr Val Ile Ala Cys Phe Gly Asp Pro
65                  70                  75                  80

Gly Leu Leu Ala Ala Arg Glu Ile Ala Arg Gly Pro Val Val Ile Ala
                85                  90                  95
```

```
Glu Ala Ala Met His Ala Ala Ser Leu Ile Gly Asn Gly Phe Thr Ile
                100                 105                 110

Val Ser Met Leu Glu Arg Thr Arg Ala Thr Met Glu His Leu Val His
            115                 120                 125

Ala Tyr Gly Met Ser His Lys Cys Arg Asn Ile Arg Met Thr Asp Leu
        130                 135                 140

Pro Val Leu Glu Leu Glu Lys Glu Gly Ser Asn Ala Gln Ala Ile Ile
145                 150                 155                 160

Met Glu Glu Cys Arg Arg Ala Leu Glu Glu Asp His Ser Asp Ala Val
                165                 170                 175

Leu Leu Gly Cys Gly Gly Met Ser Asp Leu Met Ala Leu Ile Thr Arg
            180                 185                 190

Glu Ile Gly Ala Pro Ala Ile Asp Gly Val Ser Ser Gly Val Lys Leu
        195                 200                 205

Val Glu Ala Leu Val Ser Leu Gly Leu Gly Thr Ser Lys Arg Gln Ala
210                 215                 220

Tyr Ala Tyr Pro Val Glu Lys Thr Tyr Thr Gly Ser Phe Ser Gln Phe
225                 230                 235                 240

Ser Val Pro Ala Ala Asn Val
                245

<210> SEQ ID NO 25
<211> LENGTH: 228
<212> TYPE: PRT
<213> ORGANISM: Pyrococcus horikoshii
<220> FEATURE:
<221> NAME/KEY: misc_feature
<222> LOCATION: 1..228
<223> OTHER INFORMATION: Pyrococcus horikoshii OT3 (strain)
<220> FEATURE:
<221> NAME/KEY: gene
<222> LOCATION: 1..228
<223> OTHER INFORMATION: PH1054

<400> SEQUENCE: 25

Met Tyr Arg Met Asp Lys Tyr Thr Ile Gly Leu Ile Arg Val Ile Thr
1               5                   10                  15

Leu Glu Asp Lys Glu Ile Leu Asn Leu His Gly Arg Ile Ile Glu Ser
            20                  25                  30

Ala Phe Pro Glu Leu Lys Val Val Ser Arg Cys Ile Glu Asp Gln Pro
        35                  40                  45

Lys Gly Ile Tyr Asn Glu Glu Thr Glu Arg Glu Ala Glu Pro Lys Ile
    50                  55                  60

Ile Arg Leu Ala Lys Glu Phe Glu Arg Glu Gly Val Asp Ala Ile Ile
65                  70                  75                  80

Ile Ser Cys Ala Ala Asp Pro Ala Val Glu Lys Val Arg Lys Leu Leu
                85                  90                  95

Ser Ile Pro Val Ile Gly Ala Gly Ser Ser Val Ser Ala Leu Ala Leu
            100                 105                 110

Ala Tyr Gly Arg Arg Val Gly Val Leu Asn Leu Thr Glu Glu Thr Pro
        115                 120                 125

Lys Val Ile Arg Ser Ile Leu Gly Asn Asn Leu Ile Ala Glu Asp His
    130                 135                 140

Pro Ser Gly Val Ser Asn Thr Leu Asp Leu Leu Thr Asp Trp Gly Arg
145                 150                 155                 160

Arg Glu Val Ile Asn Ala Ala Lys Arg Leu Lys Glu Lys Gly Val Glu
                165                 170                 175
```

```
Val Ile Ala Leu Gly Cys Thr Gly Met Ser Thr Ile Gly Ile Ala Pro
            180                 185                 190

Val Leu Glu Glu Glu Val Gly Ile Pro Val Ile Asp Pro Val Ile Ala
            195                 200                 205

Ser Gly Ala Val Ala Leu His Ala Leu Lys Arg Arg Glu Val Lys Arg
210                 215                 220

Phe Glu Gly Arg
225

<210> SEQ ID NO 26
<211> LENGTH: 236
<212> TYPE: PRT
<213> ORGANISM: Arthrobacter sp.
<220> FEATURE:
<221> NAME/KEY: misc_feature
<222> LOCATION: 1..236
<223> OTHER INFORMATION: Arthrobacter sp. BT801 (strain)
<220> FEATURE:
<221> NAME/KEY: gene
<222> LOCATION: 1..236
<223> OTHER INFORMATION: HyuA

<400> SEQUENCE: 26

Met Arg Ile His Ile Ile Asn Pro Asn Ser Ser Glu Leu Thr Glu
1               5                   10                  15

Ala Val Ala Glu Thr Ala Arg Ser Val Val Ser Ala Gly Thr Ala Val
            20                  25                  30

Thr Ala Val Asn Pro Ser Ser Gly Pro Ala Val Ile Glu Gly Ser Tyr
            35                  40                  45

Asp Glu Ala Leu Ala Thr Tyr His Leu Val Gln Glu Val Met Arg Ala
50                  55                  60

Glu Arg Glu Asp Arg Pro Asp Ala Tyr Val Ile Ala Cys Phe Gly Asp
65                  70                  75                  80

Pro Gly Leu Asn Ala Val Arg Glu Leu Thr Glu Lys Pro Val Val Gly
            85                  90                  95

Ile Ala Glu Ala Ala Ile Gln Leu Ser Ser Phe Ile Gly Ala Thr Phe
            100                 105                 110

Ser Ile Val Ser Thr Leu Pro Arg Val Arg Ser His Leu His Gly Leu
            115                 120                 125

Val Arg Arg Ala Gly Ala Thr Asn Arg Leu Ala Ser Val Lys Thr Pro
            130                 135                 140

Asp Leu Gly Val Met Ala Phe His Glu Asp Ala Gly Ser Ala Gln Ala
145                 150                 155                 160

Thr Leu Glu Gln Ala Ala Lys Glu Ala Val Gln Glu Asp Gly Ala Glu
            165                 170                 175

Val Val Val Leu Gly Cys Ala Gly Met Ala Gly Leu Ala Arg Arg Leu
            180                 185                 190

Ser Glu Glu Leu Gln Val Pro Val Ile Asp Pro Val Glu Ala Ala Cys
            195                 200                 205

Arg Val Ala Glu Ser Leu Ser Ala Leu Gly Tyr Gly Thr Ser Lys Ala
            210                 215                 220

Asn Thr Tyr Glu Lys Pro Thr Glu Lys Val Tyr Asn
225                 230                 235

<210> SEQ ID NO 27
<211> LENGTH: 1263
<212> TYPE: DNA
<213> ORGANISM: Arthrobacter aurescens
```

```
<220> FEATURE:
<221> NAME/KEY: misc_feature
<222> LOCATION: 1..1263
<223> OTHER INFORMATION: Arthrobacter aurescens DSM 3747 (strain)
<220> FEATURE:
<221> NAME/KEY: gene
<222> LOCATION: 1..1263
<223> OTHER INFORMATION: hyuC

<400> SEQUENCE: 27
atgaccctgc agaaagcgca agcggagcgc attgagaaag agatctggga gctctcccgg      60
ttctcggcgg aaggccccgg tgttacccgg ctgacctaca ctccagagca tgccgccgcg     120
cgggaaacgc tcattgcggc tatggaagcg gccgctttga cgttcgtga agacgctctc      180 gggaacatca tcggccgacg tgaaggcact gatccgcagc tccctgcgat cgcggtcggt     240
tcacacttcg attctgtccg aaacggcggg atgttcgatg gcactgcagg cgtggtgtgc     300
gcccttgagg ctgcccgggt gatgctggag agcggctacg tgaatcggca tccatttgag    360
ttcatcgcga tcgtggagga ggaagggggcc cgcttcagca gtggcatgtt gggcggccgg    420
gccattgcag gtttggtcgc cgacagggaa ctggactctt tggttgatga ggatggagtg    480
tccgttaggc aggcggctac tgccttcggc ttgaagccgg cgaactgca ggctgcagcc     540 cgctccgcgg cggacctgcg tgcttttatc gaactacaca ttgaacaagg accgatcctc    600
gagcaggagc aaatagagat cggagttgtg acctccatcg ttggcgttcg cgcattgcgg    660
gttgctgtca aggcagaag cgcacacgcc ggcacaaccc ccatgcacct cgccaggat     720 gcgctggtac ccgccgctct catggtgcgg gaggtcaacc ggttcgtcaa cgagatcgcc    780
gatggcacag tggctaccgt tggccaccc acagtggccc ccgtggcgg caaccaggtc     840 ccggggagg tggagttcac actggacctg cgttctccgc atgaggagtc gctccgggtg     900
ttgatcaacc gcatctcggt catggtcggc gaggtcgcct cgcaggccgg tgtggctgcc    960
gatgtggatg aatttttcaa tctcagcccg gtgcagctgg ctcctaccat ggtggacgcc   1020
gttcgcgaag cggcctcggc cctgcagttc acgcaccggg atatcagcag tggggcgggc   1080
cacgactcga tgttcatcgc ccaggtcacg gacgtcggaa tggttttcgt tccaagccgt   1140
gctggccgga gccacgttcc cgaagaatgg accgatttcg atgaccttcg caagggaact   1200
gaggttgtcc tccgggtaat gaaggcactt gaccggggat cccatcatca tcatcatcat   1260
tga                                                                  1263

<210> SEQ ID NO 28
<211> LENGTH: 1377
<212> TYPE: DNA
<213> ORGANISM: Arthrobacter sp.
<220> FEATURE:
<221> NAME/KEY: misc_feature
<222> LOCATION: 1..1377
<223> OTHER INFORMATION: Arthrobacter sp. DSM 9771 (strain)
<220> FEATURE:
<221> NAME/KEY: gene
<222> LOCATION: 1..1377
<223> OTHER INFORMATION: hyuH

<400> SEQUENCE: 28
atgtttgacg taatagttaa gaactgccgt atggtgtcca gcgacggaat caccgaggca      60
gacattctgg tgaaagacgg caaagtcgcc gcaatcagct cggacacaag tgatgttgag    120
gcgagccgaa ccattgacgc gggtggcaag ttcgtgatgc cgggcgtggt cgatgaacat   180
gtgcatatca tcgacatgga tctgaagaac cggtatggcc gcttcgaact cgattccgag    240
```

```
tctgcggccg tgggaggcat caccaccatc tttgagatgc cgtttacctt cccgcccacc    300
accactttgg acgccttcct cgaaaagaag aagcaggcgg ggcagcggtt gaaagttgac    360
ttcgcgctct atggcggtgg agtgccggga aacctgcccg agatccgcaa aatgcacgac    420
gccggcgcag tgggcttcaa gtcaatgatg gcagcctcag ttccgggcat gttcgacgcc    480
gtcagcgacg gcgaactgtt cgaaatcttc caggagatcg cagcctgtgg ttcagtcgcc    540
gtggtccatg ccgagaatga aacgatcatt caagcgctcc agaagcagat caaagccgct    600
ggtcgcaagg acatggccgc ctacgaggca tcccaaccag ttttccagga gaacgaggcc    660
attcagcgtg cgttactact gcagaaagaa gccggctgtc gactgattgt gcttcacgtg    720
agcaaccctg acggggtcga gctgatacat cgggcgcaat ccgagggcca ggacgtccac    780
tgcgagtcgg gtccgcagta tctgaatatc accacggacg acgccgaacg aatcggaccg    840
tatatgaagg tcgcgccgcc cgtccgctca gccgagatga acgtcagatt atgggaacaa    900
cttgagaacg ggctcatcga caccttgggg tcagccacg gcggacatcc tgtcgaggac    960
aaagaacccg gctggaagga cgtgtggaaa gccggcaacg gtgcgctggg ccttgagaca    1020
tccctgccta tgatgctgac caacggagtg aataaaggca ggctatcctt ggaacgcctc    1080
gtcgaggtga tgtgcgagaa acctgcgaag ctctttggca tctatccgca gaagggcacg    1140
ctacaggttg gttccgacgc cgatctgctc atcctcgatc tggatattga caccaaagtg    1200
gatgcctcgc agttccgatc cctgcataag tacagcccgt tcgacgggat gcccgtcacg    1260
ggtgcaccgg ttctgacgat ggtgcgcgga acggtggtgg cagagaaggg agaagttctg    1320
gtcgagcagg gattcggcca gttcgtcacc cgtcacgact acgaggcgtc gaagtga       1377
```

<210> SEQ ID NO 29  
<211> LENGTH: 711  
<212> TYPE: DNA  
<213> ORGANISM: Arthrobacter aurescens  
<220> FEATURE:  
<221> NAME/KEY: misc_feature  
<222> LOCATION: 1..711  
<223> OTHER INFORMATION: Arthrobacter aurescens DSM 3745 (strain)  
<220> FEATURE:  
<221> NAME/KEY: gene  
<222> LOCATION: 1..711  
<223> OTHER INFORMATION: hyuR

<400> SEQUENCE: 29

```
atgagaatcc tcgtgatcaa ccccaacagt tccagcgccc ttactgaatc ggttgcggac     60
gcagcacaac aagttgtcgc gaccggcacc ataatttctg ccatcaaccc ctccagagga    120
cccgccgtca ttgaaggcag cttttgacgaa gcactggcca cgttccatct cattgaagag    180
gtggagcgcg ctgagcggga aaacccgccc gacgcctacg tcatcgcatg tttcggggat    240
ccgggacttg acgcggtcaa ggagctgact gacaggccag tggtaggagt tgccgaagct    300
gcaatccaca tgtcttcatt cgtcgcggcc acctcctcca ttgtcagcat cctcccgagg    360
gtcaggaaac atctgcacga actggtacgg caagcggggg cgacgaatcg cctcgcctcc    420
atcaagctcc caaatctggg ggtgatggcc ttccatgagg acgaacatgc cgcactggag    480
acgctcaaac aagccgccaa ggaggcggtc caggaggacg cgccgagtc gatagtgctc    540
ggatgcgccg gcatggtggg gtttgcgcgt caactgagcg acgaactcgg cgtccctgtc    600
atcgaccccg tcgaggcagc ttgccgcgtg gccgagagtt tggtcgctct ggcgctaccag    660
accagcaaag cgaactcgta tcaaaaaccg acagagaagc agtacctcta g             711
```